United States Patent [19]

Anderson et al.

[11] Patent Number: 5,506,192

[45] Date of Patent: Apr. 9, 1996

[54] SUBSTITUTED PHTHALIDES AND HETEROCYCLIC PHTHALIDES

[75] Inventors: Richard J. Anderson, Palo Alto; Ian S. Cloudsdale, Boulder Creek; Takeo Hokama, Sunnyvale, all of Calif.

[73] Assignee: Sandoz Ltd.

[21] Appl. No.: 201,150

[22] Filed: Feb. 23, 1994

Related U.S. Application Data

[63] Continuation of Ser. No. 36,006, Mar. 23, 1993, abandoned, which is a continuation-in-part of Ser. No. 804,150, Dec. 6, 1991, abandoned, which is a continuation-in-part of Ser. No. 633,592, Dec. 21, 1990, abandoned, which is a continuation-in-part of Ser. No. 534,794, Jun. 7, 1990, abandoned.

[51] Int. Cl.$^6$ ............ A01N 43/54; C07D 239/52; C07D 239/34; C07D 239/26
[52] U.S. Cl. ............ 504/243; 504/239; 504/242; 544/319
[58] Field of Search ............ 544/319; 514/269; 504/239, 242, 243

[56] References Cited

U.S. PATENT DOCUMENTS

| 3,133,066 | 5/1964 | Hemingway et al. | 544/319 X |
|---|---|---|---|
| 3,654,204 | 4/1972 | Kim et al. | 544/319 X |
| 3,927,214 | 12/1975 | Barth | 544/319 X |
| 4,923,501 | 5/1990 | Saito et al. | 71/92 |
| 5,015,285 | 5/1991 | Rheinheimer et al. | 544/319 X |
| 5,137,564 | 8/1992 | Jones | 71/92 |
| 5,317,005 | 6/1992 | Jones | 504/239 |

FOREIGN PATENT DOCUMENTS

| 249708 | 12/1987 | European Pat. Off. | C07D 239/06 |
|---|---|---|---|
| 4026177 | 2/1992 | Germany | C07D 251/4 |
| 1301668 | 12/1989 | Japan | C07D 239/52 |
| 9216511 | 10/1992 | WIPO | C07D 239/52 |

Primary Examiner—Johann Richter
Assistant Examiner—Michael G. Ambrose
Attorney, Agent, or Firm—Allen E. Norris

[57] ABSTRACT

Substituted phthalides and heterocyclic phthalides and derivatives thereof which are useful as herbicides are described.

35 Claims, No Drawings

SUBSTITUTED PHTHALIDES AND HETEROCYCLIC PHTHALIDES

This is a continuation of application Ser. No. 08/036,006, filed Mar. 23, 1993, now abandoned, which is a continuation-in-part of application Ser. No. 07/804,150, filed Dec. 6, 1991, now abandoned, which is a continuation-in-part of application Ser. No. 07/633,592, filed Dec. 21, 1990, now abandoned, which is a continuation-in-part of application Ser. No. 07/534,794, filed Jun. 7, 1990, now abandoned.

The present invention concerns substituted phthalides and heterocyclic phthalides and derivatives thereof, processes for their production, compositions containing them and their use in agriculture.

More particularly, the invention concerns compounds of formula I

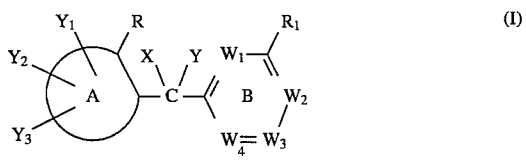

wherein ring system A is selected from
a) phenyl or naphthyl
b) pyridyl which may be fused by its (b) or (c) side to benzene
c) pyridyl-N-oxide or pyrazinyl-N-oxide
d) pyrimidinyl
e) pyrazinyl
f) 3- or 4- cinnolynyl or 2-quinoxalinyl, and
g) a five membered heteroaromatic ring comprising oxygen, sulphur or nitrogen as heteroatom(s) which ring may be fused to a benzene ring or may comprise nitrogen as an additional heteroatom.

R is cyano, formyl, $CX_1X_2X_3$, a ketone forming group, a carboxyl group which may be in the form of the free acid or in ester or salt form, a thiocarboxyl group which may be in the form of the free acid or in ester form, a carbamoyl group or a mono- or di- substituted carbamoyl group, hydroxyalkyl, hydroxybenzyl, —CH=NOH, —CH=NO— lower alkyl, the group —CH$_2$—O—C(O)— which bridges adjacent carbon atoms in ring A, or a ring C

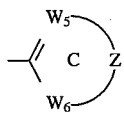

$Y_1$, $Y_2$ and $Y_3$ are attached to carbon atoms and are independently hydrogen, halogen, hydroxy, alkyl, alkenyl, alkynyl, alkoxy, alkenyloxy, alkynyloxy, alkylsulfonyloxy, dialkylsulfamoyloxy, alkylsulfonyl, alkylsulfinyl, dialkylcarbamoyloxy, alkylthio, alkenylthio or alkynylthio each of which may in turn be substituted by 1 to 6 halogen atoms; dialkoxymethyl, conjugated alkoxy, hydroxyalkyl, carboxyl, acyl, acylalkyl, acyloxy, acyloxyalkyl, trialkylsilyloxy, trialkylsilyl, cyano, nitro, amino or substituted amino, aminosulfonyl; cycloalkyl, aryl, aralkyl, aralkenyl, aralkynyl, aryloxy, aralkoxy, arylsulfonyl, arylsulfinyl, arylthio or aralkylthio, each of which may be substituted by one to three substituents selected from halogen, alkyl, haloalkyl, alkoxy, haloalkoxy, nitro, cyano, alkylthio, acyl, amino or substituted amino; a group

wherein R' is hydrogen, lower alkyl, or lower alkoxy; or $Y_1$ and R taken together on adjacent carbon atoms form a bridge having the formula

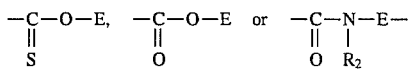

wherein E is a direct bond or a 1 to 3 membered linking group with elements selected from methylene, substituted methylene,

and oxygen.
or $Y_1$ and $Y_2$ taken together on adjacent carbon atoms form a 3- to 5-membered bridge comprised of elements selected from methylene, substituted methylene,

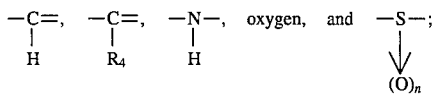

each of $W_1$, $W_2$, $W_3$, $W_4$ and $W_5$ is independently CH, $CR_3$ or nitrogen; $W_6$ is NH, oxygen, sulfur,

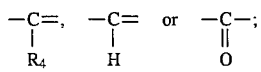

Z is a 2- or 3-membered bridge comprised of elements selected from methylene, substituted methylene,

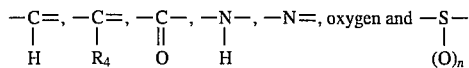

$R_1$ and $R_3$ each is independently hydrogen; halogen; alkyl, alkenyl, alkynyl, alkoxy, alkenyloxy, alkynyloxy, alkylthio, alkenylthio or alkynylthio, each of which may in turn be substituted by 1 to 6 halogen atoms; cycloalkyl, heterocycloalkoxy, aryloxy, aralkoxy or aralkylthio each of which may be substituted by 1 to 3 substituents selected from halogen, alkyl, haloalkyl, alkoxy, haloalkoxy, nitro, cyano, alkylthio, acyl, amino or substituted amino; aminoxy; substituted aminoxy; iminoxy; substituted iminoxy; amino; substituted amino; amido; substituted amido; alkylsulfonylmethyl; cyano; nitro; or

wherein $Y_4$ is hydrogen, lower alkyl, lower alkoxy, hydroxy or unsubstituted or substituted phenyl.

$R_4$ is as defined for $Y_1$ except for hydrogen.

X and Y each is independently hydrogen, hydroxy, halogen, cyano, nitro, alkyl, alkoxy, alkoxycarbonyl, alkoxycarbonyloxy, hydroxyalkyl, haloalkyl, acyl, acyloxy, carbamoyl, carbamoyloxy, alkylthio, alkylsulfinyl, alkylsulfonyl or alkylsulfonyloxy; aryl, aryloxy, $arylS(O)_p$, aralkyl, aralkoxy, $aralkS(O)_p$, arylsulphonyloxy, each of which may in turn be substituted by 1 to 3 substituents selected from halogen, alkyl, haloalkyl, alkoxy, haloalkoxy, nitro, cyano, alkylthio, acyl; amino, substituted amino or together represent =O, =S, =NH, =$NOR_{12}$ or =$CR_{13}R_{14}$; or X and R together may form a bridge having the formula
—O—E—,

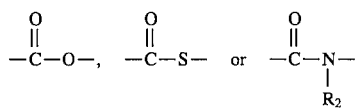

wherein the carbonyl is attached to A, E is defined above and $R_2$ represents hydrogen, hydroxy, alkyl, haloalkyl, alkoxyalkyl, alkoxy, aralkoxy, unsubstituted or substituted aryl, unsubstituted or substituted aralkyl or is as otherwise defined for $R_7$ hereinafter.

P is 0, 1 or 2.

$X_1$, $X_2$ and $X_3$ are independently hydrogen, hydroxy, alkoxy, alkylthio, hydroxyalkyl or hydroxybenzyl whereby at least one of $X_1$, $X_2$ and $X_3$ is other than hydrogen; or $X_3$ represents hydrogen and $X_1$ and $X_2$ together form a four or five membered bridge comprising elements selected from —O(CH$_2$)$_n$O—, $$-OC(CH_2)_mO-$$
$$\|$$
$$O$$

$R_{12}$ is hydrogen or alkyl, $R_{13}$ and $R_{14}$ are independently hydrogen, alkyl or halogen, m is one or two, n' is two or three with the proviso that when R is carboxyl in free ester or salt form and X and Y together are =O one of rings A and B contains a hetero atom.

When R is a ketone forming group this is preferably

wherein R" is alkyl, haloalkyl, alkoxyalkyl, alkenyl, alkynyl, unsubstituted or substituted aryl, unsubstituted or substituted aralkyl.

When R is a carboxyl or thiocarboxyl group in ester form it is preferably of formula —COOR$_5$ or —COSR$_5$ wherein $R_5$ is alkyl, haloalkyl, alkoxyalkyl, alkenyl, haloalkenyl, alkynyl, haloalkynyl, unsubstituted or substituted aryl, unsubstituted or substituted aralkyl, hydroxyalkyl, cycloalkyl, cyanoalkyl, aralkoxyalkyl; a group —N=C(R$_{15}$) (R$_{16}$); a group —(CH$_2$)$_n$·CH(R$_{17}$) (R$_{18}$); a group

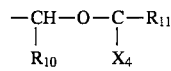

$R_{15}$ and $R_{16}$ are independently hydrogen or alkyl, $R_{17}$ and $R_{18}$ are independently S(O)$_n$alkyl, COOR$_9$, alkoxy, amino, substituted amino, benzyloxy, trimethylsilyl, cyano, —C(R$_{19}$)SR$_{20}$ or additionally one thereof may be hydrogen.

$R_{19}$ is hydrogen or alkyl, $R_{20}$ is alkyl or aryl, $R_9$, $R_{10}$ and $R_{11}$ are independently hydrogen, alkyl, haloalkyl, alkoxyalkyl, unsubstituted or substituted aryl or unsubstituted or substituted aralkyl, n and n" are independently zero, one or two, and $X_4$ is oxygen or sulfur.

When R is a carbamoyl group or a mono- or di-substituted carbamoyl group it is preferably of formula CONR$_7$R$_8$ wherein $R_7$ and $R_8$ are independently hydrogen or an aliphatic or a saturated or unsaturated cyclic or heterocyclic group each of which may be unsubstituted or substituted.

$R_7$ and $R_8$ are preferably each independently a) hydrogen; halogen; b) alkyl, alkenyl, alkynyl, alkoxy, alkoxyalkoxy, alkenyloxy, alkynyloxy, alkylS(O)$_p$, alkenylS(O)$_p$ or alkynylS(O)$_p$, alkylS(O)$_p$alkyl, alkenylS(O)$_p$alkyl, alkynylS(O)$_p$alkyl, each of which may in turn be substituted by 1 to 6 halogen atoms or hydroxy and each of which may be attached to the adjacent nitrogen atom via alkyl; c) acyl, acylalkyl, acyloxy or acyloxyalkyl; d) cycloalkyl, cycloalkylalkyl, heterocyclyl, heterocycloalkyl, heterocycloalkoxy, aryl, aralkyl, aryloxy, aralkoxy, arylS(O)$_p$, aralkylS(O)$_p$ or arylS(O)$_p$alkyl, each of which is unsubstituted or may be substituted by 1 to 3 substituents selected from (i) halogen; (ii) alkyl, alkenyl, alkynyl, alkoxy, alkoxyalkoxy, alkenyloxy, alkynyloxy, alkylS(O)$_p$, alkenylS(O)$_p$ or alkynylS(O)$_p$, alkylS(O)$_p$alkyl, alkenylS(O)$_p$alkyl, alkynylS(O)$_p$alkyl, each of which may in turn be substituted by 1 to 6 halogen atoms; and (iii) nitro, cyano, acyl, amino or substituted amino, aminosulfonyl; aminoalkyl or substituted aminoalkyl; e) amino, substituted amino, amido, substituted amido; aminosulfonyl, cyano, nitro; or

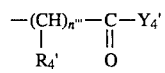

wherein $Y_4'$ is hydrogen, lower alkyl, lower alkoxy or hydroxy and n''' is 0, 1, 2 or 3, and p is 0, 1 or 2.

$R_4'$ is as defined for $Y_1$.

X or Y as carbamoyl is also preferably of formula CONR$_7$R$_8$ as defined above.

When R is carboxyl in salt form the salt is preferably formed with an alkali metal, alkali earth metal, optionally substituted ammonium cation, a trialkyl sulfonium cation, a trialkylsulfoxonium cation or a phosphonium cation, especially the cation of an alkali metal (e.g. the Li or Na cation) or of an earth alkali metal (e.g. the Ca or Mg cation); the ammonium cation; a substituted ammonium cation [such as a $C_{1-5}$alkylammonium cation, a di—C1-5 -alkylammonium cation, a tri-$C_{1-5}$alkylammonium cation, a tetra-$C_{1-5}$ammonium cation, a ($C_{1-5}$alkoxy-alkyl)ammonium cation, a (hydroxy—$C_{1-5}$alkyl)ammonium cation]; a phosphonium cation; a tri($C_{1-8}$alkyl)sulfonium cation; or a tri($C_{1-8}$alkyl)sulfoxonium cation.

When $Y_1$, $Y_2$ and/or $Y_3$ is a carboxyl group this may be in ester or salt form or in amide form (i.e. a carbamoyl) and as such is as described above for R in these forms. Where A has meaning g) it contains one to three heteroatoms and signifies for example thienyl, furanyl, pyrrolyl, oxazolyl, thiazolyl, isoxazolyl, isothiazolyl, imidazolyl, pyrazolyl, oxadiazolyl or thiadiazolyl.

Where A has one of the above defined heteroaromatic significances, b) through g), the substituted hetero ring is particularly selected from pyridyl, quinolyl, pyridyl-N-oxide, pyrimidinyl, pyrazinyl, thienyl or furyl, more particularly from pyridyl or thienyl.

Alkyl moieties unless otherwise specified contain 1 to 8 carbon atoms, preferably 1 to 5, especially 1 to 4, e.g. 1 or 2 carbon atoms. Lower alkyl moieties contain 1 to 4, e.g. 1 or 2 carbon atoms. Alkyl moieties as are present in $R_5$, $R_7$ or $R_8$ contain 1 to 24 preferably 1 to 12, especially 1 to 6 carbon atoms whereby one of $R_7$ and $R_8$ is preferably hydrogen when the other is alkyl.

Alkyl moieties as bridging groups may be straight chain or branched and preferably contain 1 to 4, e.g. 1 or 2 carbon atoms. They may be optionally substituted by aryl or substituted aryl and may optionally be interrupted by or attached via an oxygen or sulfur atom.

"Conjugated alkoxy" stands for an alkoxy group interrupted in its alkyl moiety by one or more oxygen atoms eg alkoxyalkoxy, alkoxyalkoxyalkoxy, etc.

Alkenyl and alkynyl moieties contain 2 to 8, preferably 2 to 4, especially 2 or 3 carbon atoms.

Halogen is preferably F, Cl or Br, especially Cl.

Aryl moieties are preferably as defined for meanings a) to g) of ring system A or as ring B and preferred meanings of each, especially phenyl. Such aryl moieties may be unsubstituted or substituted and in the latter case carry 1 to 3 substituents as defined for $Y_1$ unless otherwise specified.

Substituted amino, -amido, -aminoxy, -aminoalkyl, -iminoxy, -carbamoyl (other than as R) is preferably substituted by one or two substituents selected from alkylalkoxy, haloalkyl, acyl, alkoxyalkyl, unsubstituted or substituted aryl or unsubstituted or substituted aralkyl.

Substituted methylene is preferably substituted by one or two groups as defined for $Y_1$.

Acyl as or as part of a substituent is conveniently

wherein R''' is as defined for $Y_1$ [for example alkyl, haloalkyl, cycloalkyl, alkoxyalkyl, unsubstituted or substituted aryl (especially phenyl)]. Examples of acyl include acetyl, propionyl, butyryl, unsubstituted or substituted benzoyl, pivaloyl or chloracetyl, especially acetyl or unsubstituted or substituted benzoyl.

Cycloalkyl is preferably of 3 to 6 carbon atoms especially cyclopropyl, cyclopentyl or cyclohexyl, heterocyclo is preferably 5 or 6 membered and as defined for A definitions b) to g) and preferences or saturated and containing O, S or N as heteroatom, eg tetrahydrofuryl, piperidinyl, morpholinyl.

For convenience bridging members such as

are so written but are to be understood as embracing

Carbamoyl or substituted carbamoyl moieties are attached to the molecule which they substitute via their carbonyl. Amido or substituted amido moieties are attached to the molecule which they substitute via their nitrogen atom.

A particular group of compounds of formula I (compounds Ia) comprises those wherein ring system A is selected from phenyl, pyridyl or pyridyl-N-oxide.

R is a carboxyl group which may be in the form of the free acid or in ester or salt form, a thiocarboxyl group which may be in the form of the free acid or in ester form, a carbamoyl group or a mono- or di- substituted carbamoyl group.

$Y_1$, $Y_2$ and $Y_3$ are attached to carbon atoms and are independently hydrogen, halogen, alkyl, alkoxy;

each of $W_1$, $W_2$, $W_3$, $W_4$ and $W_5$ is independently CH, $CR_3$ or nitrogen;

$W_6$ is NH or oxygen;

Z is a 2- or 3-membered bridge comprised of elements selected from methylene, substituted methylene or

$R_1$ and $R_3$ each is independently hydrogen, halogen, alkyl, alkoxy, aryloxy or aralkoxy.

X and Y each is independently hydrogen, hydroxy, cyano, alkoxy, acyloxy or together represent =O; or X and R together form a bridge having the formula

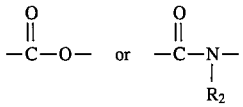

wherein the carbonyl is attached to A.

When R is carboxyl or thiocarboxyl in ester form it is preferably of formula —$COOR_5$ or $COSR_5$;

wherein each $R_5$ is independently alkyl, alkoxyalkyl, alkenyl, alkynyl, substituted aryl or unsubstituted or substituted aralkyl.

When R is carboxy or thiocarboxyl in salt form the salt is preferably formed with an alkali metal, alkali earth metal, optionally substituted ammonium cation especially the cation of an alkali metal (e.g. the Li or Na cation) or of an earth alkali metal (e.g. the Ca or Mg cation); the ammonium cation; a substituted ammonium cation [such as a $C_{1-5}$alkylammonium cation, a di-$C_{1-5}$alkylammonium cation, a tri-$C_{1-5}$alkylammonium cation, a tetra-$C_{1-5}$ammonium cation.

When R is carbamoyl or mono- or di- substituted carbamoyl it is preferably of formula $CONR_7R_8$ wherein $R_7$ is hydrogen, alkyl, haloalkyl, alkoxyalkyl, unsubstituted or substituted aryl or unsubstituted or substituted aralkyl and $R_8$ is hydrogen, alkyl, $NH_2$, $NHR_6$ or $OR_6$ wherein $R_6$ is as defined for $R_7$.

A particular compound group (compounds Ib) comprises those compounds of formula I wherein ring system A represents phenyl, pyridyl or thienyl; B represents pyrimidinyl or triazinyl; R represents a ring C especially oxazole, oxazolone, oxazolidine or oxazolidinone; carboxyl in the form of the free acid or in ester or salt form; substituted carbamoyl, cyano or together with X represent

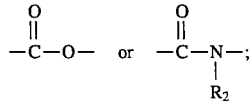

$Y_1$, $Y_2$ and $Y_3$ each represent independently hydrogen, halogen, alkyl, alkoxy, alkylthio or arylthio.

X, Y each represent independently hydrogen, hydroxy, alkoxy, acyloxy, a ring B, halogen, alkylthio or arylthio or together =O or =NH and $R_1$ and $R_3$ each represent independently halogen, alkoxy, alkyl, haloalkoxy, optionally substituted aryloxy, aralkoxy, alkylnyloxy, alkenyloxy.

A further compound group comprises compounds Ib wherein $Y_1$, $Y_2$ and $Y_3$ additionally may each represent independently aralkoxy, alkenyloxy or alkynyloxy.

B is especially pyrimidinyl, particularly 4,6-dimethoxy-2-pyrimidinyl.

A is especially phenyl or pyridyl substituted as defined above.

X and Y are preferably hydrogen, halogen, cyano, hydroxy, alkoxy or together =O, especially hydrogen, hydroxy or together =O.

A further group of compounds according to the invention (Compounds Ic) comprises those of formula I wherein ring system A is pyridyl, R is $CONR_7'R_8'$
wherein $R_7'$ and $R_8'$ represent independently hydrogen, alkoxy, alkyl; or aryl or aralkyl each of which may be unsubstituted or substituted,
X is hydrogen,
Y is $OR_3'$, $SR_3'$ or $OCOR_3'$
wherein $R_3'$ is alkyl; or aryl; or aralkyl each of which may be unsubstituted or substituted,
or X and Y together represent =O or =S and ring system B is m—$CF_3$ phenyl.

Within the group Ib, compounds are preferred wherein X is OH and Y is H or X and Y together represent =O, A is 2- or 3-pyridyl, $R_7$ is hydrogen or alkyl especially methyl, $R_8$ is phenyl or benzoyl which may be unsubstituted or substituted eg 1–3 times by halogen, alkyl and/or alkoxy. The following meanings are preferred independently for each substituent.

A a) meanings a) and b)
  b) phenyl
  c) pyridyl
R a) carboxyl in the form of the free acid or in salt or ester form or carbamoyl or mono- or di-substituted carbamoyl
  b) $COOR_5$ wherein $R_5$ is hydrogen, alkyl, $COO^+Ma^-$ wherein Ma is an alkali metal or ammonium cation or $CONR_7R_8$ wherein $R_7$ is hydrogen or alkyl and $R_8$ is alkyl, aryl or substituted aryl
  c) $COO^-Na^+$, $COOCH_3$, $CONHC_6H_{13}$, $CONH(CH_3)$phenyl, $COO^-H_3N^+iC_3H_7$, $CON(CH_3)_2$, $CONHCH_3$
$Y_1$ a) hydrogen, halogen, alkyl or alkoxy
  b) halogen, especially fluorine or chlorine
$Y_2, Y_3$ a) hydrogen or halogen, alkyl or alkoxy
  b) hydrogen or halogen
  c) chlorine
$W_1$ N
$W_2$ a) CH or N
  b) CH
$W_3$ $CR_3$
$W_4$ N
$W_5$ a) CH or N
  b) N
$W_6$ a) O
  b) NH
Z a) elements selected from methylene, substituted methylene,

b) 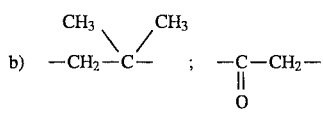

$X_1, X_2$ a) alkoxy, especially methoxy
  b) hydroxy
$X_3$ a) hydrogen
  b) alkoxy especially methoxy
$R_1, R_3$ a) alkoxy, especially methoxy
$R_4$ a) halogen, especially chlorine
  b) alkyl, especially methyl $R_2$ a) alkyl, especially methyl
  b) hydrogen
$R_5$ a) alkyl, alkenyl or alkynyl
  b) $C_{1-4}$alkyl, especially methyl or ethyl
  c) $C_{2-4}$alkenyl
  d) $C_{2-4}$alkynyl, especially propargyl
$R_6, R_7$ a) alkyl
  b) methyl, ethyl
$R_8$ a) hydrogen
  b) alkyl, especially methyl or ethyl
  c) an aryl, especially a phenyl
$R_9, R_{10}$, a) hydrogen or alkyl
$R_{12}, R_{15}, R_{19}$ b) hydrogen or methyl
$R_{11}$ a) alkyl
  b) propyl (n- or iso-)
$Y_4$ a) alkyl or alkoxy
  b) $CH_3$ or $CH_3O$
$R_{13}, R_{14}$ a) hydrogen or halogen
  b) hydrogen or fluorine
$R_{16}$ a) alkyl
  b) $C_{1-4}$alkyl, especially methyl or ethyl
$R_{17}$ a) $S(O)_n$alkyl or $COOR_9$
  b) $SO_2CH_3$ or $COOCH_3$
$R_{18}$ a) hydrogen
$R_{20}$ a) alkyl or phenyl
  b) methyl or phenyl
n a) 2 b) 0
n' a) 2 b) 3
n" a) 1 b) 0
m a) 1 b) 2
X a) hydroxy
  b) hydrogen
  c) taken with Y, =O
  d) acyloxy
  e) alkoxycarbonyloxy
  f) carbamoyloxy
  g) sulphonyloxy
Y a) taken with X, =O
  b) hydrogen
X+R

R' a) alkyl b) alkoxy
R" a) alkyl
  b) methyl
R''' a) alkyl
  b) aryl, especially phenyl
Ring A, Ring B a) at least one contains a heteroatom
  b) ring A=a phenyl or a pyridine ring B=a pyrimidine especially 3,5 dimethoxy pyrimidine Combinations Of the above listed preferred meanings are especially preferred. One such combination comprises compounds of formula (I) in which A is phenyl or pyridyl;
R is a carboxyl group in the form of a free acid, ester or salt; carbamoyl; especially $COOR_5"$ wherein $R_5"$ is $C_{1-5}$alkyl or $C_{2-5}$alkenyl or $CONR_7"R_8"$ wherein $R_7"$ is $C_{1-12}$alkyl, amino, $C_{1-4}$alkylamino, anilino, haloanilino, benzyl, halobenzyl, $C_{1-4}$alkylbenzyl, $C_{1-4}$alkoxybenzyl, phenyl, halophenyl, $C_{1-4}$alkylphenyl or $C_{1-4}$alkoxyphenyl;

$R_8"$ is hydrogen or $C_{1-4}$alkyl;

$Y_1$, $Y_2$ and $Y_3$ are independently hydrogen or halogen;

$W_1$ and $W_4$ are N;

$W_2$ is CH;

$W_3$ is $CR_3$ wherein $R_3$ is $C_{1-5}$alkoxy;

$R_1$ is $C_{1-5}$alkoxy;

X is hydroxyl or $C_{1-4}$alkoxycarbonyloxy or taken with Y is =O;

Y is hydrogen or taken with X is =O; or

X and R together form a bridge having the formula —C(O)O— wherein the carbonyl is attached to A, and Y is hydrogen or $C_{2-8}$acyloxy.

A further group of compounds includes those of formula I wherein X may additionally represent $COOR_5$ as defined above; and/or $R_{15}$ and $R_{16}$ may additionally independently represent halogen, alkylthio, alkoxycarbonyl or optionally substituted carbamoyl; and/or $R_{18}$ may additionally represent optionally substituted aryl.

Further preferred substituent meanings include compounds according to claim 1 wherein A is other than phenyl, naphthyl, pyridyl which may be fused on its (b) or (c) side to benzene, or pyridyl-N-oxide.

Compounds according to claim 1 wherein R is other than formyl, a carboxyl group which may be in the form of the free acid or in ester or salt form, a thiocarboxyl group which may be in the form the free acid or in ester form or the group $CX_1X_2X_3$.

Compounds according to claim 1 wherein R is other than formyl, dimethoxymethyl, $COOR_{30}$ or $COSR_{31}$ wherein $R_{30}$ represents hydrogen, an alkali metal cation, an alkaline earth metal cation, an ammonium cation, an alkylammonium cation, $C_{1-3}$alkyl, $C_{2-3}$haloalkyl, allyl, propargyl, benzyl optionally substituted by halogen, methyl, ethyl, methoxy, ethoxy, trifluoromethyl, methylthio, methylsulfinyl, methylsulfonyl or nitro, $C_{2-4}$alkoxyalkyl, $N=CR_{32}R_{33}$, $CH_2S(O)_tR_{34}$ or $CH(CH_3)S(O)_tR_{34}$ wherein $R_{32}$ is chlorine, methyl, ethyl or methylthio, $R_{33}$ is methyl, ethyl, $COOCH_3$, $COOC_2H_5$ or $C(O)N(CH_3)_2$, $R_{34}$ is methyl, ethyl, propyl, isopropyl or phenyl optionally substituted by halogen, methyl, methoxy or nitro and t is 0, 1 or 2; and $R_{31}$ represents methyl, ethyl or benzyl.

Compounds of formula I wherein A is pyridyl or pyridyl-N-oxide and at least two of $Y_1$, $Y_2$ and $Y_3$ are other than hydrogen.

Compounds of formula I wherein one of $Y_1$, $Y_2$ and $Y_3$ is other than hydrogen, fluorine, chlorine, methyl, methoxy, methylthio, methylsulfinyl or methylsulfonyl.

Compounds of formula I wherein A is phenyl and one of $Y_1$, $Y_2$ and $Y_3$ is other than hydrogen, fluorine, chlorine, methyl, ethyl, methoxy, ethoxy, $C_{2-3}$-alkenyl, $C_{2-3}$alkynyl, $SO_{(t)}CH_3$, $SO_{(t)}C_2H_5$, nitro, phenoxy, $C_{2-4}$alkylcarbonyl, $C(OCH_3)_2CH_3$ or $C(SCH_3)_2CH_3$ and t is 0, 1 or 2.

Compounds of formula I wherein each of $Y_1$, $Y_2$ and $Y_3$ is other than hydrogen.

Compounds of formula I wherein one of $W_1$ and $W_4$ is other than nitrogen.

Compounds of formula I wherein $W_2$ is other than nitrogen or CH.

Compound of formula I wherein $R_1$ is other than methoxy or ethoxy.

Compound of formula I wherein $W_3$ is other than $CR_3$ wherein $R_3$ is methyl, ethyl, methoxy, ethoxy, difluormethoxy, or chlorine.

Compounds of formula I wherein both of X and Y are other than hydrogen.

Compounds of formula I wherein one of X and Y is other than hydrogen, fluorine, chlorine, methyl, hydroxy, cyano, carbamoyl, methylcarbamoyl, dimethylcarbamoyl or $COOR_{35}$, wherein $R_{35}$ is $C_{1-3}$alkyl, $C_{2-5}$haloalkyl, $C_{3-5}$alkenyl, $C_{3-5}$alkynyl, $C_{2-5}$alkoxyalkyl, or benzyl optionally substituted by methyl, methoxy, methylthio, trifluoromethyl, halogen or nitro.

Combinations of these further preferred meanings with each other and with those set out above also deserve mention.

Examples of preferred compounds according to the invention are compound nos. 13, 40, 53, 55, 58, 64, 77, 78, 82, 91, 103, 108, 110, 111, 124, 125, 130, 143, 149, 163, 170, 175, 183, 199, 204, 205, 211, 219, 220, 224, 228, 247, 249, 258, 262, 263, 265, 266, 267, 272, 273, 277, 286, 294, 302, 310, 385, 403, 413, 452, 454, 455, 456, 457, 464, 473, 477, 479, 480, 481, 483, 487, 489, 504, 510, 522, 528, 531, 532, 539, 545, 547, 571, 576, 584, 590, 591, 593, 594, 595,599, 605, 606, 607, 608,612 and 622.

Compounds having the formula

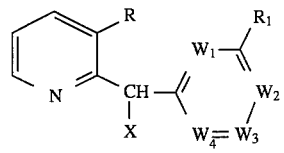

especially those wherein X is CN and at least one of $W_1$ and $W_4$ is nitrogen may exist in the alternate tautomeric form

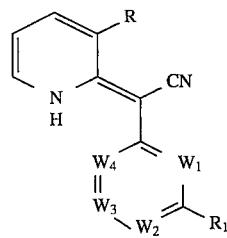

The compounds of formula I according to the invention may be prepared as follows.

a) when X and R combine to form a bridging group as defined above and Y is hydrogen, cyano, arylthio, arylsulfinyl or arylsulfonyl, reacting a compound of formula II

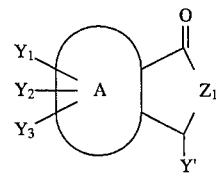

(II)

wherein A is as defined above, Y' represents hydrogen, cyano, arylthio, arylsulfinyl or arylfulfonyl and $Z_1$ represents oxygen, sulfur or $NR_2$ wherein $R_2$ is as defined above except for hydrogen, with a compound of formula III

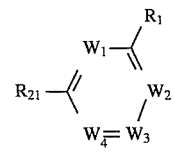

(III)

wherein $W_1$, $W_2$, $W_3$, $W_4$ are as defined above except that at least one of $W_1$ and $W_4$ is nitrogen and $R_{21}$ represents methylsulfonyl, or halogen to obtain the corresponding compound of formula Ip

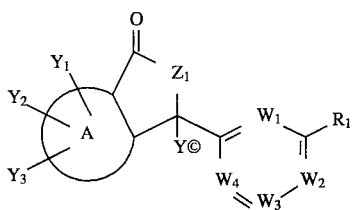

b) treating a compound of formula Ip wherein Y' represents cyano or arylsulfonyl and Z' represents oxygen and the other symbols are as defined above.
  (i) by hydrolysis to give a corresponding compound of formula I wherein R and X form a bridge and Y is hydroxy or a compound of formula I wherein X and Y together form =O
  (ii) with an amine to give a corresponding compound of formula I wherein R is an optionally substituted carbamoyl group and X and Y together form =O
  (iii) with a group $MOR_{22}$ wherein M an alkali metal and $R_{22}$ is alkyl, to give a corresponding compound wherein R and X form a bridge and Y is alkoxy c) hydrolyzing a compound of formula Ip wherein Y' represents hydrogen and $Z_1$ represents oxygen to give a compound of formula I wherein R is a carboxyl group optionally in salt form, X is hydrogen and Y is hydroxy d) ring opening a compound of formula Ip wherein Y' represents hydroxy and $Z_1$ represents oxygen to give a compound of formula I wherein R is a carboxyl group optionally in salt form and X and Y together are =O e) esterifying a compound of formula I wherein R is a carboxyl group optionally in salt form and X and Y are =O to give the corresponding compound wherein R is a carboxyl group in ester form f) halogenating a compound of formula Ip wherein Y' represents hydroxy to give a compound of formula I wherein X and R together form a bridging group and Y' is halogen g) reacting a compound of formula Ip wherein $Z_1$ is oxygen and halogen rich a group $R_2NH_2$ and a group $HOR_{23}$ wherein $R_{23}$ represents alkyl, acyl or aryl and $R_2$ is as defined above to give the corresponding compound wherein $Z_1$ is $NR_2$ and Y' is alkoxy, aryloxy or acyloxy h) oxidizing a compound of formula Ip wherein Y' represents hydrogen give the corresponding compound wherein Y' represents hydroxy i) reacting a compound of formula IV

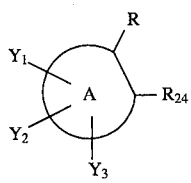

with a compound of formula V

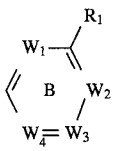

to produce a compound of formula Iq

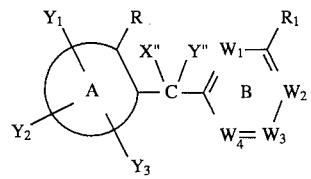

wherein A, R, $R_1$, $W_1$, $W_2$, $W_3$, $W_4$, $Y_1$, $Y_2$ and $Y_3$ are as defined above and X" and Y" are hydrogen and $R_{24}$ is alkyl, especially methyl, cyanomethyl, alkoxycarbonylmethyl, carbamoylmethyl, j) mono- or di- halogenating a compound of formula Iq wherein X" and Y" are hydrogen to produce the corresponding compound of formula Iq wherein one or both of X" and Y" are halogen k) oxidizing a compound of formula Iq wherein X" and Y" are both hydrogen or X" is halogen and Y" is hydrogen to produce the corresponding compound wherein X" and Y" together represent =O or one represents hydrogen and the other represents hydroxy l) alkylating a compound of formula Iq wherein X" represents hydrogen and Y" represents hydrogen to produce the corresponding compound wherein X" represents alkyl and Y" represents hydrogen m) introducing an alkoxy or alkylthio group into a compound of formula Iq wherein X" represents halogen and Y" represents hydrogen to produce the corresponding compound wherein X" represents alkoxy or alkylthio and Y" represents hydrogen n) acylating a compound of formula Iq wherein X" represents hydroxy and Y represents hydrogen to produce the corresponding compound wherein X" represents acyloxy and Y" represents hydrogen o) reacting a compound of formula Ip wherein $Z_1$ is oxygen and Y' is hydrogen with a group $R_7NH_2$ wherein $R_7$ is as defined above to give a compound of formula I wherein R is monosubstituted carbamoyl, X is hydrogen and Y is hydroxy p) sulfonylating, carbamoylating, acylating or carbalkoxylating a compound of formula Ip wherein $Z_1$ is oxygen and Y' is hydroxy to produce the corresponding compound of formula Ip wherein Y' represents sulfonyloxy, carbamoyloxy, acyloxy or alkoxycarbonyloxy q) reacting a compound of formula Ip wherein $Z_1$ is oxygen and Y' is halogen with a group $R_7R_8NH$ wherein $R_7$ and $R_8$ are as defined above ($R_7$ and $R_8$ ≠H) to give a compound of formula I wherein R is disubstituted carbamoyl, and X and Y together represent =O.

r) oxidizing a compound of formula

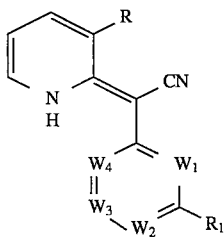

to give a corresponding compound of formula I wherein X and Y together represent =O.

s) reacting a compound of formula III with a compound of formula IV each as defined above to produce a compound of formula Iq wherein X" and Y" are hydrogen.

t) oxidizing a compound of formula I wherein X=Y=H to give a compound Ip wherein $Z_1$ is oxygen and Y' is hydroxy.

u) reacting a compound of formula V

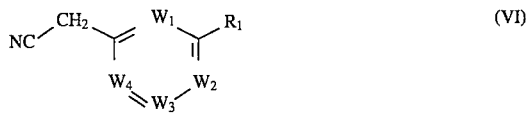

with a compound of formula IV wherein R is cyano and $R_{24}$ is halogen and oxidizing the product to give a compound of formula I where R is cyano and X and Y together represent =O or of formula Ip wherein $Z_1$ represents =O and $Y^1$ is cyano.

and in each case recovering any compound wherein R is a carboxyl or thiocarboxyl group in free form or in ester form and any compound wherein R is carboxyl in free form or in salt form.

The following table is illustrative of suitable reaction conditions.

| | | REACTION CONDITIONS | | |
|---|---|---|---|---|
| | Reaction Reagents | Solvents | Temperature | Others |
| a) | 1) a) base eg LDA<br>or b) base eg NaH<br>2) III | 1) and 2) inert eg DMF,<br>ether, cyclic ether eg THF<br>1) and 2) inert eg DMF,<br>ether, cyclic ether eg THF | a) reduced eg −70°<br>b) R.T. | |
| b) | i)1) base eg NaOH<br>2) acidify | inert eg ether,<br>cyclic ether eg THF or<br>alcohol eg methanol | R.T. | |
| b) | ii) 1) amine | inert eg ether, cyclic<br>ether eg THF | | |
| b) | iii) $MOR_{22}$ | alcohol eg methanol,<br>cyclic ether eg THF | | |
| c) | base eg LiOH | water optionally with an alcohol<br>or cyclic ether eg THF | R.T. | |
| d) | base eg NaOH | as c) | R.T. | |
| e) | halide eg $IR_5$<br>base eg $K_2CO_3$, NaH | inert eg DMF,<br>2-butanone (MEK) | elevated eg<br>50–80° | |
| f) | halogenating<br>agent eg $SOCl_2$, DMF | inert eg chlorinated<br>hydrocarbon eg $CCl_4$ $CH_2Cl_2$ | elevated eg<br>40–80° | |
| g) | 1)$R_7NH_{22}$; $R_{23}OH$ | as f) | elevated eg<br>50–80° | |
| h) | 1) oxidizing agent<br>eg NaOCl<br>2) base eg NaOH<br>3) acid eg HCl | 1), 2) and 3) inert eg<br>$H_2O$ optionally with alcohol<br>eg methanol<br>cyclic ether eg THF | elevated eg 50°<br>R.T.<br>R.T. | |
| i) | 1) base eg LDA<br><br>2) AcOH<br>3) DDQ<br>4) aq NaOH | 1) anhyd. inert eg ether such<br>as cyclic ether eg THF<br>2), 3) and 4) ether, $H_2O$ | reduced eg −30°<br><br>R.T.<br>reduced eg 0°<br>elevated eg 75° | |
| j) | NBS, benzoylperoxide | inert eg halogenated<br>hydrocarbon such as $CCl_4$ | elevated eg 75° | |
| k) | A. when X" = halogen and<br>Y" = H to give X + Y are = O<br>DMSO, $Na_2CO_3$<br>B. when X" and Y" = H<br>to give X" + Y" are = O<br>a) $SeO_2$<br>b) t-butylhydro-<br>peroxide<br>$Co_2(CO)_8$<br>c) 1) Mn $(OAc)_3$<br>2) $H_2O$<br>C. when X" and Y" = H<br>to give X" = OH, Y" = H<br>i) nBuLi<br>ii) t-butyl peroxybenzoate<br>iii) $BF_3.MeOH$ | DMSO<br><br><br>AcOH<br><br><br>$CH_3CN$<br><br><br>AcOH<br><br><br><br>THF<br>THF<br>toluene | elevated eg 50–60°<br><br><br>110°, 1 hr; or<br><br><br>85°; or<br><br><br>25→100°<br><br><br><br>−78°<br>−78°→20°<br>40°→100° | |
| l) | base eg NaH, alkyl | inert eg ether, THF | 0°→R.T. | |

-continued

| | | REACTION CONDITIONS | | |
|---|---|---|---|---|
| Reaction Reagents | | Solvents | Temperature | Others |
| | halide | | | |
| m) | $MOR_{22}$, $MSR_{22}$ eg $NaOCH_3$ | inert eg DMF, alcohol | R.T.→50° | |
| n) | acyl chloride eg $CH_3\overset{O}{C}Cl$ or anhydride eg $Ac_2O$; amine eg triethylamine | inert eg ether, THF pyridine | R.T.→30° | |
| o) | amine, eg α-methyl benzylamine or | alcohol eg methanol | R.T.→80° | |
| | amine, eg aniline, $CH_3SO_2NH_2$; $Me_3Al$ (catalyst) | inert eg toluene $CH_2Cl_2$ | R.T. | |
| p) | acylchloride eg acetyl-chloride, ethylchloro-formate or anhydride; amine eg DMAP, triethylamine or | inert eg ether THF, pyridine | R.T. | |
| | isocyanate eg methylisocyanate; amine eg triethylamine or | inert eg ether THF, pyridine | " | |
| | sulfonyl chloride eg methyl-sulfonyl chloride; amine eg triethylamine | inert eg ether THF, pyridine | " | |
| q) | $R_7R_8NH$, triethylamine, DMAP | inert eg $CH_2Cl_2$ | " | |
| r) | i) m-chloroperbenzoic acid ii) base eg NaOH | inert eg $CH_2Cl_2$ inert eg cyclic ether | 20°, 30 min 20°, 30 min | |
| s | 1) LDA 2) III | THF THF | −78° −78°→20° | |
| t) | $KMnO_4$ | $H_2O$ | 100° C. | |
| u) | i) base eg $K_2CO_3$, $KOBu^t$, NaH | inert eg DMF, THF | RT→100° C. | |
| | ii) oxidizing agent eg NaOCl or $H_2O_2$/AcOH | water optionally with inert eg cyclic ether or $CH_3CN$ | RT | |

Processes a) through u) also form part of the invention.

The starting materials of formula II or III are either known or may be prepared analogously to known methods.

The compounds of formula I have herbicidal activity as observed after their pre-emergent or post-emergent application to weeds or a weed locus.

The term "herbicide" (or "herbicidal") refers to an active ingredient (or an effect) which modifies the growth of plants because of plant growth regulating or phytotoxic properties so as to retard the growth of the plant or damage the plant sufficiently to kill it.

Application of a compound of formula I is made according to conventional procedure to the weeds or their locus using a herbicidally effective amount of the compound, usually from 10 g to 10 kg/ha.

Compounds according to the invention may be used in the control of both broad-leaf and grassy weeds on both pre- and post-emergent application. Compounds may also exhibit selectivity in various crops and are thus suited for use in weed control in crops such as corn, cotton, wheat, soybean and rice.

The optimum usage of a compound of formula I is readily determined by one of ordinary skill in the art using routine testing such as greenhouse testing and small plot testing. It will depend on the compound employed, the desired effect (a phytotoxic effect requiring a higher rate than a plant growth regulating effect), the conditions of treatment and the like. In general satisfactory phytotoxic effects are obtained when the compound of formula I is applied at a rate in the range of from 0.01 to 5.0 kg, more preferably of from 0.05 to 2.5 kg per hectare, eg 0.05 to 5.0 kg per hectare, especially 0.1 to 2.5 kg per hectare.

The compounds of formula I may be advantageously combined with other herbicides for broadspectrum weed control. Examples of herbicides which can be combined with a compound of the present invention include those selected from the carbamates, thiocarbamates, chloroacetamides, dinitroanilines, benzoic acids, glycerol ethers, pyridazinones, semicarbazones, uracils and ureas for controlling a broad spectrum of weeds.

The compounds of formula I are conveniently employed as herbicidal compositions in association with agriculturally acceptable diluents. Such compositions also form part of the present invention. They may contain, aside from a compound of formula I as active agent, other active agents, such as herbicides or compounds having antidotal, fungicidal, insecticidal or insect attractant activity. They may be employed in either solid or liquid forms eg in the form of a wettable powder or an emulsifiable concentrate incorporating conventional diluents. Such compositions may be produced in conventional manner, eg by mixing the active ingredient with a diluent and optionally other formulating ingredients such as surfactants.

Agriculturally acceptable additives may be employed in herbicidal compositions to improve the performance of the active ingredient and to reduce foaming, caking and corrosion, for example.

The term "diluent" as used herein means any liquid or solid agriculturally acceptable material which may be added to the active constituent to bring it in an easier or improved applicable form, respectively, to a usable or desirable strength of activity. It can for example be talc, kaolin, diatomaceous earth, xylene or water.

"Surfactant" as used herein means an agriculturally acceptable material which imparts emulsifiability, spreading, wetting, dispersibility or other surface-modifying properties. Examples of surfactants are sodium lignin sulfonate and lauryl sulfate.

Particularly formulations to be applied in spraying forms such as water dispersible concentrates or wettable powders may contain surfactants such as wetting and dispersing agents, for example the condensation product of formaldehyde with naphthylene sulphonate, an ethoxylated alkylphenol and an ethoxylated fatty alcohol.

In general, the formulations include from 0.01 to 90% by weight of active agent and from 0 to 20% by weight of agriculturally acceptable surfactant, the active agent consisting either of at least one compound of formula I or mixtures thereof with other active agents. Concentrate forms of compositions generally contain between about 2 and 90%, preferably between about 5 and 70% by weight of active agent. Application forms of formulation may for example contain from 0.01 to 20% by weight of active agent.

Typical herbicidal compositions, according to this invention, are illustrated by the following Examples A, B and C in which the quantities are in parts by weight.

EXAMPLE A

Preparation of a Dust

10 Parts of a compound according to this invention and 90 parts of powdered talc are mixed in a mechanical grinder-blender and are ground until a homogeneous, free-flowing dust of the desired particle size is obtained. This dust is suitable for direct application to the site of the weed infestation.

EXAMPLE B

Preparation of a Wettable Powder

25 Parts of a compound according to this invention are mixed and milled with 25 parts of synthetic fine silica, 2 parts of sodium lauryl sulphate, 3 parts of sodium ligninsulphonate and 45 parts of finely divided kaolin until the mean particle size is about 5 micron. The resulting wettable powder is diluted with water before use to a spray liquor with the desired concentration.

EXAMPLE C

Preparation of Emulsifiable Concentrate (EC)

13.37 Parts of a compound according to this invention are mixed in a beaker with 1.43 parts of Toximul 360A (a mixture of anionic and non-ionic surfactants containing largely anionic surfactants), 5.61 parts of Toximul 360A (a mixture of anionic and non-ionic surfactants containing largely nonionic surfactants), 23.79 parts of dimethylformamide and 55.8 parts of Tenneco 500–100 (predominantly a mixture of alkylated aromatics such as xylene and ethylbenzene) until solution is effected. The resulting EC is diluted with water for use.

The following examples are provided to illustrate the practice of the present invention. Temperature is given in degrees Celsius. Abbreviations used in this specification.

THF=tetrahydrofuran
LDA=lithium diisopropylamide
RT=room temperature
DMF=dimethylformamide
DDQ=2,3-dichloro-5,6-dicyanobenzoquinone
NBS=N-bromosuccinimide
DMSO=Dimethylsulfoxide
MEK=Methylethylketone
DMAP=4-Dimethylaminopyridine Individual alkyl substituents listed in the following tables from A to F are in the "n" isomeric form unless otherwise indicated.

EXAMPLE 1

7-chloro-3-(4,6-dimethoxy-2-pyrimidinyl)phthalide (Table A, cpd. no. 6)

1.68 g (0.01 mol) of 7-chlorophthalide is added to 100 ml of dry THF and the mixture cooled to −70° C. 6.8 ml (0.01 mol) of 1.5M LDA is then added over 3 minutes and the reaction mixture stirred at −70° C. for 15 minutes. 2.18 g (0.01 mol) of 2-methylsulfonyl-4,6-dimethoxypyrimidine in 50 ml of THF is then added and the mixture stirred for 4 hrs with temperature being maintained at −75° to −70° C. The reaction mixture is neutralized with 1.5 g of $NH_4Cl$ in 5 ml of water, warmed and concentrated on a rotovaporator. The concentrate is partitioned between $CH_2Cl_2/H_2O$ (50 ml each) and the aqueous phase separated and treated with further 30 ml of $CH_2Cl_2$. The combined $CH_2Cl_2$ phases are washed with 30 ml of water, separated and concentrated. The concentrate was flash chromatographed on silica gel using 80/20 hexane/ethyl acetate (500 ml), 50/50 hexane/ethyl acetate (500 ml) and 80/20 acetone/methanol (500 ml) (30 fractions X 50 ml). The title compound (fractions 9–23) was obtained after recrystalization from hexane/$CH_2Cl_2$ as a white solid, m.p. 148°–149° C.

EXAMPLE 2

5-(4,6-dimethoxy-2-pyrimidinyl)-furo[3,4-b]pyridine-7(5H)-one (Table B, cpd. no. 40)

A solution of 1.3 g (0.0096 mols) of furo [3,4-b]pyridine-7(5H)-one in 50 ml of dry THF is cooled to −75° C. and 8 ml (0.0192 mols) of 2.5M LDA added dropwise over 5 minutes. The mixture is allowed to react for 1 hr at −75° C. and 2.1 g (0.0096 mol) of 2-methylsulfonyl-4,6-dimethoxypyrimidine in 30 ml of dry THF added dropwise over 10 minutes. The mixture is allowed to warm to RT, 1.6 ml of HCl added and the THF evaporated off. The residue is dissolved in 75 ml of $CH_2Cl_2$, washed with water (2×50 ml) and the organic phase concentrated to give a yellowish white gummy solid. This is chromatographed on a silica gel column using 50/50 hexane/ethyl acetate (500 ml), ethyl acetate (500 ml) and 80/20 acetone/methanol (1000 ml) (30 fractions). The crystalline residue (fractions 18–21) of the title product has m.p. of 167°– 168° C.

EXAMPLE 3

7-chloro-3-methoxy-3-(4,6-dimethoxy-2-pyrimidinyl)-2-methyl-isoindol- 1(3H)-one (Table C, cpd. no. 54)

A mixture of 0.5 g of 7-chloro-3-hydroxy-3-(4,6-dimethoxy-2-pyrimidinyl)phthalide, 30 ml of $CCl_4$, 2 ml of $SOCl_2$ and 4 drops of DMF is heated at 65° C. for 1½ hrs, cooled and excess $SOCl_2$ and $CCl_4$ removed on a rotovaporator. The residue is diluted with 20 ml of $CH_2Cl_2$ and added to a mixture of 5 ml of 40% aq methylamine and 10 ml of methanol with stirring over ½ hr. The mixture is placed on

EXAMPLE 4

7-chloro-3-hydroxy-3-(4,6-dimethoxy-2-pyrimidinyl) phthalide (Table A, cpd. no. 13)

A mixture of 1.8 g of 7-chloro-3-cyano-3-(4,6-dimethoxy-2-pyrimidinyl)phthalide, 50 ml of 1% NaOH and 50 ml of THF are stirred at room temperature for 3 hrs. The THF is removed by evaporation and the mixture is diluted with water and extracted twice with ethyl acetate. The aqueous solution is acidified with $2N-H_2SO_4$. The resulting acid solution is extracted with 3×100 ml ethyl acetate and the organic phases combined, dried over $Na_2SO_4$ and concentrated to give a pale yellow solid. This residue is taken up in ethyl acetate and treated with activated charcoal until the yellow base line material is removed to give the title product as a white solid m.p. 188°–190° C.

EXAMPLE 5

7-chloro-3-methoxy-3-(4,6-dimethoxy-2-pyrimidinyl) phthalide (Table A, cpd. no. 30)

1.0 g of 7-chloro-3-cyano-3-(4,6-dimethoxy-2-pyrimidinyl)phthalide is slurried in 20 ml of methanol and the solution cooled with ice and 0.6 ml of sodium methoxide added dropwise. After stirring for 10 min a further 1 ml of sodium methoxide is added and stirring continued for 10 min and the mixture is then quenched with $2N\ H_2SO_4$. Methanol is removed on a rotovaporator and the residue partitioned between water and ethyl acetate. The organic phase is dried over $Na_2SO_4$ and concentrated. Flash chromatography of the residue over silica gel using 25% ethyl acetate/hexane yields a white solid m.p. 180°– 183° C.

EXAMPLE 6 a) Methyl 2-chloro-6-(4,6-dimethoxy-2-pyrimidinylcarbonyl) benzoate (Table C, cpd. no. 55), and b) 7-chloro-3-chloro-(4,6-dimethoxy-2-pyrimidinyl) phthalide (Table A, cpd. no. 21)

A mixture of 0.7 g of 7-chloro-3-hydroxy-3-(4,6-dimethoxy-2-pyrimidinyl)phthalide, 30 ml of $CCl_4$, 2 ml of $SOCl_2$ and 4 drops of DMF are refluxed at 60° for 1½ hrs. The mixture is then cooled, excess $SOCl_2$ and $CCl_4$ removed on a rotovaporator. The residue is diluted with 20 ml of $CH_2Cl_2$ and added to a stirred mixture of 10 ml of methanol and 2 ml of diethylamine. After 2½ hrs the mixture is stripped on a rotovaporator to remove excess $CH_2Cl_2$ and methanol and the residue partitioned between $CH_2Cl_2$ (50 ml) and water (50 ml). The organic phase is separated, concentrated and the gummy residue flash chromatographed over silica gel using 80/20 hexane/ethyl acetate (500 ml), 60/40 hexane/ethyl acetate (500 ml) (28 fractions X 50 ml). Fractions 18 to 20 yielded title compound a) and fractions 11 to 16 the compound b).

EXAMPLE 7

7-chloro-3-cyano-3-(4,6-dimethoxy-2-pyrimidinyl) phthalide (Table A, cpd. no. 27)

600 mg of 7-chloro-3-cyanophthalide are added to an ice-cold suspension of hexane washed 60% NaH (160 mg) in DMF (20 ml). After 15 min, 710 mg of 2-methylsulfonyl-4,6-dimethoxypyrimidine are added. After stirring at RT for 1½ hr the mixture is poured onto 200 ml of ice/water acidified with $2N\ H_2SO_4$ and stirred. The precipitate is filtered and dried in a vacuum oven to yield the title product, m.p. 159°–161° C.

EXAMPLE 8

7-chloro-3,3-bis(4,6-dimethoxy-1,3,5-triazin-2-yl) phthalide (Table A, cpd. no. 36)

1.48 g of 7-chlorophthalide are dissolved in 80 ml of THF. The solution is cooled to −70° C. and 1.5M LDA in THF (6 ml) is syringed in at −70° C. over 3 min. Stirring is continued for 15 min at −70°, 1.54 g of 2-chloro-4,6-dimethoxy-1,3,5-triazine in 50 ml of THF added dropwise and the mixture is then allowed to warm to −20°. The mixture is again cooled to −70° and 1 ml of conc. HCl in 10 ml of water is added. The mixture is stirred for 25 min and allowed to warm to RT and the THF is removed by evaporation. The residue is partitioned between $CH_2Cl_2$ and water (50 ml each) and the aqueous phase extracted with an additional 30 ml of $CH_2Cl_2$. The combined organic phases are washed with 30 ml of water and concentrated to give a yellow gum. This is flash chromatographed on silica gel using 60/40 hexane/ethyl acetate (1000 ml), ethyl acetate (400 ml), 80/20 acetone/methanol (500 ml) (30 fractions X 50 ml, 1 X 200 ml). Fractions 21 and 22 yielded a yellow gum which upon recrystalization from hexane yielded title product m.p. 126°–127° as a yellow solid.

EXAMPLE 9

Lithium 2-chloro-6-(4,6-dimethoxy-e-hydroxy-2-pyrimidinylmethyl)benzoate (Table C, cpd. no. 53)

A mixture of 1.0 g of 7-chloro-3-(4,6-dimethoxy-2-pyrimidinyl)phthalide, 0.136 g of $LiOH.H_2O$, 2 ml of water and 10 ml of methanol is stirred overnight at RT. The mixture is evaporated to dryness on a rotovaporator. Further drying in a drying pistol yield the title compound as a white solid, m.p. 153°–157° C.

EXAMPLE 10

Lithium 3-[(4,6-dimethoxy-α-hydroxy-2-pyrimidinyl)methyl]pyridine-2-carboxylate (Table E, cpd. no. 64)

A mixture of 0.490 g of 5-(4,6-dimethoxy-2-pyrimidinyl)furo [3,4,b] -pyridine-7(5H)-one, 0.0768 gm of LiOH.H$_2$O, 10 ml of methanol and 2 ml of water is stirred for 24 hrs under nitrogen at RT and the solvent stripped off. The yellowish solid is dried for a further 2 hrs to yield the title product, m.p.> 250° C. (decomp.).

EXAMPLE 11

Sodium 2-chloro-6-[(4,6-dimethoxy-2-pyrimidinyl)carbonyl]benzoate (Table C, cpd. no. 58)

1.24 g of 7-chloro-3-hydroxy-3-(4,6-dimethoxy-2-pyrimidinyl)phthalide, 154 mg NaOH, 25 ml THF and 25 ml water are mixed until a yellow homogenous solution is achieved. The solvents are stripped on a rotovaporator and then on a Kugelrohr at 100° C. to produce the title compound as a yellow solid, m.p. 276°–278° C.

EXAMPLE 12

3-[(4,6-dimethoxy-2-pyrimidinyl)carbonyl]-pyridine-2-carboxylic acid (Table E, cpd. no. 63)

490 mg of 5-(4,6-dimethoxy-2-pyrimidinyl)-furo[3,4-b]pyridine-7(5H)-one is dissolved in 50 ml of methanol and the mixture heated with stirring at 50° C. until a homogenous solution is formed (ca ½ hr). 2.6 g of NaOCl is added dropwise and the solution heated for a further ½ hr at 55° C. 0.208 g of 50% NaOH is added at 55° and the mixture heated for a further ½ hr at this temperature and then cooled in an ice-bath and acidified with 1 ml conc. HCl. The solvent is evaporated and the residue partitioned between 50 ml of CH$_2$Cl$_2$ and 50 ml of water. The organic phase is concentrated to give a white solid, m.p. 71°–73°.

EXAMPLE 13

2-[(4,6-dimethoxy-2-pyrimidinyl)-α-iminomethyl]benzoic acid (Table C, cpd. no. 51)

2.67 g of isopropyl 2-bromobenzoate are dissolved in 100 ml of dry diethylether, the solution cooled to -100° C. and 6.6 ml of 1.6M n-butyllithium solution added. Stirring is continued for 10 min and 12 g of 2-cyano- 4,6-dimethoxypyrimidine in 60 ml of diethylether is added over 2 min at –100° C. The mixture is stirred for ½ hr at –80° and then allowed to warm to RT. 3 g of NH$_4$Cl in 30 ml of water is added to the reaction mixture, cooled in an ice-bath. The ether layer is separated off, washed with water (2×30 ml) and concentrated. The gummy residue is dissolved in 20 ml of 85/15 hexane/ethyl acetate, and CH$_2$Cl$_2$, and flash chromatographed on silica gel using 800 ml 85/15 hexane/ethyl acetate, 500 ml 1% methanol in ethyl acetate, 500 ml 5% methanol in ethyl acetate and 500 ml of 80/20 acetone/methanol (40 fractions at 50 ml; 1 at 200 ml). Fractions 7 to 10 yielded title compound which on recrystallization from CH$_2$Cl$_2$ melted at 225°–235° C.

EXAMPLE 24

5—Chloro-5-(4,6-dimethoxy-2-pyrimidinyl)furo [3,4-b]pyridine-7(5H)-one (Table B, cpd. no. 68)

A mixture of 490 mg of 5-(4,6-dimethoxy-2-pyrimidinyl)furo[3,4,b] pyridine-7(5H)one and 50 ml of methanol is heated at 55° for ½ hour or until a homogenous solution is formed. 2.6 g of NaOCl (common house bleach) is added dropwise. The mixture is taken up in dichloromethane an the organic phase separated and evaporated to dryness to yield the title compound, mp 146°– 148° C.

EXAMPLE 15

3-[(4,6-dimethoxy-2-pyrimidinyl)carbonyl]-pyridine-2-carboxylic acid (Table E, cpd. no. 63)

0.208 g of 50% NaOH is added at 55° to a solution of 0.551 g of 5 -chloro-5-(4,6-dimethoxy-2-pyrimidinyl)-furo [3,4,b]pyridine (Table B, cpd. no. 68) in 50 ml methanol. The mixture stirred for a further ½ hr at 55°, cooled in an ice-bath, acidified with 1 ml of concentrated HCl and the solvent evaporated. The residue is partitioned between 50 ml of CH$_2$Cl$_2$ and 50 ml H$_2$O and the CH$_2$Cl$_2$ layer concentrated to give 0.39 g of the title product as a white solid, m.p. 71°–73° C.

EXAMPLE 16

2-(2-(4,4-dimethyl-oxazolin-2-yl)-benzyl)-4,6-dichloropyrimidine (Table C, cpd. no. 61)

To a mixture of 1.25 g of 2-o-tolyl-4,4-dimethyl-oxazoline in 20 ml of ether under N$_2$ atmosphere at –30° C. is added by syringe 4.2 ml of 1.6M n-butyllithium in hexane with stirring which is continued for 1 hr at –10° C. 0.98 g of 4,6-dichloropyrimidine in 20 ml of ether are added slowly to the reaction mixture which is then stirred at –45° to –30° C. for 30 min and at 0° C. for a further 30 min. The reaction mixture is quenched with acetic acid (0.4 ml) and water (0.1 ml) in THF (1.3 ml) and then treated with 1.5 g of 2,3-dichloro-5,6-dicyanobenzoquinone (DDQ) in 6 ml of THF. The temperature is brought to RT and the mixture stirred for 5 min after cooling to 0° C. 7.6 ml of 1N NaOH (cooled) are added and the mixture stirred for 5 min. The organic phase is separated and dried over Na$_2$SO$_4$ filtered and the solvent removed. Following chromatography (10/90 ether/hexane) the title product is obtained.

EXAMPLE 17

2-(2-(4,4-dimethyl-oxazolin-2-yl)-benzyl)-4,6-dimethoxypyrimidine (Table C, cpd. no. 48)

To a solution of 1.7 g of 2(2-(4,4-dimethyl-oxazolin-2-yl)-benzyl)-4,6-dichloropyrimidine in 100 ml of methanol are added 2.18 g of 25% methanolic NaOCH$_3$ and the mixture heated for 10 hrs at 65° C. with stirring. The temperature is lowered to 60° and stirring continued overnight. The solvent is stripped and the residue taken up in 80 ml of toluene and 50 ml of water. The toluene layer was separated and washed with 50 ml of water, separated and concentrated to give the title compound as a yellow oil.

EXAMPLE 18

2-(2-(4,4-dimethyl-oxazolin-2-yl)-α-bromobenzyl)-4,6-dimethoxy pyrimidine (Table C, cpd. no. 62)

0.55 g of 2-(2-(4,4-dimethyl-oxazolin-2-yl)-benzyl)-4,6-dimethoxypyrimidine, 0.30 g of a N-bromosuccinimide, 0.03 g of benzoyl peroxide are dissolved in 60 ml of CCl$_4$ and heated under reflux overnight at 75° C. The reaction mixture is filtered and the filtrate washed with 5% NaHCO$_3$ solution (50 ml), 50 ml of water and the organic phase separated and concentrated to give the title compound.

EXAMPLE 19

2-(2-(4,4-dimethyl-oxazolin-2-yl)-benzoyl)4,6-dimethoxypyrimidine (Table C, cpd. no. 49)

A mixture of 1.2 g of 2-(2-(4,4-dimethyl-oxazolin-2-yl)-α-bromobenzyl)- 4,6-dimethoxy-pyrimidine and 2 g of Na$_2$CO$_3$ in 30 ml of DMSO is heated with stirring at 50°–60° C. for 3 hrs. The mixture is poured into 150 ml of water and extracted with toluene. The toluene extract is washed twice with water (2×50 ml) separated and concentrated. The thus obtained gum is chromatographed with 800 ml of 80/20 hexane/ethyl acetate, 500 ml 70/30 hexane/ethyl acetate, 60/40 ml hexane/ethyl acetate (50 ml fractions) fractions 29 to 34 yielded the title compound.

EXAMPLE 20

2-chloro-6-(4,6-dimethoxy-2-pyrimidinylcarbonyl)-benzoic acid dimethylamide (Table C, cpd. no. 57)

1.0 g of 7-chloro-3-cyano-3-(4,6-dimethoxy-2-pyrimidinyl) phthalide is dissolved in 15 ml of THF. 0.7 ml of a 40% aqueous dimethylamine solution is then added via syringe whereupon the solution darkens. Stirring is continued at R.T. for 15 minutes and the mixture diluted with water and partitioned between ethyl acetate and water. The organic phase is separated, washed with 2N H$_2$SO$_4$, then brine, dried and concentrated. The residue is purified on silica gel, eluant 200 ml of 50% ethyl acetate/hexane then 100% ethyl acetate. Fractions 12 to 15 yielded the title compound, m.p. 141°–142° C.

EXAMPLE 21

3-acetoxy-7-chloro-3-(4,6-dimethyloxy-2-pyrimidinyl)phthalide (Table A, cpd. no. 125)

1.1 g of 7-chloro-3-(4,6-dimethoxy-2-pyrimidinyl)-3-hydroxy-phthalide is dissolved in 20 ml of pyridine and 0.3 ml of acetic anhydride added with stirring. After stirring for 20 min the mixture is poured into 2N HCl and extracted with two portions of ethyl acetate. The combined ethyl acetate extracts are washed once with 2N HCl, once with H$_2$O and once with brine and dried over magnesium sulfate. Filtration and evaporation produced the title compound as a white solid, m.p. 213°–215°.

EXAMPLE 22

3-[(4,6-dimethoxy-α-hydroxy-2-pyrimidinyl)methyl] pyridine-2-carboxamide (Table E, cpd. no. 82)

To a solution of 0.9 g of ammonia, in 15 ml of methanol, is added 0.5 g of 3[(4,6-dimethoxy-2-pyrimidinyl)-7-azaphthalide. After stirring for 2 hrs at RT, the methanol is removed under reduced pressure and the concentrate recrystallized from toluene to give the title compound as a white solid, m.p. 135°–137° C.

EXAMPLE 23

3[(4,6-dimethoxy-2-hydroxy-2-pyrimidinyl)methyl] pyridine-2-[carboxy-(4 -isopropyl)anilide]

(Table E, cpd. no. 183)

To a solution of 3 ml of 4-isopropylaniline in 50 ml of toluene is syringed in 4 ml of 15.6% trimethylaluminum in hexane at RT. The mixture is stirred for 0.5 hr at RT and 0.5 g of 3-[(4,6-dimethoxy-2-pyrimidinyl)-7-azaphthalide is added. The mixture is stirred for 2 hrs at RT and acidified with 30 ml of 10% hydrochloric acid at 5°–10° C. The toluene solution is separated, washed with 20 ml of 10% hydrochloric acid, 20 ml of 5% sodium carbonate and 20 ml of water, dried and concentrated. The concentrate is recrystallized from hexane to yield the title compound as a white solid, m.p. 113°–114° C.

3-[(4,6-dimethoxy-α-(ethoxycarbonyloxy)-2-pyrimidinyl)methyl]-pyridine- 2-carboxamide (Table E, cpd. no. 129)

To a solution of 0.5 g of 3-[(4,6-dimethoxy-α-hydroxy-2-pyrimidinyl)methyl] pyridine-2-carboxamide, 0.05 g of 4-(dimethylamino)pyridine, and 1 ml of triethylamine, in 20 ml of toluene and 10 ml of dichloromethane is added 1 ml of ethyl chloroformate at RT. After stirring for 1 hr at ambient temperature, the mixture is washed with water (2×30 ml), dried and concentrated on a rotoevaporator. The concentrate is digested with 1/1 mixture of hexane-toluene, 10 ml, at 50° C., cooled to RT and filtered to isolate 0.45 g of the title compound as a yellow solid, m.p. 112°–114° C.

EXAMPLE 25

3-[(4,6-dimethoxy-α-benzoyloxy-2-pyrimidinyl) methyl]pyridine-2 -(N,N-dibenzoyl)carboxamide (Table E, cpd. no. 159)

To a solution of 0.05 g of 3-[(4,6-dimethoxy-α-hydroxy-2pyrimidinyl)methyl] -2-carboxamide, 0.5 g, 4-(dimethylamino)pyridine and 4 ml of triethylamine in 30 ml of dichloromethane is added 1.4 g of benzoyl chloride at RT in two portions. The reaction mixture is stirred at RT for 17 hrs and washed with 30 ml of water, 30 ml of 5% hydrochloric acid and 30 ml of water. The dichloromethane solution is concentrated and the concentrate flash chromatographed through 300 ml silica gel, 230–400 mesh, using 1 L 70/30 hexane-ethyl acetic and 500 ml 50/50 hexane-ethyl acetate as eluting solvent mixtures. Fractions 18–21 gave after recrystallization from 70/30 hexane ethyl acetate the title compound as a white solid, m.p. 168°–170° C.

EXAMPLE 26

3-[(4,6-dimethoxy-α-(N-methylcarbamoyloxy)-2-pyrimidinyl)methyl]-2 -pyridine carbox(N-allyl)amide (Table E, cpd. no. 133)

To a solution of 0.5 g of 3-[(4,6-dimethoxy-α-hydroxy-2-pyrimidinyl)methyl] -2-pyridine carbox(N-allyl)amide and 3 drops of triethylamine, in 20 ml of dichloromethane is added 3 ml of methyl isocyante, in three 1 ml portion/day while stirring at RT for 3 days. The reaction mixture is washed with water (2×50 ml), dried and concentrated. The concentrate is flash chromoatographed through 300 ml silica gel, 230–400 mesh, using 1 L 50/50 hexane-ethyl acetate, 500 ml ethyl acetate, 500 ml 80/20 ethyl acetate methanol taking 34 fractions (50 m/m). Fractions 21–25 give 0.4 g of the title product as a yellow gum.

EXAMPLE 27

Preparation of ethyl 2-bromo-4-[(4,6-dimethoxy-2-pyrimidinyl)methyl] nicotinate (Table D, cpd. no. 523)

7.32 g of ethyl 2-bromo-4-methyl nicotinate and 150 ml of THF are cooled in a dry ice/acetone bath under $N_2$ atmosphere, 30 ml of LDA are added over 5 mins and the mixture stirred for 30 mins. 6.55 g of 2-methylsulphonyl-4,6-dimethoxypyrimidine are added as a solid, rinsing with 50 ml of THF, and the mixture stirred cold for 2 hrs and slowly allowed to warm. The THF is evaporated, ca 75 ml of water added and the mixture extracted three times with methylene dichloride. The combined extracts are evaporated and the residue taken up with 20 ml of 25% ethyl acetate/ hexane and flash chromatographed using 2 l of 25% ethyl acetate/hexane in 50 ml fractions. Fractions 7 to 14 are combined, evaporated and placed in a Kugelrohr at ca 105° for 2 hrs. The residue is taken up in 20 ml of 10% ethyl acetate/hexane and flash chromatographed with 2 l 10% ethyl acetate/hexane in 50 ml portions to yield title compound (NMR) in fractions 18 to 32.

EXAMPLE 28

Preparation of ethyl-2-bromo-4-[(4,6-dimethoxy-2-pyrimidinyl) carbonyl]nicotinate (Table D, cpd. no. 524)

3.28 g of ethyl 2-bromo-4-[(4,6-dimethoxy-2-pyrimidinyl)methyl]nicotinate, 3.61 g of $SeO_2$ and 100 ml of glacial acetic acid are combined under nitrogen, heated to 110° for 1.5 hrs and slowly cooled to RT still under nitrogen. The mixture is filtered, washed through with 10 ml of acetic acid and the filtrate evaporated to remove the acetic acid. 100 ml of methylene dichloride is added to the residue and the mixture washed twice with 100 ml of sat. aqueous $NaHCO_3$. The $CH_2Cl_2$ phase is filtered and evaporated and the residue digested with 25 ml of 25% ethyl acetate/hexane at 50° for 15 mins. This solution is then poured onto a silica gel column and eluted with 3×125 ml of 25% ethyl acetate/ hexane. Evaporation of combined fractions 1 and 2 yields the title product mp 98°–99°.

EXAMPLE 29

Preparation of 1-(4,6-dimethoxy-2-pyrimidinyl)-1-hydroxy-4-methyl-furo[3,4-c]pyridine-3(1H)-one (Table B, cpd. no. 260)

0.37 g of ethyl 2-methyl-4-[4,6-dimethoxy-2-pyrimidinyl)methyl]nicotinate, 0.37 g of potassium permanganate and 100 ml of water are combined and heated at reflux for 45 mins. The mixture is cooled, a further 0.185 g of permangante added and refluxing resumed for 45 mins. The mixture is cooled to RT, filtered through celite, and sodium sulfite added until the aqueous layer becomes colorless. The filtrate is once again filtered, washed with water and extracted with 4×75 ml of methylene chloride. The combined extracts are evaporated, the residue taken up in 50 ml of warm ethyl acetate and poured onto a silica column and eluted with 2×100 ml of ethyl acetate. The combined fractions are evaporated to yield title product mp 203°–204°.

EXAMPLE 30

Preparation of N-methyl 3-phenyl-5-(4,6-dimethoxy-2-pyrimidinyl-α-t-butoxymethyl)- 4-isoxazolecarboxanilide (Table F, cpd. no. 412)

To a solution of 1.29 g of N-methyl 3-phenyl-5-(4,6-dimethoxy-2 -pyrimidinylmethyl)-4-isoxazolecarboxanilide, in 60 ml of THF is syringed in 2 ml of 1.5 molar n-butyl lithium in hexane at −70° C. The mixture is stirred for 10 mins at −70° C. and 0.6 g of t-butylperoxybenzoate, in 10 ml of THF, added over 10 mins. The reaction mixture is stirred at −70° C. for 1 hr and allowed to warm to RT. The mixture is diluted with 300 ml of water and extracted with 2×30 ml of toluene. The toluene solution is dried, concentrated and the concentrate flash chromatographed through 300 ml of silica gel, 230–400 mesh, using 1 l of 70/30 hexane/ethyl acetate, 500 ml of 50/50 hexane/ethyl acetate taking 30×50 ml fractions. Fractions 11–14 give the title compound as a yellow gum.

EXAMPLE 31

Preparation of N-methyl 3-phenyl-5-(4,6-dimethoxy-2-pyrimidinyl-α-hydroxymethyl)-4-isoxazolecarboxanilide (Table F, cpd. no. 424)

A mixture of 0.6 g of N-methyl 3-phenyl-5-(4,6-dimethoxy-2-pyrimidinyl-α -t-butoxymethyl)-4-isoxazolecarboxanilide, and 4 drops of borontrifluoridemethanol complex in 50 ml of toluene is heated at 50°–55° C. for 2 hours, washed with 20 ml of water, 50 ml of 5% sodium bicarbonate solution, dried and concentrated. The concentrate is recrystallized from hexane/methylene dichloride to give a white solid, mp 130°–131° C.

EXAMPLE 32

Preparation of N-methyl 3-phenyl-5-(4,6-dimethoxy-2-pyrimidinylcarbonyl)-4-isoxazolecarboxanilide (Table F, cpd. no. 429)

To a solution of 1.5 ml of oxalyl chloride in 30 ml of methylenedichloride cooled to −60° C. is added a solution of 2 ml of DMSO in 10 ml of methylene dichloride dropwise at -60° C. After 2 mins a solution of 0.6 g of N-methyl 3-phenyl-5-(4,6-dimethoxy-2-pyrimidinyl-α-hydroxymethyl)-4-isoxazolecarboxanilide in 10 ml of methylene dichloride is added over 3 mins at −60° C. The mixture is stirred for 15 mins at −60° C. and 1 ml of triethylamine added. The mixture is allowed to warm to RT, washed with water (3×30 ml), dried and concentrated. The concentrate is flash chromatographed through 300 ml silica gel, 230–400 mesh, using 1 1 60/40 hexane/ethyl acetate, 500 ml 50/50 hexane/ethyl acetate taking 25×50 ml fractions. Fractions 11–14 give the desired product, a yellow gum.

EXAMPLE 33

Preparation of N-methyl 3-phenyl-5-(4,6-dimethoxy-2-pyrimidinylcarbonyl)-4-isoxazolecarboxanilide (Table F, cpd. no. 429, alternative method)

A solution of 100 mg of N-methyl 3-phenyl-5-(4,6-dimethoxy-2 -pyrimidinylmethyl)-4-isoxazolecarboxanilide, 20 mg of dicobalt octacarbonyl, and 1 ml of t-butylhydroperoxide, in 60 ml of acetonitrile is refluxed for 48 hours. An additional 1 ml of t-butylhydroperoxide is added after 12 hrs and 24 hrs. Thin layer chromatography after 48 hrs indicates the presence of starting material and the title compound.

EXAMPLE 34

Oxidation of N-methyl 3-(4,6-dimethoxy-2-pyrimidinylmethyl)-5-trimethylsilyl- 4-isothiazolecarboxanilide A mixture of 2.0 g of N-methyl 3-(4,6-dimethoxy-2-pyrimidinylmethyl)-5 -trimethylsilyl-4-isothiazolecarboxanilide, 1.5 g of manganese (III) triacetate, 20 ml of acetic acid and 30 ml of methylene dichloride is stirred at RT for 48 hours. The resulting suspension is suction filtered through filter aid and the filter cake washed with water and methylene dichloride. The organic layer is separated, dried and concentrated. The concentrate is flash chromatographed through 300 ml silica gel, 230–400 mesh, using 1 1 70/30 hexane/ethyl acetate, 500 ml 50/50 hexane/ethyl acetate taking 30×50 ml fractions. Fractions 10–15 give a mixture of two components which is heated with boron trifluoride methanol complex (4 drops) in 50 ml of toluene at 80° C. for 2 hrs. The reaction mixture is washed with 30 ml of 15% sodium bicarbonate solution, dried, and concentrated. The concentrate is flash chromatographed through 300 ml silica gel, 230–400 mesh, using 1 1 60/40 hexane/ethyl acetate, 500 ml 40/60 hexane/ethyl acetate and 200 ml ethyl acetate taking 34×50 ml fractions. Fractions 20–23 give N-methyl 3-(4,6 -dimethoxy-2-pyrimidinylmethyl)-4-isothiazolecarboxanilide, 0.12 g, mp 92°–93° (Table F, cpd. no. 513). Fractions 24–28 give N-methyl 3-(4,6-dimethoxy-2 -pyrimidinylcarbonyl)-4-isothiazolecarboxanilide, 0.3 g, mp 140°–142° C. (Table F, cpd. no. 514).

EXAMPLE 35

3-[(4,6-dimethoxy-2-pyrimidinyl)hydroxy methyl]-N-methyl-2-pyridine carboxamide (Table E, cpd. no. 108)

7.2 g of methylamine gas is bubbled into 300 ml of anhydrous methanol over 10 min at 10°, 30 g of 5-(4,6-dimethoxy-2-pyridimidinyl)furo[3,4-b] pyrdine-7(5H)-one added and the mixture stirred at RT for 14 hours. The reaction mixture is then filtered and the filtrate concentrated to ca 50 ml. The resulting suspension is cooled to ca 10° and the precipitate filtered to isolate the title compound m.p. 132°–133° C.

EXAMPLE 36

3-[(4,6-dimethoxy-2-pyrimidinyl)carbonyl]-2-pyridinecarboxylic acid (Table E, cpd. no. 64)

30.3 g of $KMnO_4$ and 32.3 g of $NaHCO_3$ are suspended in 700 ml of water and 57 g of lithium 3-[(4,6-dimethoxy-2-pyrimidinyl)hydroxymethyl]-2-pyridine carboxylate is added with stirring. The reaction mixture is refluxed for 4 hrs and suction filtered hot. The filtrate is cooled over ice water and audified with conc. HCl (60 ml). The precipitated solid is filtered and dried in vacuo at 50° to give the title compound m.p. 159°–161° C.

EXAMPLE 37

5-chloro-5-(4,6-dimethoxy-2-pyrimidinyl)furo[3,4-b] pyridine-7(5H)-one (Table B, cpd. no. 68)

45.53 g of 3-[(4,6-dimethoxy-2-pyrimidinyl)carbonyl]-2-pyridinecarboxylic acid are suspended in 700 ml of carbon tetrachloride and 186.4 g of thionyl chloride added with stirring. The suspension is heated to 70° C. for 4 hrs and the reaction mixture then cooled to RT and the excess thionyl chloride and carbon tetrachloride evaporated off to give the title compound as a tan solid m.p. 146°–148° C.

EXAMPLE 38

3-[(4,6-dimethoxy-2-pyrimidinyl)carbonyl]-N,N-dimethyl-2-pyridinecarboxamide (Table E, cpd. no. 385)

15.8 g of anhydrous dimethylamine gas is bubbled into 36 g of 5-chloro-5 -(4,6-dimethoxy-2-pyrimidinyl)furo[3,4-b]pyridine-7(5H)-one in 350 ml of methylene dichloride cooled in an ice bath and the mixture then stirred overnight at RT. The reaction mixture is then washed with saturated brine solution (3×50 ml) passed through phase separating paper and the filtrate concentrated. The concentrate is dissolved in methylene dichloride, charcoal treated at RT for 1 hr and filtered.

The filtrate is concentrated to 60 ml diluted with hexane, digested for 1 hr at 35° and allowed to crystallize overnight at RT. The precipitate is filtered to isolate 35.15 g of the title product m.p. 124°–126° C.

EXAMPLE 39

3-cyano-4,7-dichloro-3-(4,6-dimethoxy-2-pyrimidinyl)phthalide (Table A, cpd. no. 269)

21.5 g of NaH in oil dispersion are added to 112.75 g of 3-cyano-4,7-dichlorophthalide and 96.7 g of 4,6-diemthoxy-2-methylsulfonyl-pyrimidine. (The hydride is washed with hexane, the hexane removed by suction and the residue covered with DMF and cooled in an ice bath.) The reaction mixture is left to stir overnight at RT and the solution then poured into 3L of water containing 15 ml of conc. $H_2SO_4$ and stirred mechanically until a viscous gum formed around the stirred blade. The water layer is decanted and extracted with 3×400 ml of toluene, the first two extracts added to the gum and the mixture stirred until the gum dissolved. The toluene solution is washed 2×100 ml of water and 1×100 ml of toluene and the combined toluene layers dried over $Na_2SO_4$ concentrated to 400 ml and left to stand overnight. The still homogeneous solution is flash-chromatographed over silica gel with toluene (250 ml fraction 5) fractions 5–9 are combined and stripped to give 30 g of the title product m.p. 123°–126° C.

EXAMPLE 40

4,7-dichloro-3-(4,6-dimethoxy-2-pyrimidinyl)-3-hydroxyphthalide (Table A, cpd. no. 250)

70 g of 3-cyano-4,7-dichloro-3-(4,6-dimethoxy-2-pyrimidinyl)phthalide are slurried in 100 ml of methanol and 16 g of NaOH pellets with 125 ml of water added. The mixture is stirred and heated to reflux for 30 mins., the solution cooled and the methanol stripped. The aqueous solution was diluted with 400 ml of water, washed with 100 ml of ether and then added dropwise to 400 ml of 1 $NH_2SO_4$ to give a solid which is filtered and dried in vacuum for 1 hr at 60°. The solid is triturated with 100 ml of ether and the suspension left overnight at RT and the solid isolated by filtration to give the title product m.p. 161°– 175° C.

EXAMPLE 41

3,6-dichloro-2-[(4,6-dimethoxy-2-pyrimidinyl)carbonyl]benzoic acid, isopropylammonium salt (Table C, cpd. no. 481)

24.13 g of 4,7-dichloro-3-(4,6-dimethoxy-2-pyrimidinyl)-3-hydroxyphthalide is slurried in 500 ml of methylene dichloride and 200 ml of methanol and 125 ml of freshly distilled isopropylamine added. The mixture is heated to reflux and the solution filtered, cooled and stripped. The solid is dried in vacuum for 4 hrs at 45° C. to give the title product m.p. 194°–196° C.

EXAMPLE 42

4,7-dichloro-3-(4,6-dimethoxy-2-pyrimidinyl)-3-hexanoyloxyphthalide (Table A, cpd. no. 265)

52 g of 4,7-dichloro-3-(4,6-dimethoxy-2-pyrimidinyl)-3-hydroxyphthalide and 500 ml of methylene dichloride are cooled in an ice bath and 23 ml of triethylamine and 1.1 g of DMAP added. The mixture is stirred until most of the solid dissolves, 35.2 g of freshly distilled hexanoic anhydride are added and the mixture is stirred for 48 hrs under $N_2$ at RT. The solution is washed with 2×100 ml 1 $NH_2SO_4$, 1×100 ml 0.1N NaOH and brine dried over $Na_2SO_4$ and concentrated to give 58.2 g of crude product which is triturated with 150 ml of ether and filtered to isolate the title product m.p. 103°–105° C.

The following compounds may be prepared analogously to the preceding examples or as otherwise described herein. Unless otherwise stated alkyl groups are straight chained i.e. in "n"-form.

TABLE A

| Cpd No | Y₁ | Y₂ | Y₃ | Y | W₁ | W₂ | W₃ | W₄ | R₁ | melting point (°C.) |
|---|---|---|---|---|---|---|---|---|---|---|
| 1 | H | H | H | OH | N | CH | C—OCH₃ | N | OCH₃ | 136–138 |
| 2 | H | H | H | H | N | CH | C—OCH₃ | N | OCH₃ | 102–104 |
| 3 | H | H | H | OCCH₃<br>‖<br>O | N | C—Br | C—OCH₃ | N | OCH₃ | 215–225 |
| 4 | H | H | H | H | N | CH | CH | N | OCH₃ | 136–138 |
| 5 | H | H | 5-Cl | H | N | CH | C—OCH₃ | N | OCH₃ | 151–153 |
| 6 | 7-Cl | 6-Cl | H | H | N | CH | C—OCH₃ | N | OCH₃ | 148–149 |
| 7 | H | H | H | H | N | CH | C—Cl | N | OCH₃ | 138–139 |
| 8 | 7-Cl | H | H | H | N | CH | C—Cl | N | OCH₃ | 152–153 |
| 9 | H | H | 4-Cl | H | N | CH | C—OCH₃ | N | OCH₃ | 128–130 |
| 10 | H | H | H | H | N | CH | C—OCH₃ | N | OCH₃ | 98–99 |
| 11 | 7-CH₃ | H | H | H | N | CH | C—Cl | N | OCH₃ | 138–140 |
| 12 | H | H | H | OH | N | CH | C—OCH₃ | N | CH₃ | 133–135 |
| 13 | 7-Cl | H | H | H | N | CH | C—OCH₃ | N | OCH₃ | 188–190 |
| 14 | 7-Cl | H | H | H | N | CH | C—OiC₃H₇ | N | OCH₃ | 101–102 |
| 15 | 7-OCH₃ | H | 4-Br | H | N | CH | C—OCH₃ | N | OCH₃ | 126–128 |
| 16 | 7-Cl | H | H | H | N | CH | C—OCH₂CF₃ | N | OCH₃ | 112–113 |
| 17 | 7-Cl | H | H | H | N | CH | C—OCH₃ | N | OCH₃ (3-F-phenoxy) | 136–138 |
| 18 | 7-Cl | H | H | H | N | CH | C—O—CH₂—(phenyl) | N | OCH₃ | 115–116 |
| 19 | 7-Cl | H | H | H | N | CH | C—OCH₃ | N | —OCH₂—(tetrahydrofuranyl) | 85–88 |
| 20 | 7-Cl | H | H | H | N | CH | C—OCH₃ | N | —OC₂H₅ | 98–100 |

TABLE A-continued

| Cpd No | Y₁ | Y₂ | Y₃ | Y | W₁ | W₂ | W₃ | W₄ | R₁ | melting point (°C.) |
|---|---|---|---|---|---|---|---|---|---|---|
| 21 | 7-Cl | H | H | Cl | N | CH | C—OCH₃ | N | —OCH₃ | 163–165 |
| 22 | 7-Cl | H | H | H | N | CH | C—OCH₂C≡CCH₃ | N | —OCH₃ | 131–133 |
| 23 | 7-Cl | H | H | SCH₃ | N | CH | C—OCH₂C≡CCH₃ | N | —OCH₃ | 134–136 |
| 24 | 7-Cl | H | H | H | N | CH | C—OCH₃ | N | —OCH₂CH=CH₂ | 72–75 |
| 25 | 7-Cl | H | H | H | N | N | C—OCH₃ | N | —OCH₃ | 157–160 |
| 26 | 7-OCH₃ | H | H | H | N | CH | C—OCH₃ | N | —OCH₃ | 152–154 |
| 27 | 7-Cl | H | H | CN | N | CH | C—OCH₃ | N | —OCH₃ | 159–161 |
| 28 | 7-Cl | 6-Cl | H | CN | N | N | C—OCH₃ | N | —OCH₃ | 184–186 |
| 29 | 7-Cl | H | H | H | N | CH | C—OCH₃ | N | —OCH₃ | 194–195 |
| 30 | 7-Cl | H | H | OCH₃ | N | CH | C—OCH₃ | N | —OCH₃ | 180–183 |
| 31 | 7-S—(phenyl) | H | H | CN | N | CH | C—OCH₃ | N | —OCH₃ | 169–171 |
| 32 | 7-OCH₃ | 6-OCH₃ | H | H | N | N | C—OCH₃ | N | —OCH₃ | 134–136 |
| 33 | 7-Cl | H | H | (pyrimidinyl) | N | CH | C—CH₃ | N | —CH₃ | 164–166 |
| 34 | H | H | H | H | N | CBr | CH | N | —OCH₃ | 163–176 |
| 35 | H | 5-Cl | H | "H1" | N | CH | C—OCH₃ | N | —OCH₃ | 151–153 |
| 36 | 7-Cl | H | H | "H2" | N | N | C—OCH₃ | N | —OCH₃ | 126–127 |
| 37 | H | H | H | OH | N | C—Cl | C—OCH₃ | N | OCH₃ | 162–165 |
| 38 | 7-F | H | H | CN | N | CH | C—OCH₃ | N | OCH₃ | 132–134 |
| 69 | 7-Cl | H | H | OC₂H₅ | N | CH | C—OCH₃ | N | OCH₃ | 148–151 |
| 72 | 7-OCH₃ | H | H | CN | N | CH | C—OCH₃ | N | OCH₃ | 159–163 |
| 73 | H | H | H | CH₃ | N | CH | C—OCH₃ | N | OCH₃ | 87–89 |

TABLE A-continued

| Cpd No | $Y_1$ | $Y_2$ | $Y_3$ | Y | $W_1$ | $W_2$ | $W_3$ | $W_4$ | $R_1$ | melting point (°C.) |
|---|---|---|---|---|---|---|---|---|---|---|
| 75 | H | H | H | "H1" | N | CH | C—OCH$_3$ | N | OCH$_3$ | 168–170 |
| 88 | 7-Cl | H | H | H | N | CH | C—OCH$_2$—C$_6$H$_4$Cl | N | —OCH$_3$ | gum, NMR |
| 98 | 7-Cl | H | H | H | N | CH | C—OCH$_2$—C$_6$H$_4$CH$_3$ | N | —OCH$_3$ | 97–98 |
| 101 | 7-Cl | H | H | H | N | CH | C—OCH$_2$—C$_6$H$_4$Cl | N | H | 125–127 |
| 102 | 7-Cl | H | H | H | N | CH | C—OCH$_2$—C$_6$H$_5$ | N | H | 83–85 |
| 104 | 7CH$_3$OC$_2$H$_4$<br>=—OCH$_2$O— | H | H | CN | N | CH | C—OCH$_3$ | N | —OCH$_3$ | 105–108 |
| 105 | 7CH$_3$OC$_2$H$_4$<br>—OCH$_2$O— | H | H | OH | N | CH | C—OCH$_3$ | N | —OCH$_3$ | 109–110 |
| 109 | 7-F | H | H | OCH$_3$ | N | CH | C—OCH$_3$ | N | —OCH$_3$ | 172–173.5 |
| 113 | 7-F | H | H | H | N | CH | C—OCH$_3$ | N | —OCH$_3$ | 138–140 |
| 117 | 7-F | H | H | OH | N | CH | C—OCH$_3$ | N | —OCH$_3$ | 183.5–185.5 |
| 118 | 7-OH | H | H | CN | N | CH | C—OCH$_3$ | N | —OCH$_3$ | 121–122 |

TABLE A-continued

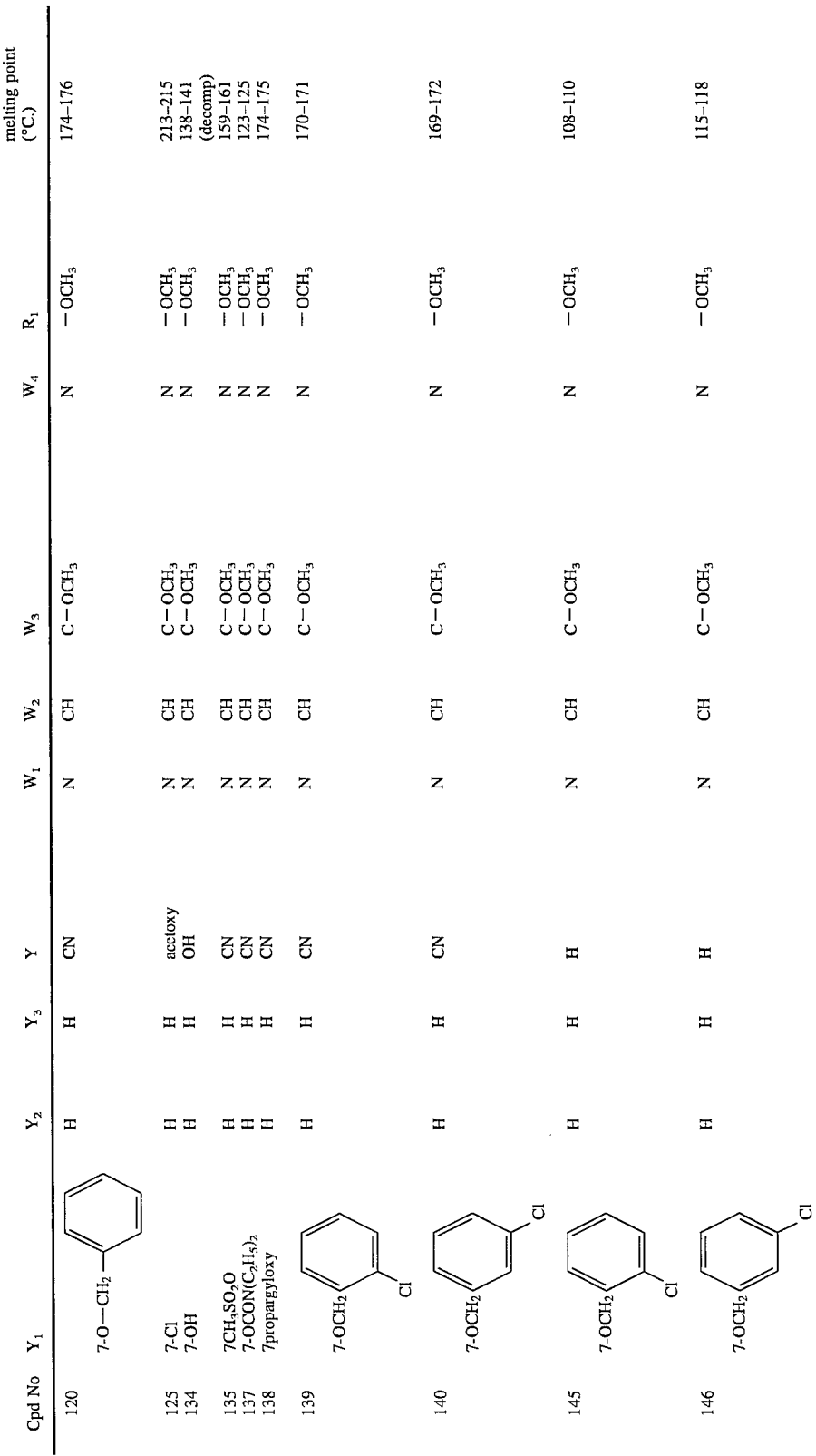

| Cpd No | $Y_1$ | $Y_2$ | $Y_3$ | Y | $W_1$ | $W_2$ | $W_3$ | $W_4$ | $R_1$ | melting point (°C.) |
|---|---|---|---|---|---|---|---|---|---|---|
| 120 | 7-O—CH$_2$—C$_6$H$_5$ | H | H | CN | N | CH | C—OCH$_3$ | N | —OCH$_3$ | 174–176 |
| 125 | 7-Cl | H | H | acetoxy | N | CH | C—OCH$_3$ | N | —OCH$_3$ | 213–215 |
| 134 | 7-OH | H | H | OH | N | CH | C—OCH$_3$ | N | —OCH$_3$ | 138–141 (decomp) |
| 135 | 7CH$_3$SO$_2$O | H | H | CN | N | CH | C—OCH$_3$ | N | —OCH$_3$ | 159–161 |
| 137 | 7-OCON(C$_2$H$_5$)$_2$ | H | H | CN | N | CH | C—OCH$_3$ | N | —OCH$_3$ | 123–125 |
| 138 | 7propargyloxy | H | H | CN | N | CH | C—OCH$_3$ | N | —OCH$_3$ | 174–175 |
| 139 | 7-OCH$_2$-C$_6$H$_5$ | H | H | CN | N | CH | C—OCH$_3$ | N | —OCH$_3$ | 170–171 |
| 140 | 7-OCH$_2$-(3-Cl-C$_6$H$_4$) | H | H | CN | N | CH | C—OCH$_3$ | N | —OCH$_3$ | 169–172 |
| 145 | 7-OCH$_2$-(3-Cl-C$_6$H$_4$) | H | H | H | N | CH | C—OCH$_3$ | N | —OCH$_3$ | 108–110 |
| 146 | 7-OCH$_2$-(3-Cl-C$_6$H$_4$) | H | H | H | N | CH | C—OCH$_3$ | N | —OCH$_3$ | 115–118 |

TABLE A-continued

| Cpd No | Y₁ | Y₂ | Y₃ | Y | W₁ | W₂ | W₃ | W₄ | R₁ | melting point (°C.) |
|---|---|---|---|---|---|---|---|---|---|---|
| 147 | 7-OCH₃ | H | H | OH | N | CH | C—OCH₃ | N | —OCH₃ | 174–176 |
| 153 | 7-propargyloxy | H | H | H | N | CH | C—OCH₃ | N | —OCH₃ | 130–131 |
| 154 | 7-OCH₂-(4-Cl-phenyl) | H | H | CN | N | CH | C—OCH₃ | N | —OCH₃ | 182–185 (decomp) |
| 166 | 7-OCF₃ | H | H | OH | N | CH | C—OCH₃ | N | —OCH₃ | 131–132 |
| 167 | 7-OCH₃ | H | H | acetoxy | N | CH | C—OCH₃ | N | —OCH₃ | 201–202 |
| 180 | 7-OCH₂-(4-Cl-phenyl) | H | H | H | N | CH | C—OCH₃ | N | —OCH₃ | 133–136 |
| 190 | 7-Oallyl | H | H | H | N | CH | C—OCH₃ | N | —OCH₃ | 109–110 |
| 195 | 7-CF₃O | H | H | acetoxy | N | CH | C—OCH₃ | N | —OCH₃ | 165–166 |
| 203 | 7-Cl | H | H | OCC₂H₅(=O) | N | CH | C—OCH₃ | N | —OCH₃ | 178–180 |
| 204 | 7-Cl | H | H | OCC₅H₁₁(=O) | N | CH | C—OCH₃ | N | —OCH₃ | 131–133 |
| 205 | 7-Cl | H | H | OC(=O)-cyclopropyl | N | CH | C—OCH₃ | N | —OCH₃ | 177–179 |
| 208 | 7-Cl | H | H | benzoyloxy | N | CH | C—OCH₃ | N | —OCH₃ | 192–194 |
| 240 | 7-Cl | H | H | OCCH=CHCH₃(=O) | N | CH | C—OCH₃ | N | —OCH₃ | 158–160 |
| 250 | 7-Cl | H | 4-Cl | OH | N | CH | C—OCH₃ | N | —OCH₃ | 171–175 |

TABLE A-continued

| Cpd No | $Y_1$ | $Y_2$ | $Y_3$ | Y | $W_1$ | $W_2$ | $W_3$ | $W_4$ | $R_1$ | melting point (°C.) |
|---|---|---|---|---|---|---|---|---|---|---|
| 253 | 7-Cl | H | H | cinnamoyloxy | N | CH | C—OCH$_3$ | N | —OCH$_3$ | 221–224 |
| 256 | 7-Cl | H | H | OCC$_{17}$H$_{35}$ ‖ O | N | CH | C—OCH$_3$ | N | —OCH$_3$ | 102–103 |
| 258 | 7-Cl | H | H | 2-butenoxy | N | CH | C—OCH$_3$ | N | —OCH$_3$ | 102–103 |
| 263 | 7-Cl | H | 4-Cl | OCCH$_3$ ‖ O | N | CH | C—OCH$_3$ | N | —OCH$_3$ | 163–164 |
| 265 | 7-Cl | H | 4-Cl | OCC$_5$H$_{11}$ ‖ O | N | CH | C—OCH$_3$ | N | —OCH$_3$ | 87–91 |
| 266 | 7-Cl | H | 4-Cl | OC△ ‖ O | N | CH | C—OCH$_3$ | N | —OCH$_3$ | 137–138 |
| 267 | 7-Cl | H | 4-Cl | OCCH=CHCH$_3$ ‖ O | N | CH | C—OCH$_3$ | N | —OCH$_3$ | 128–131 |
| 268 | 7-F | H | 4-F | CN | N | CH | C—OCH$_3$ | N | —OCH$_3$ | 135–136 |
| 269 | 7-Cl | H | 4-Cl | CN | N | CH | C—OCH$_3$ | N | —OCH$_3$ | 123–126 |
| 270 | 7-Cl | H | 4-Cl | H | N | CH | C—OCH$_3$ | N | —OCH$_3$ | 156–161 |
| 307 | 4-Cl | H | H | OH | N | CH | C—OCH$_3$ | N | —OCH$_3$ | 146–150 |
| 319 | 4-Cl | H | H | CN | N | CH | C—OCH$_3$ | N | —OCH$_3$ | 132–133 |
| 320 | 4-Cl | H | H | OCH$_3$ | N | CH | C—OCH$_3$ | N | —OCH$_3$ | 168–168.5 |
| 326 | 7-Cl | H | H | OCiC$_3$H$_7$ ‖ O | N | CH | C—OCH$_3$ | N | —OCH$_3$ | 142–143 |
| 409 | 7-Cl | H | H | OCiC$_4$H$_9$ ‖ O | N | CH | C—OCH$_3$ | N | —OCH$_3$ | 162–163 |
| 452 | 7-Cl | 4-Cl | H | OCH$_2$CH=CH$_2$ | N | CH | C—OCH$_3$ | N | OCH$_3$ | 135–136 |

TABLE A-continued

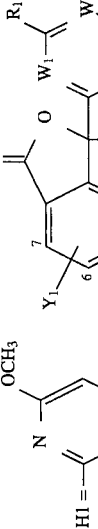

| Cpd No | $Y_1$ | $Y_2$ | $Y_3$ | Y | $W_1$ | $W_2$ | $W_3$ | $W_4$ | $R_1$ | melting point (°C.) |
|---|---|---|---|---|---|---|---|---|---|---|
| 459 | 7-OCH$_3$ | 4-Cl | H | OH | N | CH | C—OCH$_3$ | N | OCH$_3$ | 212-213 |
| 476 | 7-Si(CH$_3$)$_3$ | H | H | OH | N | CH | C—OCH$_3$ | N | OCH$_3$ | 103-104 |
| 477 | 7-OCH$_3$ | 4-Cl | H | H | N | CH | C—OCH$_3$ | N | OCH$_3$ | 183-185 |
| 486 | 7-Cl | 4-Cl | H | Cl | N | CH | C—OCH$_3$ | N | OCH$_3$ | 139-142 |
| 526 | 7-Cl | 4-F | H | OH | N | CH | C—OCH$_3$ | N | OCH$_3$ | 178-179 |
| 543 | 7-Cl | 4-CH$_3$ | H | OCnC$_5$H$_{11}$=O | N | CH | C—OCH$_3$ | N | —OCH$_3$ | 95-96 |
| 549 | 7-Cl | 4-OCH$_3$ | H | OCnC$_5$H$_{11}$=O | N | CH | C—OCH$_3$ | N | —OCH$_3$ | 116-117 |
| 568 | 7-Cl | 4-Cl | H | CN | N | C—Cl | C—OCH$_3$ | N | —OCH$_3$ | 188.5-189 |
| 580 | 7-CH$_3$ | 4-F | H | OCnC$_5$H$_{11}$=O | N | CH | C—OCH$_3$ | N | —OCH$_3$ | 103-104.5 |
| 582 | 7-CH$_3$ | 4-F | H | H | N | CH | C—OCH$_3$ | N | —OCH$_3$ | 138-140 |
| 588 | 7-SO$_2$CH$_3$ | H | H | OCnC$_5$H$_{11}$=O | N | CH | C—OCH$_3$ | N | —OCH$_3$ | 146-148 |
| 590 | 7-Cl | 4-Cl | H | OCC$_2$H$_5$=O | N | CH | C—OCH$_3$ | N | —OCH$_3$ | 145-148 |
| 591 | 7-Cl | 4-Cl | H | OCnC$_3$H$_7$=O | N | CH | C—OCH$_3$ | N | —OCH$_3$ | 130-132 |
| 595 | 7-Cl | 4-Cl | H | OCiC$_3$H$_7$=O | N | CH | C—OCH$_3$ | N | —OCH$_3$ | 127-129 |
| 597 | 7-Cl | 4-NO$_2$ | H | CN | N | CH | C—OCH$_3$ | N | —OCH$_3$ | 151.5-152.5 |

TABLE A-continued

| Cpd No | $Y_1$ | $Y_2$ | $Y_3$ | Y | $W_1$ | $W_2$ | $W_3$ | $W_4$ | $R_1$ | melting point (°C.) |
|---|---|---|---|---|---|---|---|---|---|---|
| 599 | 7-Cl | 4-Cl | H | OCtC$_4$H$_9$ =O | N | CH | C—OCH$_3$ | N | —OCH$_3$ | 171–174 |
| 605 | 7-Cl | 4-Cl | H | OCnC$_6$H$_{13}$ =O | N | CH | C—OCH$_3$ | N | —OCH$_3$ | 81–83 |
| 606 | 7-Cl | 4-Cl | H | OCnC$_4$H$_9$ =O | N | CH | C—OCH$_3$ | N | —OCH$_3$ | 103–108 |
| 607 | 7-Cl | 4-Cl | H | OCnC$_{11}$H$_{23}$ =O | N | CH | C—OCH$_3$ | N | —OCH$_3$ | 98–101 |
| 608 | 7-Cl | 4-Cl | H | OCnC$_7$H$_{15}$ =O | N | CH | C—OCH$_3$ | N | —OCH$_3$ | 83–85 |
| 610 | 7-CH$_3$ | 4-Cl | H | OCnC$_5$H$_{11}$ =O | N | CH | C—OCH$_3$ | N | —OCH$_3$ | 114–115 |
| 611 | 7-Cl | 5-Cl | H | —CNH$_2$ =O | N | CH | C—OCH$_3$ | N | —OCH$_3$ | 206–210 |
| 612 | 7-Cl | 4-F | H | OCC$_5$H$_{11}$ =O | N | CH | C—OCH$_3$ | N | —OCH$_3$ | 122–123 |
| 615 | 7-Br | H | H | OCnC$_5$H$_{11}$ =O | N | CH | C—OCH$_3$ | N | —OCH$_3$ | 142–144 |
| 618 | 7-CN | H | H | OCnC$_5$H$_{11}$ =O | N | CH | C—OCH$_3$ | N | —OCH$_3$ | 160–162 |
| 623 | 7-Cl | 4-Cl | H | OCH$_3$ | N | CH | C—OCH$_3$ | N | —OCH$_3$ | 184–185 |

TABLE A-continued

| Cpd No | Y₁ | Y₂ | Y₃ | Y | W₁ | W₂ | W₃ | W₄ | R₁ | melting point (°C.) |
|---|---|---|---|---|---|---|---|---|---|---|
| 624 | 7-Cl | 4-CH₃ | H | OCH₃ | N | CH | C—OCH₃ | N | —OCH₃ | 178–179 |

TABLE B

| Cpd No | W7 | W8 | W9 | W10 | Y | W1 | W2 | W3 | W4 | R1 | melting point (°C.) |
|---|---|---|---|---|---|---|---|---|---|---|---|
| 39 | CH | CH | CH | N | H | N | CH | C—OCH3 | N | —OCH3 | 149-151 |
| 40 | N | CH | CH | CH | H | N | CH | C—OCH3 | N | —OCH3 | 167-168 |
| 41 | CH | CH | N | CH | H | N | CH | C—OCH3 | N | —OCH3 | oil NMR |
| 42 | CH | N | CH | CH | H | N | CH | C—OCH3 | N | —OCH3 | 120-126 |
| 43 | N | C—Cl | CH | CH | H | N | CH | C—OCH3 | N | —OCH3 | 166-169 |
| 44 | N | CH | C—C2H5 | CH | H | N | N | C—OCH3 | N | —OCH3 | oil NMR |
| 45 | N | CH | CH | CH | H | N | CH | C—OCH3 | N | —OCH3 | 75-80 |
| 46 | CH | C—C2H5 | CH | CH | CH3 | N | CH | C—OCH3 | N | OCH3 | oil NMR |
| 47 | CH | CH | CH | CH | Cl | N | CH | C—OCH3 | N | OCH3 | 98-101 |
| 68 | N | CH | CH | N | "H" | N | CH | C—OCH3 | N | OCH3 | 146-148 |
| 70 | N | CH | CH | N | H | N | CH | C—OCH3 | N | OCH3 | 173-176 |
| 89 | C—CH3 | CH | CH | CH | H | N | CH | C—OCH3 | N | —OCH3 | 129-131 |
| 92 | N | CH | CH | CH | H | N | CH | C—OCH2CF3 | N | —OCH3 | 116-119 |
| 93 | N | CH | CH | CH | H | N | CH | C—CH3 | N | —CH3 | 193-195 |
| 94 | N | CH | CH | CH | H | N | CH | C—Cl | N | —OCH3 | 147-149 |
| 95 | N | CH | CH | CH | H | N | CH | C—OCH2—(3-Cl-phenyl) | N | —OCH3 | oil NMR |
| 99 | N | CH | CH | CH | H | N | CH | C—OC3H7 | N | —OCH3 | 140-142 |
| 100 | N | CH | CH | CH | H | N | CH | C—OC2H5 | N | —OCH3 | 133-135 |
| 106 | N | CH | CH | CH | H | N | CH | C—Oallyl | N | —OCH3 | 112-114 |
| 107 | N | CH | CH | CH | H | N | CH | —COCH2≡CCH3 | N | —OCH3 | oil NMR |
| 114 | C—Cl | CH | CH | CH | H | N | CH | C—OCH3 | N | —OCH3 | 168-170 |
| 121 | C—OCH3 | CH | CH | CH | H | N | CH | C—OCH3 | N | —OCH3 | 150-153 (decomp) |
| 136 | N | CH | CH | CH | H | N | CH | C—OCH3 | N | —OCH3 | 158-160 |
| 141 | N | CH | CH | CH | * | N | CH | C—OCHF2 | N | OCHF2 | 145-147 |
| 148 | CH | CH | CH | N | "H" | N | CH | C—OCH3 | N | OCH3 | 212-213 |
| 175 | CH | N | CH | CH | OH | N | CH | C—OCH3 | N | OCH3 | 172-178 |
| 260 | C—CH3 | N | CH | CH | OH | N | CH | C—OCH3 | N | OCH3 | 203-204 |
| 261 | C—COOH | N | CH | CH | OH | N | CH | C—OCH3 | N | OCH3 | 130-132 (decomp) |

TABLE B-continued

| Cpd No | W₇ | W₈ | W₉ | W₁₀ | Y | W₁ | W₂ | W₃ | W₄ | R₁ | melting point (°C.) |
|---|---|---|---|---|---|---|---|---|---|---|---|
| 317 | N | CH | CH | CH | H | N | CH | C—OCH₃ | N | CH₃ | 138–140 |
| 408 | N | CH | CH | CH | —N(CH₃)OCH₃ | N | CH | C—OCH₃ | N | OCH₃ | 168–170 |
| 572 | N | CH | CH | C—OCH₃ | CN | N | CH | C—OCH₃ | N | OCH₃ | 177–179 |
| 629 | N | CH | CH | CH | (1) | N | CH | C—OCH₃ | N | OCH₃ | 148–150 |
| 630 | N | CH | CH | CH | (2) | N | CH | C—OCH₃ | N | OCH₃ | 155–159 |
| 631 | N | CH | CH | CH | (3) | N | CH | C—OCH₃ | N | OCH₃ | 199–200 |
| 636 | N | CH | CH | CH | (4) | N | CH | C—OCH₃ | N | OCH₃ | 200–204 |
| 637 | N | CH | CH | CH | (5) | N | CH | C—OCH₃ | N | OCH₃ | 215–217 |

TABLE C

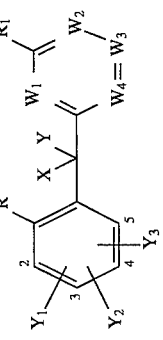

| Cpd # | $Y_1$ | $Y_2$ | $Y_3$ | R | X | Y | $W_1$ | $W_2$ | $W_3$ | $W_4$ | $R_1$ | melting point (°C.) |
|---|---|---|---|---|---|---|---|---|---|---|---|---|
| 48 | H | H | H | ![structure with N-C(CH3)2-CH2-C(=O)] | H | H | N | CH | C—OCH₃ | N | —OCH₃ | oil NMR |
| 49 | H | H | H | " | H | =O | N | CH | C—OCH₃ | N | —OCH₃ | oil NMR |
| 50 | H | H | H | ![structure with N-C(CH3)2-C(=O)-O] | H | H | N | CH | C—OCH₃ | N | —OCH₃ | 150–152 |
| 51 | H | H | H | COOH | | =NH | N | CH | C—OCH₃ | N | —OCH₃ | 225–235 (free acid) 94–95 153–157 (Li⁺ salt) |
| 52 | 2-Cl | H | H | CN | H | H | N | CH | C—OCH₃ | N | —OCH₃ | |
| 53 | 2-Cl | H | H | COOH | OH | H | N | CH | C—OCH₃ | N | —OCH₃ | |
| 54 | 2-Cl | H | H | —CO—N(CH₃)— | | OCH₃ | N | CH | C—OCH₃ | N | —OCH₃ | oil NMR |
| 55 | 2-Cl | H | H | —COOCH₃ | OH | =O | N | CH | C—OCH₃ | N | —OCH₃ | 110–111 |
| 56 | 2-Cl | H | H | —CONHCH₃ | | =O | N | CH | C—OCH₃ | N | —OCH₃ | 130–132 |
| 57 | 2-Cl | H | H | —CON(CH₃)₂ | | =O | N | CH | C—OCH₃ | N | —OCH₃ | 141–142 |
| 58 | 2-Cl | H | H | COOH | | | N | CH | C—OCH₃ | N | —OCH₃ | 276–278 (Na⁺ salt) |
| 59 | 2-Cl | H | H | ![phenyl-CONH-] | OCH₃ | H | N | CH | C—OCH₃ | N | —OCH₃ | 148–150 |
| 60 | H | H | H | COOH | OH | H | N | CH | C—OCH₃ | N | —OCH₃ | 185 (dec.) (Li⁺ salt) |

TABLE C-continued

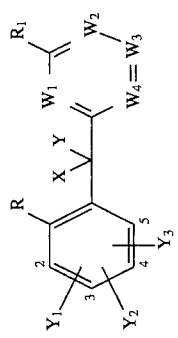

| Cpd # | Y1 | Y2 | Y3 | R | X | Y | W1 | W2 | W3 | W4 | R1 | melting point (°C.) |
|---|---|---|---|---|---|---|---|---|---|---|---|---|
| 61 | H | H | H | ![structure: CO-N with CH2-C(CH3)2-CH3 via O] | H | H | N | CH | C—Cl | N | Cl | NMR |
| 62 | H | H | H | " | Br | H | N | CH | C—OCH3 | N | OCH3 | >250 (Li+ salt) |
| 71 | H | H | H | COOH | OH | Hl | N | CH | C—OCH3 | N | OCH3 | 66–67 |
| 74 | H | H | H | COOH | OH | CH3 | N | CH | C—OCH3 | N | OCH3 | 81–83 |
| 76 | 2-Cl | H | H | COOC2H5 |  | =O | N | CH | C—OCH3 | N | OCH3 | 48–50 |
| 77 | 2Cl | H | H | COOallyl |  | =O | N | CH | C—OCH3 | N | OCH3 | 99–101 |
| 78 | 2Cl | H | H | COObuten-3-yl |  | =O | N | CH | C—OCH3 | N | OCH3 |  |
| 79 | 2Cl | H | H | COObenzyl |  | =O | N | CH | C—OCH3 | N | OCH3 |  |
| 80 | 2Cl | H | H | —CO—N—iC3H7 | OH |  | N | CH | C—OCH3 | N | OCH3 | 99–101 |
| 81 | 2Cl | H | H | —CO—N—CH3 | OH |  | N | CH | C—OCH3 | N | OCH3 | 153–154 |
| 85 | 2Cl | H | H | —CO—N(C2H5)2 |  | =O | N | CH | C—OCH3 | N | OCH3 | 110–111 |
| 86 | H | H | H | COObenzyl | OH | H | N | CH | C—OCH3 | N | OCH3 | oil NMR |
| 87 | 2Cl | H | H | —CO—N—phenyl | OH |  | N | CH | C—OCH3 | N | OCH3 | 161–163 |
| 96 | 2-Cl | H | H | —CO—N(C2H5)2 |  | =O | N | CH | C—OCH3 | N | OCH3 | 74–80 |
| 103 | 2-Cl | H | H | —CONCH3(benzyl) |  | =O | N | CH | C—OCH3 | N | OCH3 | 105–107 |
| 115 | 2-F | H | H | —COOCH3 |  | =O | N | CH | C—OCH3 | N | OCH3 | 101–104 |
| 116 | 2-F | H | H | —COOallyl |  | =O | N | CH | C—OCH3 | N | OCH3 | 97–99 |
| 122 | H | H | H | —COOallyl |  | =O | N | CH | C—OCH3 | N | OCH3 | 92–93 |
| 123 | 2-Cl | H | H | —COO 2-methyl-allyl |  | =O | N | CH | C—OCH3 | N | OCH3 | 137–139 |
| 124 | 2-Cl | H | H | —COO-3-methyl-but-2-enyl |  | =O | N | CH | C—OCH3 | N | OCH3 | 54–57 |
| 126 | 2-Cl | H | H | —COOpropargyl |  | =O | N | CH | C—OCH3 | N | OCH3 | 138–140 |
| 143 | 2-Cl | H | H | —COObut-2-enyl |  | =O | N | CH | C—OCH3 | N | OCH3 | 61–65 |

TABLE C-continued

| Cpd # | Y$_1$ | Y$_2$ | Y$_3$ | R | X | Y | W$_1$ | W$_2$ | W$_3$ | W$_4$ | R$_1$ | melting point (°C.) |
|---|---|---|---|---|---|---|---|---|---|---|---|---|
| 156 | 2-OCH$_3$ | H | H | —COOCH$_3$ | OH | =O | N | CH | C—OCH$_3$ | N | OCH$_3$ | 142–143 |
| 163 | 2-F | H | H | —COOH | | | N | CH | C—OCH$_3$ | N | OCH$_3$ | Li$^+$ salt 220–240 (decomp) |
| 165 | 2-OCH$_3$ | H | H | —COOallyl | OH | =O | N | CH | C—OCH$_3$ | N | OCH$_3$ | 100–101 |
| 181 | 2-OCH$_2$-(4-Cl-phenyl) | H | H | COOH | OH | H | N | CH | C—OCH$_3$ | N | OCH$_3$ | Li$^+$ salt 158–159 |
| 191 | 2-OCF$_3$ | H | H | COOCH$_3$ | OH | =O | N | CH | C—OCH$_3$ | N | OCH$_3$ | 80–82 (decomp) |
| 192 | 3-Cl | H | H | COOH | | | N | CH | C—OCH$_3$ | N | OCH$_3$ | Li$^+$ salt |
| 194 | 5-Cl | H | H | COOH | OH | H | N | CH | C—OCH$_3$ | N | OCH$_3$ | 170–174 (decomp) Li$^+$ salt |
| 197 | 4-Cl | H | H | COOH | OH | H | N | CH | C—OCH$_3$ | N | OCH$_3$ | 225–227 (decomp) Li$^+$ salt |
| 202 | 2-propargyloxy | H | H | COOH | OH | H | N | CH | C—OCH$_3$ | N | OCH$_3$ | 195–198 (decomp) Li$^+$ salt |
| 218 | 2-Cl | H | H | CONCH$_2$—(2-Cl-phenyl)—CH$_3$ | | =O | N | CH | C—OCH$_3$ | N | OCH$_3$ | >200 (decomp) oil NMR |
| 219 | 2-Cl | H | H | CONCH$_2$—(2-Cl-phenyl)—CH$_3$ | | =O | N | CH | C—OCH$_3$ | N | OCH$_3$ | 127–128 |
| 220 | 2-Cl | H | H | CONCH$_2$—(2-Cl-phenyl)—C$_2$H$_5$ | | =O | N | CH | C—OCH$_3$ | N | OCH$_3$ | 154–155 |
| 222 | 2-OC$_3$H$_7$ | H | H | COOH | OH | H | N | CH | C—OCH$_3$ | N | OCH$_3$ | Li$^+$ salt |

TABLE C-continued

| Cpd # | $Y_1$ | $Y_2$ | $Y_3$ | R | X | Y | $W_1$ | $W_2$ | $W_3$ | $W_4$ | $R_1$ | melting point (°C.) |
|---|---|---|---|---|---|---|---|---|---|---|---|---|
| 228 | 2-Cl | 5-Cl | H | COOH | | =O | N | CH | C—$OCH_3$ | N | $OCH_3$ | >273 (decomp) |
| 235 | 2-Cl | 5-Cl | H | COOH | OH | H | N | CH | C—$OCH_3$ | N | $OCH_3$ | $Na^+$ salt >210 (decomp) |
| 239 | 2-Cl | H | H | $COOCH_2$—$CH=CH-Cl$ | | =O | N | CH | C—$OCH_3$ | N | $OCH_3$ | $Na^+$ salt >205 (decomp) 86–87 |
| 242 | 2-Cl | H | H | CON—"HI" $\|$ $CH_3$ | $OCH_3$ | H | N | CH | C—$OCH_3$ | N | $OCH_3$ | 112–113 |
| 243 | H | H | H | COOH | | =O | N | CH | C—$OCH_3$ | N | $OCH_3$ | $Na^+$ salt >295 (decomp) |
| 244 | 2-F | H | H | COOH | | =O | N | CH | C—$OCH_3$ | N | $OCH_3$ | $Li^+$ salt 276 (decomp) |
| 247 | 2-Cl | H | H | $COOC_3H_7$ | | =O | N | CH | C—$OCH_3$ | N | $OCH_3$ | 63–65 |
| 249 | 2-Cl | 5-Cl | H | $COOC_4H_3$ | | =O | N | CH | C—$OCH_3$ | N | $OCH_3$ | 130–132 |
| 251 | 2-Cl | H | H | $COOCH_2CH=CHCl$ | | =O | N | CH | C—$OCH_3$ | N | $OCH_3$ | 107–108 |
| 262 | 2-Cl | 5-Cl | H | COOallyl | | =O | N | CH | C—$OCH_3$ | N | $OCH_3$ | 89–90 |
| 264 | 2-Cl | 5-Cl | H | $COOC_{12}H_{25}$ | | =O | N | CH | C—$OCH_3$ | N | $OCH_3$ | oil NMR |
| 274 | 2-F | 5-F | H | COOH | | =O | N | CH | C—$OCH_3$ | N | $OCH_3$ | $Na^+$ salt >295 (decomp) |
| 277 | 2-Cl | H | H | $COOC_3H_9$ | | =O | N | CH | C—$OCH_3$ | N | $OCH_3$ | NMR |
| 281 | 2-Cl | H | H | $COOC_5H_{11}$ | | =O | N | CH | C—$OCH_3$ | N | $OCH_3$ | NMR |
| 287 | 2-Cl | H | H | $COOC_6H_{13}$ | | =O | N | CH | C—$OCH_3$ | N | $OCH_3$ | 70–71 |
| 299 | 2-Cl | H | H | $COOC_7H_{15}$ | | =O | N | CH | C—$OCH_3$ | N | $OCH_3$ | NMR |
| 300 | 2-Cl | H | H | $COOC_8H_{17}$ | | =O | N | CH | C—$OCH_3$ | N | $OCH_3$ | NMR |
| 306 | 5-Cl | H | H | COOH | | =O | N | CH | C—$OCH_3$ | N | $OCH_3$ | $Na^+$ salt 266–276 (decomp) |
| 308 | 2-Cl | H | H | $COOC_{12}H_{25}$ | | =O | N | CH | C—$OCH_3$ | N | $OCH_3$ | NMR |
| 314 | 2-Cl | H | H | $COOCHC_2H_5$ $\|$ $CH_3$ | | =O | N | CH | C—$OCH_3$ | N | $OCH_3$ | 92–94 |
| 315 | 2-Cl | H | H | —$CH_2OH$ | OH | H | N | CH | C—$OCH_3$ | N | $OCH_3$ | 115–116 |
| 316 | 2-Cl | H | H | $COOiC_3H_7$ | | =O | N | CH | C—$OCH_3$ | N | $OCH_3$ | 109–110 |
| 321 | 5-Cl | H | H | $COOCH_3$ | | =O | N | CH | C—$OCH_3$ | N | $OCH_3$ | 115–116 |
| 423 | 5-Cl | H | H | COOallyl | | =O | N | CH | C—$OCH_3$ | N | $OCH_3$ | 117–118 |
| 425 | 2-Cl | H | H | —$CH_2$—O— | | OH | N | CH | C—$OCH_3$ | N | $OCH_3$ | 92–94 |

TABLE C-continued

| Cpd # | $Y_1$ | $Y_2$ | $Y_3$ | R | X | Y | $W_1$ | $W_2$ | $W_3$ | $W_4$ | $R_1$ | melting point (°C.) |
|---|---|---|---|---|---|---|---|---|---|---|---|---|
| 460 | 2-OCH$_3$ | 5-Cl | H | COOH | =O | | N | CH | C—OCH$_3$ | N | OCH$_3$ | Na$^+$ salt 228–230 |
| 461 | 2-OCH$_3$ | 5-Cl | H | COOH | =O | | N | CH | C—OCH$_3$ | N | OCH$_3$ | H$_3$N$^+$iC$_3$H$_7$ salt 190–201 |
| 478 | 2-OCH$_3$ | 5-Cl | H | COOH | OH | H | N | CH | C—OCH$_3$ | N | OCH$_3$ | Li$^+$ salt 150–160 |
| 479 | 2-Cl | 5-Cl | H | COOH | =O | | N | CH | C—OCH$_3$ | N | OCH$_3$ | H$_2$N$^+$(iC$_3$H$_7$)$_2$ salt 160–162 |
| 480 | 2-Cl | 5-Cl | H | COOH | =O | | N | CH | C—OCH$_3$ | N | OCH$_3$ | H$_2$N$^+$(CH$_3$)$_2$ salt 152–154 |
| 481 | 2-Cl | 5-Cl | H | COOH | =O | | N | CH | C—OCH$_3$ | N | OCH$_3$ | H$_3$N$^+$C$_3$H$_7$ salt 184–186 |
| 489 | 2-Cl | 5-Cl | H | CON(CH$_3$)$_2$ | =O | | N | CH | C—OCH$_3$ | N | OCH$_3$ | 145–147 |
| 502 | 2-Cl | H | H | COOH | =O | | N | CH | C—OCH$_3$ | N | OCH$_3$ | NH$_4$ salt 157–160 |
| 503 | 2-Cl | H | H | COOH | =O | | N | CH | C—OCH$_3$ | N | OCH$_3$ | H$_3$N$^+$iC$_3$H$_7$ salt 136–139 |
| 504 | 2-Cl | H | H | COOH | =O | | N | CH | C—OCH$_3$ | N | OCH$_3$ | H$_2$N$^+$(CH$_3$)$_2$ salt 163–165 |
| 527 | 2-Cl | 5-F | H | CON(CH$_3$)$_2$ | =O | | N | CH | C—OCH$_3$ | N | OCH$_3$ | 113–114 |
| 528 | 2-Cl | 5-F | H | COOH | =O | | N | CH | C—OCH$_3$ | N | OCH$_3$ | H$_3$N$^+$C$_3$H$_7$ salt 174–176 (decomp) |
| 531 | 2-Cl | 5-Cl | H | COOH | =O | | N | CH | C—OCH$_3$ | N | OCH$_3$ | H$_3$N$^+$C$_2$H$_4$OC$_2$H$_4$OH$^{(1)}$ salt 81–83 |
| 532 | 2-Cl | H | H | COOH | =O | | N | CH | C—OCH$_3$ | N | OCH$_3$ | DGA salt gum |
| 533 | 2-Cl | 5-CH$_3$ | H | COOH | =O | | N | CH | C—OCH$_3$ | N | OCH$_3$ | H$_3$N$^+$C$_3$H$_7$ salt 156–159 |
| 534 | 2-Cl | 5-OCH$_3$ | H | COOH | =O | | N | CH | C—OCH$_3$ | N | OCH$_3$ | 182–184 |
| 535 | 2-CH$_3$ | 5-F | H | COOH | =O | | N | CH | C—OCH$_3$ | N | OCH$_3$ | H$_3$N$^+$C$_3$H$_7$ salt 161–162 |
| 536 | 2-CH$_3$ | 5-Cl | H | COOH | =O | | N | CH | C—OCH$_3$ | N | OCH$_3$ | H$_3$N$^+$C$_3$H$_7$ salt 164–165 |
| 537 | 2-Cl | 4-Cl | H | COOH | =O | | N | CH | C—OCH$_3$ | N | OCH$_3$ | H$_3$N$^+$C$_3$H$_7$ salt 150–151 |
| 538 | 2-SCH$_3$ | H | H | COOH | OH | H | N | CH | C—OCH$_3$ | N | OCH$_3$ | Na$^+$ salt 205–215 (decomp) |
| 539 | 2-Cl | 5-F | H | COOH | OH | H | N | CH | C—OCH$_3$ | N | OCH$_3$ | Na$^+$ salt 216–225 (decomp) |

TABLE C-continued

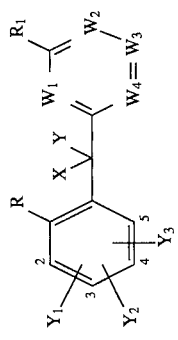

| Cpd # | $Y_1$ | $Y_2$ | $Y_3$ | R | X | Y | $W_1$ | $W_2$ | $W_3$ | $W_4$ | $R_1$ | melting point (°C.) |
|---|---|---|---|---|---|---|---|---|---|---|---|---|
| 542 | 2-Cl | 5-CH$_3$ | H | CON(CH$_3$)$_2$ | =O | | N | CH | C—OCH$_3$ | N | OCH$_3$ | 128–129 |
| 544 | 2-Cl | 5-CH$_3$ | H | COOCH$_3$ | =O | | N | CH | C—OCH$_3$ | N | OCH$_3$ | 87–88 |
| 545 | 2-Cl | 5-Cl | H | CONCH$_2$C≡CH<br>\|<br>CH$_3$ | =O | | N | CH | C—OCH$_3$ | N | OCH$_3$ | 102–104 |
| 547 | 2-Cl | 5-Cl | H | CONnC$_4$H$_9$<br>\|<br>CH$_3$ | =O | | N | CH | C—OCH$_3$ | N | OCH$_3$ | 95–97 |
| 548 | 2-Cl | 5-OCH$_3$ | H | CON(CH$_3$)$_2$ | =O | | N | CH | C—OCH$_3$ | N | OCH$_3$ | 130–131 |
| 550 | 2-Cl | 5-OCH$_3$ | H | COOH | =O | | N | CH | C—OCH$_3$ | N | OCH$_3$ | Na$^+$ salt 225–227 (decomp) |
| 556 | 2-Cl | 5-OCH$_3$ | H | COOH | OH | H | N | CH | C—OCH$_3$ | N | OCH$_3$ | Li$^+$ salt 182–185 (decomp) |
| 557 | 2-Cl | 5-OCH$_3$ | H | COOCH$_3$ | =O | | N | CH | C—OCH$_3$ | N | OCH$_3$ | 144–145 |
| 559 | 2-CF$_3$ | H | H | COOH | =O | | N | CH | C—OCH$_3$ | N | OCH$_3$ | H$_3$N$^+$iC$_3$H$_7$ salt 124–125 |
| 560 | 2-CF$_3$ | H | H | CON(CH$_3$)$_2$ | =O | | N | CH | C—OCH$_3$ | N | OCH$_3$ | 94–95 |
| 561 | 2-CF$_3$ | H | H | COOH | OH | H | N | CH | C—OCH$_3$ | N | OCH$_3$ | Li$^+$ salt 95–100 (decomp) |
| 563 | 2-SO$_2$CH$_3$ | H | H | COOH | =O | | N | CH | C—OCH$_3$ | N | OCH$_3$ | Na$^+$ salt 191–198 (decomp) |
| 566 | 2-CH$_3$ | H | H | COOH | OH | H | N | CH | C—OCH$_3$ | N | OCH$_3$ | Li$^+$ salt >260 |
| 567 | 2-CH$_3$ | H | H | COOH | OH | H | N | CH | C—OCH$_3$ | N | OCH$_3$ | 190–199 |
| 570 | 2-SCH$_3$ | 5-Cl | H | COOH | OH | H | N | CH | C—OCH$_3$ | N | OCH$_3$ | Li$^+$ salt 183–185 |
| 577 | 2-Cl | 5-Cl | H | CONCH$_2$CH$_2$OH<br>\|<br>CH$_3$ | =O | | N | CH | C—OCH$_3$ | N | OCH$_3$ | 53–56 |
| 578 | 2-Cl | 5-Cl | H | CONCH$_2$—C$_6$H$_5$<br>\|<br>CH$_3$ | =O | | N | CH | C—OCH$_3$ | N | OCH$_3$ | 134–136 |
| 581 | 2-CH$_3$ | 5-F | H | CON(CH$_3$)$_2$ | =O | | N | CH | C—OCH$_3$ | N | OCH$_3$ | 125–127 |

TABLE C-continued

| Cpd # | Y$_1$ | Y$_2$ | Y$_3$ | R | X | Y | W$_1$ | W$_2$ | W$_3$ | W$_4$ | R$_1$ | melting point (°C.) |
|---|---|---|---|---|---|---|---|---|---|---|---|---|
| 583 | 2-SCH$_3$ | H | H | COOH | | =O | N | CH | C—OCH$_3$ | N | OCH$_3$ | Na$^+$ salt 286–289 (decomp) |
| 585 | 2-NH$_2$ | H | H | COOH | | =O | N | CH | C—OCH$_3$ | N | OCH$_3$ | Na$^+$ salt 265–270 (decomp) |
| 586 | 2-SO$_2$CH$_3$ | H | H | COOH | | =O | N | CH | C—OCH$_3$ | N | OCH$_3$ | Na$^+$ salt 265–266 |
| 587 | 2-SO$_2$CH$_3$ | H | H | COOH | | =O | N | CH | C—OCH$_3$ | N | OCH$_3$ | H$_3$N$^+$iC$_3$H$_7$ salt 84–90 (decomp) |
| 589 | 2-CH$_3$ | 5-F | H | COOH | OH | H | N | CH | C—OCH$_3$ | N | OCH$_3$ | Li$^+$ salt 176–181 (decomp) |
| 592 | 2-SO$_2$CH$_3$ | 5-Cl | H | COOH | OH | H | N | CH | C—OCH$_3$ | N | OCH$_3$ | Li$^+$ salt 213–216 (decomp) |
| 593 | 2-Cl | 5-Cl | H | CONCH$_3$ (4-chlorophenyl-CH$_2$) | | =O | N | CH | C—OCH$_3$ | N | OCH$_3$ | 165–166 |
| 594 | 2-Cl | 5-Cl | | CONCH$_3$ (naphthyl-CH$_2$) | | =O | N | CH | C—OCH$_3$ | N | OCH$_3$ | 123–125 |
| 596 | 2-Cl | 5-NO$_2$ | H | CN | CN | H | N | CH | C—OCH$_3$ | N | OCH$_3$ | 174.5–175.5 |
| 600 | 2-Cl | 5-NO$_2$ | H | COOH | | =O | N | CH | C—OCH$_3$ | N | OCH$_3$ | H$_3$N$^+$iC$_3$H$_7$ salt 168–170 |
| 604 | 2-Cl | 5-Cl | H | CONCH$_2$COOCH$_3$ CH$_3$ | | =O | N | CH | C—OCH$_3$ | N | OCH$_3$ | 143–144 |
| 613 | 2-Br | H | H | CON(CH$_3$)$_2$ | | =O | N | CH | C—OCH$_3$ | N | OCH$_3$ | 134–135 |
| 614 | 2-Br | H | H | COOH | | =O | N | CH | C—OCH$_3$ | N | OCH$_3$ | Na$^+$ salt 285–286 |
| 616 | 2-Br | H | H | COOH | OH | H | N | CH | C—OCH$_3$ | N | OCH$_3$ | Na$^+$ salt 166–174 (decomp) |

TABLE C-continued

Structure: phenyl ring with substituents Y1 (position 2), Y2 (positions 3 or 5), Y3 (position 5), R (position 1 on ring attached to CXY group), connected via CXY to C(W1=W2)(W3=W4) with R1 on the W3 position.

| Cpd # | Y₁ | Y₂ | Y₃ | R | X | Y | W₁ | W₂ | W₃ | W₄ | R₁ | melting point (°C.) |
|---|---|---|---|---|---|---|---|---|---|---|---|---|
| 617 | 2-CN | H | H | COOH | =O | | N | CH | C—OCH₃ | N | OCH₃ | H₃N⁺C₃H₇ salt 160–162 |
| 619 | 2-CN | H | H | COOH | =O | | N | CH | C—OCH₃ | N | OCH₃ | Na⁺ salt 293–295 (decomp) |
| 620 | 2-CN | H | H | CON(CH₃)₂ | =O | | N | CH | C—OCH₃ | N | OCH₃ | 150–151 |
| 621 | 2-CN | H | H | COOH | OH | H | N | CH | C—OCH₃ | N | OCH₃ | Na₊ salt 118–125 (decomp) |
| 627 | 2-Cl | 5-Cl | H | CN | CN | H | N | CH | C—OCH₃ | N | OCH₃ | 134–136 |
| 628 | 2-Cl | 3-Cl | H | CN | CN | H | N | CH | C—OCH₃ | N | OCH₃ | 122–125 |

⁽¹⁾H₃N⁺C₂H₄OC₂H₄OH is also known as diglycolamine or DGA

TABLE D

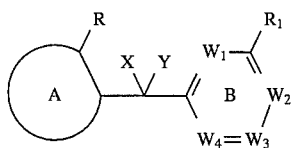

| Cpd No | A (anti clockwise)* | R | X | Y | W$_1$ | W$_2$ | W$_3$ | W$_4$ | R$_1$ | melting point (°C.) |
|---|---|---|---|---|---|---|---|---|---|---|
| 65 | —S—CH=CH— | | —C(=O)—O— | H | N | CH | C—OCH$_3$ | N | OCH$_3$ | 125–127 |
| 66 | —S—CH=CH— | | —C(=O)—O— | H | N | N | C—OCH$_3$ | N | OCH$_3$ | oil NMR |
| 67 | —CH=CH—CH=N— | COOH | OH | CH$_3$ | N | CH | C—OCH$_3$ | N | OCH$_3$ | Li$^+$ salt >283 (decomp) |
| 119 | =C(Cl)—N=CH—CH= | CONHCH$_3$ | OH | H | N | CH | C—OCH$_3$ | N | OCH$_3$ | oil NMR |
| 142 | =CH—CH=CH—N= | COOC$_2$H$_5$ | CN | H | N | CH | C—OCH$_3$ | N | OCH$_3$ | 109–111 |
| 149 | =CH—CH=CH—N= | COOH | OH | H | N | CH | C—OCH$_3$ | N | OCH$_3$ | Li$^+$ salt 160–165 (decomp) |
| 150 | =CH—CH=CH—N= | CONHC$_3$H$_7$ | OH | H | N | CH | C—OCH$_3$ | N | OCH$_3$ | oil NMR |
| 173 | =CH—CH=CH—N= | COOH | OH | H | N | CH | C—OCH$_3$ | N | OCH$_3$ | 142–145 (decomp) |
| 174 | =CH—CH=CH—N= | COOCH$_3$ | OH | H | N | CH | C—OCH$_3$ | N | OCH$_3$ | oil NMR |
| 176 | =CH—CH=CH—N= | COOCH$_3$ | =O | | N | CH | C—OCH$_3$ | N | OCH$_3$ | 129–131 |
| 178 | =C(OCH$_3$)—N=CH—CH= | COOCH$_3$ | H | H | N | CH | C—OCH$_3$ | N | OCH$_3$ | oil NMR |
| 179 | =C(OCH$_3$)—N=CH—CH= | COOH | H | H | N | CH | C—OCH$_3$ | N | OCH$_3$ | Li$^+$ salt >240 (decomp) |
| 186 | =C(OCH$_3$)—N=CH—CH= | COOCH$_3$ | =O | | N | CH | C—OCH$_3$ | N | OCH$_3$ | 147–149 |
| 187 | =C(OCH$_3$)—N=CH—CH= | COOH | =O | | N | CH | C—OCH$_3$ | N | OCH$_3$ | Na$^+$ salt 235 |
| 198 | =C(OCH$_3$)—N=CH—CH= | COOCH$_3$ | Br | H | N | CH | C—OCH$_3$ | N | OCH$_3$ | 125–126 |
| 199 | =CH—CH=CH—N= | COOH | OH | H | N | CH | C—OCH$_3$ | N | OCH$_3$ | Na$^+$ salt 242 (decomp) |
| 206 | =C(OCH$_3$)—N=CH—CH= | COOCH$_3$ | acetoxy | H | N | CH | C—OCH$_3$ | N | OCH$_3$ | oil NMR |
| 216 | =C(OCH$_3$)—N=CH—CH= | COOC$_2$H$_5$ | H | H | N | CH | C—OCH$_3$ | N | OCH$_3$ | oil NMR |
| 236 | =C(CH$_3$)—N=CH—CH= | COOC$_2$H$_5$ | Br | H | N | CH | C—OCH$_3$ | N | OCH$_3$ | oil NMR |
| 237 | =C(CH$_2$Br)—N=CH—CH= | COOC$_2$H$_5$ | Br | H | N | CH | C—OCH$_3$ | N | OCH$_3$ | oil NMR |
| 238 | =C(CH$_2$OCOCH$_3$)—N=CH—CH= | COOC$_2$H$_5$ | Br | H | N | CH | C—OCH$_3$ | N | OCH$_3$ | oil NMR |
| 248 | =C(CH$_3$)—N=CH—CH= | COOC$_2$H$_5$ | =O | | N | CH | C—OCH$_3$ | N | OCH$_3$ | 103–104 |

TABLE D-continued

| Cpd No | A (anti clockwise)* | R | X | Y | $W_1$ | $W_2$ | $W_3$ | $W_4$ | $R_1$ | melting point (°C.) |
|---|---|---|---|---|---|---|---|---|---|---|
| 254 | =C−N=CH−CH=<br>    \|<br>    $CH_3$ | COOH |  | =O | N | CH | C−$OCH_3$ | N | $OCH_3$ | 180–185 (decomp) |
| 301 | =CH−CH=CH−N= | $CON(C_2H_5)_2$ | H | H | N | CH | C−$OCH_3$ | N | $OCH_3$ | 69–72 |
| 302 | =CH−CH=CH−N= | COOH | OH | H | N | CH | C−$OCH_3$ | N | $OCH_3$ | $K^+$ salt 220–230 (decomp) |
| 330 | =CH−CH=CH−N= | $CON(C_2H_5)_2$ | $OtC_4H_9$ | H | N | CH | C−$OCH_3$ | N | $OCH_3$ | oil NMR |
| 414 | −N=CH−CH=CH− | −C(=O)−N(O−$CH_2$−Ph)− |  | OH | N | CH | C−$OCH_3$ | N | $OCH_3$ | 136–138 |
| 415 | =CH−CH=CH−N= | CON(CH_3)(Ph) |  | =O | CH | CH | CH | CH | $CF_3$ |  |
| 416 | =CH−CH=CH−N= | CON(CH_3)(Ph) | OH | H | CH | CH | CH | CH | $CF_3$ |  |
| 417 | =CH−CH=CH−N= | CONH(2,4-F_2-Ph) | OH | H | CH | CH | CH | CH | $CF_3$ |  |
| 418 | =CH−CH=CH−N= | CONH(Ph) | OH | H | CH | CH | CH | CH | $CF_3$ |  |
| 419 | −N=CH−CH=CH− | CON(CH_3)(Ph) |  | =O | CH | CH | CH | CH | $CF_3$ |  |
| 420 | −N=CH−CH=CH− | −CON(CH_3)(Ph) | OH | H | CH | CH | CH | CH | $CF_3$ |  |
| 421 | −N=CH−CH=CH− | −CONH(2,4-F_2-Ph) | OH | H | CH | CH | CH | CH | $CF_3$ |  |
| 422 | −N=CH−CH=CH− | −CONH(Ph) | OH | H | CH | CH | CH | CH | $CF_3$ |  |

TABLE D-continued

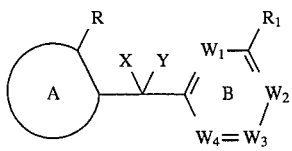

| Cpd No | A (anti clockwise)* | R | X | Y | $W_1$ | $W_2$ | $W_3$ | $W_4$ | $R_1$ | melting point (°C.) |
|---|---|---|---|---|---|---|---|---|---|---|
| 426 | N=CH—CH=CH | —C(=O)—N— with H$_5$C$_2$ and C$_2$H$_5$ substituted phenyl |  | OH | N | CH | C—OCH$_3$ | N | OCH$_3$ | 163–165 |
| 511 | =C—N=CH—CH= <br> \|<br> OCH$_3$ | COOCH$_3$ | O(t)C$_4$H$_9$ | H | N | CH | C—OCH$_3$ | N | OCH$_3$ | 115–117 |
| 512 | =C—N=CH—CH= <br> \|<br> OCH$_3$ | CONHC$_6$H$_{13}$ | OH | H | N | CH | C—OCH$_3$ | N | OCH$_3$ | 94–97 |
| 518 | —N=CH—CH=CH— <br> ↓<br> O$^-$ | COOH |  | =O | N | CH | C—OCH$_3$ | N | OCH$_3$ | NMR |
| 523 | =C—N=CH—CH= <br> \|<br> Br | COOC$_2$H$_5$ | H | H | N | CH | C—OCH$_3$ | N | OCH$_3$ | NMR |
| 524 | =C—N=CH—CH= <br> \|<br> Br | COOC$_2$H$_5$ |  | =O | N | CH | C—OCH$_3$ | N | OCH$_3$ | 98–99 |
| 525 | =C—N=CH—CH= <br> \|<br> Br | COOH |  | =O | N | CH | C—OCH$_3$ | N | OCH$_3$ | Li$^+$ salt >280° |
| 529 | =C—N=CH—CH= <br> \|<br> N(CH$_3$)$_2$ | COOC$_2$H$_5$ | H | H | N | CH | C—OCH$_3$ | N | OCH$_3$ | 83–85 |
| 540 | =C—N=CH—CH= <br> \|<br> N(CH$_3$)$_2$ | COOC$_2$H$_5$ |  | =O | N | CH | C—OCH$_3$ | N | OCH$_3$ | 163–165 |
| 541 | =C—N=CH—CH= <br> \|<br> N(CH$_3$)$_2$ | COOH |  | =O | N | CH | C—OCH$_3$ | N | OCH$_3$ | Li$^+$ salt 275–280 |
| 551 | =C—N=CH—CH= <br> \|<br> N(CH$_3$)$_2$ | CON(CH$_3$)$_2$ |  | =O | N | CH | C—OCH$_3$ | N | OCH$_3$ | 138–140 |
| 552 | =C—N=CH—CH= <br> \|<br> CN | COOC$_2$H$_5$ | H | H | N | CH | C—OCH$_3$ | N | OCH$_3$ | 89–92 |
| 553 | =C—N=CH—CH= <br> \|<br> CN | COOC$_2$H$_5$ | Br | H | N | CH | C—OCH$_3$ | N | OCH$_3$ | NMR |
| 554 | =C—N=CH—CH= <br> \|<br> CN | COOC$_2$H$_5$ |  | =O | N | CH | C—OCH$_3$ | N | OCH$_3$ | 116–118 |
| 555 | =C—N=CH—CH= <br> \|<br> CN | COOH |  | =O | N | CH | C—OCH$_3$ | N | OCH$_3$ | Li$^+$ salt >275 |

*Left hand atom attached to R-bearing carbon

TABLE E-continued

| Cpd # | Y₁ | Y₂ | Y₃ | R | X | Y | W₁ | W₂ | W₃ | W₄ | R₁ | m.p. |
|---|---|---|---|---|---|---|---|---|---|---|---|---|
| 158 | H | H | H | CONH₂ | benzoyloxy | H | N | CH | C—OCH₃ | N | OCH₃ | 115–116 |
| 159 | H | H | H | CON(benzoyl)₂ | benzoyloxy | H | N | CH | C—OCH₃ | N | OCH₃ | 168–170 |
| 160 | H | H | H | CONH—CH₂—(2,4-diMe-C₆H₃) | OH | H | N | CH | C—OCH₃ | N | OCH₃ | 88–90 |
| 161 | H | H | H | CONH₂ | OCO—C₆H₄—C₂H₅ | H | N | CH | C—OCH₃ | N | OCH₃ | 138–140 |
| 162 | H | H | H | CON(CO—C₆H₄—C₂H₅)₂ | OCO—C₆H₄—C₂H₅ | H | N | CH | C—OCH₃ | N | OCH₃ | 198–200 |
| 164 | H | H | H | CONHCH₂—C₆H₄—OCH₃ | OH | H | N | CH | C—OCH₃ | N | OCH₃ | 91–94 |
| 168 | H | H | H | CONHCH₂—C₆H₄—NO₂ | OH | H | N | CH | C—OCH₃ | N | OCH₃ | 103–106 |
| 169 | H | H |   |   | —C(O)—N(CH₃)—C(O)—C₆H₄—C₂H₅ | H |   | CH | C—OCH₃ | N | OCH₃ | 135–137 |
| 170 | H | H | H | CONHNH(t)C₄H₉ | OH | H | N | CH | C—OCH₃ | N | OCH₃ | 109–110 |

TABLE E-continued

| Cpd # | Y$_1$ | Y$_2$ | Y$_3$ | R | X | Y | W$_1$ | W$_2$ | W$_3$ | W$_4$ | R$_1$ | m.p. |
|---|---|---|---|---|---|---|---|---|---|---|---|---|
| 171 | H | H | H | CONHCH$_2$-C$_6$H$_4$-C$_2$H$_5$ | OH | H | N | CH | C—OCH$_3$ | N | OCH$_3$ | NMR |
| 172 | H | H | H | CONHCH$_2$-C$_6$H$_4$-NH$_2$ | OH | H | N | CH | C—OCH$_3$ | N | OCH$_3$ | 140–142 |
| 177 | H | H | H | CONHC$_2$H$_4$N(CH$_3$)$_2$ | OH | H | N | CH | C—OCH$_3$ | N | OCH$_3$ | NMR |
| 182 | H | H | H | CONHNH-C$_6$H$_5$ | OH | H | N | CH | C—OCH$_3$ | N | OCH$_3$ | 117–120 |
| 183 | H | H | H | CONH-C$_6$H$_4$-iC$_3$H$_7$ | OH | H | N | CH | C—OCH$_3$ | N | OCH$_3$ | 132–133 |
| 184 | H | H | H | CONH-C$_6$H$_4$-C$_2$H$_5$ | OH | H | N | CH | C—OCH$_3$ | N | OCH$_3$ | 113–114 |
| 185 | H | H | H | CONHSO$_2$CH$_3$ | OH | H | N | CH | C—OCH$_3$ | N | OCH$_3$ | 133–135 |
| 188 | H | H | H | CONH-C$_6$H$_4$-Cl | OH | H | N | CH | C—OCH$_3$ | N | OCH$_3$ | 115–117 |
| 189 | H | H | H | CONHCH$_2$COOCH$_3$ | OH | H | N | CH | C—OCH$_3$ | N | OCH$_3$ | 97–99 |

TABLE E-continued

| Cpd # | Y₁ | Y₂ | Y₃ | R | X | Y | W₁ | W₂ | W₃ | W₄ | R₁ | m.p. |
|---|---|---|---|---|---|---|---|---|---|---|---|---|
| 193 | H | H | H | CONHCHCOOCH₃ \| iC₃H₇ | OH | H | N | CH | C—OCH₃ | N | OCH₃ | oil NMR |
| 196 | H | H | H | CONHCH₂-furyl | OH | H | N | CH | C—OCH₃ | N | OCH₃ | oil NMR |
| 199 | H | H | H | COOH | OH | H | N | CH | C—OCH₃ | N | OCH₃ | 144–146 |
| 200 | H | H | H | CONHCH₂-naphthyl | OH | H | N | CH | C—OCH₃ | N | OCH₃ | |
| 201 | H | H | H | CONHCH₂-tetrahydrofuryl | OH | H | N | CH | C—OCH₃ | N | OCH₃ | oil NMR |
| 207 | H | H | H | CONH₂ | dichloro-acetoxy | H | N | CH | C—OCH₃ | N | OCH₃ | 118–119 |
| 209 | H | H | H | CONHCH-phenyl \| COOCH₃ | OH | H | N | CH | C—OCH₃ | N | OCH₃ | NMR |
| 210 | H | H | H | CONHCH₂-(OCH₃-phenyl) | OH | H | N | CH | C—OCH₃ | N | OCH₃ | 119–121 |

TABLE E-continued

| Cpd # | Y₁ | Y₂ | Y₃ | R | X | Y | W₁ | W₂ | W₃ | W₄ | R₁ | m.p. |
|---|---|---|---|---|---|---|---|---|---|---|---|---|
| 211 | H | H | H | CONHCH₂–C₆H₄–OCH₃ | OH | H | N | CH | C—OCH₃ | N | OCH₃ | 125–127 |
| 212 | H | H | H | CONHCH₂–C₆H₄–SO₂NH₂ | OH | H | N | CH | C—OCH₃ | N | OCH₃ | oil NMR |
| 213 | H | H | H | CONHCH₂–(pyridyl) | OH | H | N | CH | C—OCH₃ | N | OCH₃ | oil NMR |
| 214 | H | H | H | CONHCH₂–(thienyl) | OH | H | N | CH | C—OCH₃ | N | OCH₃ | oil NMR |
| 215 | H | H | H | CONH–C₆H₄–OCH₃ | OH | H | N | CH | C—OCH₃ | N | OCH₃ | 119–120 |
| 217 | H | H | H | CONH–C₆H₄–NO₂ | OH | H | N | CH | C—OCH₃ | N | OCH₃ | 182–183 |
| 221 | H | H | H | CONHCH₂–(cyclopropyl) | OH | H | N | CH | C—OCH₃ | N | OCH₃ | 105–106 |
| 223 | H | H | H | CONHCH₂–C₆H₄–NO₂ | OH | H | N | CH | C—OCH₃ | N | OCH₃ | 130–131 |

TABLE E-continued

| Cpd # | $Y_1$ | $Y_2$ | $Y_3$ | R | X | Y | $W_1$ | $W_2$ | $W_3$ | $W_4$ | $R_1$ | m.p. |
|---|---|---|---|---|---|---|---|---|---|---|---|---|
| 224 | H | H | H | CONHNH—(4-Cl-phenyl) | OH | H | N | CH | C—OCH$_3$ | N | OCH$_3$ | 149–150 |
| 225 | H | H | H | CONHCH$_2$—(2,3-diCH$_3$-phenyl) | OH | H | N | CH | C—OCH$_3$ | N | OCH$_3$ | 98–100 |
| 226 | H | H | H | CONH—N(piperidine) | OH | H | N | CH | C—OCH$_3$ | N | OCH$_3$ | 40–42 |
| 227 | H | H | H | CONHC$_2$H$_4$—N(piperidine) | OH | H | N | CH | C—OCH$_3$ | N | OCH$_3$ | NMR |
| 229 | H | H | H | CONHNH—(4-OCH$_3$-phenyl) | OH | H | N | CH | C—OCH$_3$ | N | OCH$_3$ | 121–123 |
| 230 | H | H | H | CONHNH—(4-CH$_3$-phenyl) | OH | H | N | CH | C—OCH$_3$ | N | OCH$_3$ | 130–132 |
| 231 | H | H | H | CONH—phenyl | OH | H | N | CH | C—OCH$_3$ | N | OCH$_3$ | 138–140 |

TABLE E-continued

| Cpd # | Y$_1$ | Y$_2$ | Y$_3$ | R | X | Y | W$_1$ | W$_2$ | W$_3$ | W$_4$ | R$_1$ | m.p. |
|---|---|---|---|---|---|---|---|---|---|---|---|---|
| 232 | H | H | H | CONH-(4-pyridyl) | OH | H | N | CH | C—OCH$_3$ | N | OCH$_3$ | 152–154 |
| 233 | H | H | H | CONHC$_3$H$_6$N(CH$_3$)$_2$ | OH | H | N | CH | C—OCH$_3$ | N | OCH$_3$ | NMR |
| 234 | H | H | H | CONHC$_2$H$_4$N(C$_2$H$_5$)$_2$ | OH | "HI" | N | CH | C—OCH$_3$ | N | OCH$_3$ | NMR |
| 241 | H | H | H | COOH | OH | | N | CH | C—OCH$_3$ | N | OCH$_3$ | Li$^+$ salt 158–160 |
| 245 | H | H | H | CONHNH-(2,4-diClPh) | OH | H | N | CH | C—OCH$_3$ | N | OCH$_3$ | 150–154 |
| 246 | H | H | H | CONHNH-(2,6-diClPh) | OH | H | N | CH | C—OCH$_3$ | N | OCH$_3$ | 133–134 |
| 252 | H | H | H | CONHNH-(4-BrPh) | OH | H | N | CH | C—OCH$_3$ | N | OCH$_3$ | 150–151 |
| 255 | H | H | H | CONH-morpholino | OH | H | N | CH | C—OCH$_3$ | N | OCH$_3$ | 52–54 |
| 257 | H | H | H | CONHNHCH$_2$-Ph | OH | H | N | CH | C—OCH$_3$ | N | OCH$_3$ | NMR |

TABLE E-continued

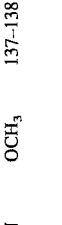

| Cpd # | Y₁ | Y₂ | Y₃ | R | X | Y | W₁ | W₂ | W₃ | W₄ | R₁ | m.p. |
|---|---|---|---|---|---|---|---|---|---|---|---|---|
| 259 | H | H | H | CONHC₈H₁₇ | OH | H | N | CH | C—OCH₃ | N | OCH₃ | 54-56 |
| 271 | H | H | H | 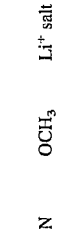 | OH | N | CH | C—OCH₃ | C—OCH₃ | N | OCH₃ | 137-138 |
| 272 | H | H | H | COOH | | =O | N | CH | C—OCH₃ | N | OCH₃ | Li⁺ salt 210 (decomp) |
| 273 | H | H | H | 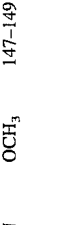 | | =O | N | CH | C—OCH₃ | N | OCH₃ | 147-149 |
| 275 | H | H | H | CONHNH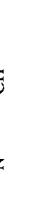 | OH | H | N | CH | C—OCH₃ | N | OCH₃ | 158-160 |
| 276 | H | H | H | COOH | | =O | N | CH | C—OCH₃ | N | OCH₃ | Na⁺ salt 195 (decomp) K⁺ salt (255 decomp) |
| 278 | H | H | H | CONHC₉H₁₉ | OH | H | N | CH | C—OCH₃ | N | OCH₃ | 45-47 |
| 279 | H | H | H | CONHC₁₀H₂₁ | OH | H | N | CH | C—OCH₃ | N | OCH₃ | 49-51 |
| 280 | H | H | H | CONHNH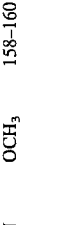 | OH | H | N | CH | C—OCH₃ | N | OCH₃ | 58-62 |
| 282 | H | H | H | CONHCH₂iPr | OH | H | N | CH | C—OCH₃ | N | OCH₃ | 103-105 |
| 283 | H | H | H | CONHCH₂CH(OCH₃)₂ | OH | H | N | CH | C—OCH₃ | N | OCH₃ | NMR |
| 284 | H | H | H | CONH—C(CH₃)₂—C≡CH | OH | H | N | CH | C—OCH₃ | N | OCH₃ | NMR |

TABLE E-continued

| Cpd # | Y₁ | Y₂ | Y₃ | R | X | Y | W₁ | W₂ | W₃ | W₄ | R₁ | m.p. |
|---|---|---|---|---|---|---|---|---|---|---|---|---|
| 285 | H | H | H | CONHC₄H₉ | OH | H | N | CH | C—OCH₃ | N | OCH₃ | NMR |
| 286 | H | H | H | CONHCH—CH₂OCH₃<br>　　　　｜<br>　　　　CH₃ | OH | H | N | CH | C—OCH₃ | N | OCH₃ | NMR |
| 288 | H | H | H | CONHNH—(3,4-dichlorophenyl) | OH | H | N | CH | C—OCH₃ | N | OCH₃ | 182–184 |
| 289 | H | H | H | CONHNH—(3,5-dichlorophenyl) | OH | H | N | CH | C—OCH₃ | N | OCH₃ | 181–183 |
| 290 | H | H | H | CONH—(3-methoxyphenyl) | OH | H | N | CH | C—OCH₃ | N | OCH₃ | NMR |
| 291 | H | H | H | CONHC₆H₁₂N(CH₃)₂ | OH | H | N | CH | C—OCH₃ | N | OCH₃ | NMR |
| 292 | H | H | H | CONHC₄H₈N(CH₃)₂ | OH | H | N | CH | C—OCH₃ | N | OCH₃ | NMR |
| 293 | H | H | H | CONHNH—(4-fluorophenyl) | OH | H | N | CH | C—OCH₃ | N | OCH₃ | 131–132 |

TABLE E-continued

| Cpd # | Y₁ | Y₂ | Y₃ | R | X | Y | W₁ | W₂ | W₃ | W₄ | R₁ | m.p. |
|---|---|---|---|---|---|---|---|---|---|---|---|---|
| 294 | H | H | H | CONHNH-(2,4-difluorophenyl) | OH | H | N | CH | C—OCH₃ | N | OCH₃ | 124–126 |
| 295 | H | H | H | CONHCH₂-(2,3-dimethoxyphenyl) | OH | H | N | CH | C—OCH₃ | N | OCH₃ | NMR |
| 296 | H | H | H | CONHCH₂-(2,6-dimethoxyphenyl) | OH | H | N | CH | C—OCH₃ | N | OCH₃ | 88–90 |
| 297 | H | H | H | CONHCH₂-(3,5-dimethoxyphenyl) | OH | H | N | CH | C—OCH₃ | N | OCH₃ | NMR |
| 298 | H | H | H | CONHCH₂CHCH₃(OH) | OH | H | N | CH | C—OCH₃ | N | OCH₃ | NMR |
| 303 | H | H | H | CONH-(2,3-dimethoxyphenyl) | OH | H | N | CH | C—OCH₃ | N | OCH₃ | NMR |

TABLE E-continued

| Cpd # | Y₁ | Y₂ | Y₃ | R | X | Y | W₁ | W₂ | W₃ | W₄ | R₁ | m.p. |
|---|---|---|---|---|---|---|---|---|---|---|---|---|
| 304 | H | H | H | CONH-C₆H₄-N(CH₃)₂ | OH | H | N | CH | C—OCH₃ | N | OCH₃ | 54-56 |
| 305 | H | H | H | CONHC(CH₃)H-C₆H₅ | OH | H | N | CH | C—OCH₃ | N | OCH₃ | D(+) 64-68<br>L(−) NMR |
| 309 | H | H | H | CONH-C₆H₄-SCH₃ | OH | H | N | CH | C—OCH₃ | N | OCH₃ | 133-134 |
| 310 | H | H | H | CONH-C₆H₄-C₂H₅ | OH | H | N | CH | C—OCH₃ | N | OCH₃ | 102-104 |
| 311 | H | H | H | CONH-C₆H₄-C₂H₅ | OH | H | N | CH | C—OCH₃ | N | OCH₃ | 122-123 |
| 312 | H | H | H | CONH-C₆H₄-F | OH | H | N | CH | C—OCH₃ | N | OCH₃ | 126-128 |
| 313 | H | H | H | CONHNH-C₆H₅ | OH | H | N | CH | C—OCH₃ | N | OCH₃ | 106-108 |
| 318 | H | H | H | CONHCH₂-C₆H₄-N(CH₃)₂<br>COOH | OH | H | N | CH | C—OCH₃ | N | CH₃ | Li⁺ salt<br>185-188 (decomp) |

TABLE E-continued

| Cpd # | Y₁ | Y₂ | Y₃ | R | X | Y | W₁ | W₂ | W₃ | W₄ | R₁ | m.p. |
|---|---|---|---|---|---|---|---|---|---|---|---|---|
| 322 | H | H | H | COOH | OH | | N | CH | C—CH₃ | N | CH₃ | Li⁺ salt >195 (decomp) |
| 323 | H | H | H | COOH | OH | | N | CH | C—OCH₃ | N | H | Li⁺ salt >225 (decomp) |
| 324 | H | H | H | COOH | OH | | N | CH | C—OCH₃ | N | OC₂H₅ | Li⁺ salt 195 (decomp) |
| 325 | H | H | H | COOH | OH | | N | CH | C—OCH₃ | N | Cl | |
| 327 | H | H | H | CONH—C₆H₅ | H | | N | CH | C—OCH₃ | N | OCH₃ | 96–98 |
| 328 | H | H | H | CON(CH₃)—(2-OCH₃-C₆H₄) | | =O | N | CH | C—OCH₃ | N | OCH₃ | 114–116 |
| 329 | H | H | H | CON(CH₃)—(2-Cl-C₆H₄) | | =O | N | CH | C—OCH₃ | N | OCH₃ | 146–148 |
| 379 | H | H | H | CON(C₂H₅)₂ | OH | | N | CH | C—OCH₃ | N | OCH₃ | 109–111 |
| 380 | H | H | H | CON(C₂H₅)₂ | OH | H | N | CH | C—OCH₃ | N | OCH₃ | |
| 381 | H | H | H | CON(iC₃H₇)₂ | | | N | CH | C—OCH₃ | N | OCH₃ | |
| 382 | H | H | H | CON(iC₃H₇)₂ | | H | N | CH | C—OCH₃ | N | OCH₃ | 146–148 |
| 383 | H | H | H | CON(CH₃)—OCH₃ | OH | | N | CH | C—OCH₃ | N | OCH₃ | |
| 384 | H | H | H | CON(CH₃)—OCH₃ | | =O | N | CH | C—OCH₃ | N | OCH₃ | |
| 385 | H | H | H | CON(CH₃)₂ | OH | | N | CH | C—OCH₃ | N | OCH₃ | 121–123 |
| 386 | H | H | H | CON(CH₃)₂ | | | N | CH | C—OCH₃ | N | OCH₃ | |

TABLE E-continued

| Cpd # | Y$_1$ | Y$_2$ | Y$_3$ | R | X | Y | W$_1$ | W$_2$ | W$_3$ | W$_4$ | R$_1$ | m.p. |
|---|---|---|---|---|---|---|---|---|---|---|---|---|
| 387 | H | H | H | CON-N(CH$_3$)(C$_6$H$_5$)·CH$_3$ | =O | H | N | CH | C—OCH$_3$ | N | OCH$_3$ | |
| 388 | H | H | H | CON-N(CH$_3$)(C$_6$H$_5$)·CH$_3$ | | H | N | CH | C—OCH$_3$ | N | OCH$_3$ | |
| 389 | H | H | H | CON(piperidine) | =O | H | N | CH | C—OCH$_3$ | N | OCH$_3$ | 131–133 |
| 390 | H | H | H | CON(piperidine) | OH | H | N | CH | C—OCH$_3$ | N | OCH$_3$ | |
| 391 | H | H | H | CON(morpholine) | =O | H | N | CH | C—OCH$_3$ | N | OCH$_3$ | |
| 392 | H | H | H | CON(morpholine) | OH | H | N | CH | C—OCH$_3$ | N | OCH$_3$ | |
| 393 | H | H | H | CONC$_6$H$_{13}$-CH$_3$ | | H | N | CH | C—OCH$_3$ | N | OCH$_3$ | NMR |
| 394 | H | H | H | CONC$_6$H$_{13}$-CH$_3$ | | H | N | CH | C—OCH$_3$ | N | OCH$_3$ | |

TABLE E-continued

| Cpd # | Y₁ | Y₂ | Y₃ | R | X | Y | W₁ | W₂ | W₃ | W₄ | R₁ | m.p. |
|---|---|---|---|---|---|---|---|---|---|---|---|---|
| 395 | H | H | H | CON—CH₂—Ph / CH₃ | =O | | N | CH | C—OCH₃ | N | OCH₃ | oil NMR |
| 396 | H | H | H | CON—CH₂—Ph / CH₃ | OH | H | N | CH | C—OCH₃ | N | OCH₃ | |
| 397 | H | H | H | CON—CH₂—(2-Cl-Ph) / CH₃ | =O | | N | CH | C—OCH₃ | N | OCH₃ | |
| 398 | H | H | H | CON—CH₂—(2-Cl-Ph) / CH₃ | OH | H | N | CH | C—OCH₃ | N | OCH₃ | |
| 399 | H | H | H | CONCH₂—(3-Cl-Ph) / CH₃ | =O | | N | CH | C—OCH₃ | N | OCH₃ | |
| 400 | H | H | H | CONCH₂—(3-Cl-Ph) / CH₃ | OH | H | N | CH | C—OCH₃ | N | OCH₃ | |

TABLE E-continued
| Cpd # | Y₁ | Y₂ | Y₃ | R | X | Y | W₁ | W₂ | W₃ | W₄ | R₁ | m.p. |
|---|---|---|---|---|---|---|---|---|---|---|---|---|
| 401 | H | H | H |  | =O | | N | CH | C—OCH₃ | N | OCH₃ | |
| 402 | H | H | H |  | OH | H | N | CH | C—OCH₃ | N | OCH₃ | 131–133 |
| 403 | H | H | H |  | =O | | N | CH | C—OCH₃ | N | OCH₃ | |
| 404 | H | H | H |  | OH | H | N | CH | C—OCH₃ | N | OCH₃ | |
| 405 | H | H | H |  | =O | | N | CH | C—OCH₃ | N | OCH₃ | 143–145 |
| 406 | H | H | H |  | OH | H | N | CH | C—OCH₃ | N | OCH₃ | |
| 407 | H | H | H | CONHC₂H₄S | OH | H | N | CH | C—OCH₃ | N | OCH₃ | gum NMR |
| 411 | H | H | H | CONHC₂H₄S(n)C₄H₉ | OH | H | N | CH | C—OCH₃ | N | OCH₃ | gum NMR |

TABLE E-continued

| Cpd # | Y$_1$ | Y$_2$ | Y$_3$ | R | X | Y | W$_1$ | W$_2$ | W$_3$ | W$_4$ | R$_1$ | m.p. |
|---|---|---|---|---|---|---|---|---|---|---|---|---|
| 413 | H | H | H | CON—CH$_2$—C≡CH<br>\|<br>CH$_3$ | =O | | N | CH | C—OCH$_3$ | N | OCH$_3$ | gum NMR |
| 428 | H | H | H | CONHSC$_4$H$_9$ | OH | H | N | CH | C—OCH$_3$ | N | OCH$_3$ | NMR (racemate) |
| 432 | H | H | H | CONHnC$_5$H$_{11}$ | OH | H | N | CH | C—OCH$_3$ | N | OCH$_3$ | NMR |
| 433 | H | H | H | CONHC$_7$H$_{15}$ | OH | H | N | CH | C—OCH$_3$ | N | OCH$_3$ | NMR |
| 434 | H | H | H | 3-F-C$_6$H$_4$-CONH | OH | H | N | CH | C—OCH$_3$ | N | OCH$_3$ | 143–145 |
| 435 | H | H | H | CONHCHC$_2$H$_5$<br>\|<br>COOCH$_3$ | OH | H | N | CH | C—OCH$_3$ | N | OCH$_3$ | NMR |
| 436 | H | H | H | CONH(s)C$_4$H$_9$ | OH | H | N | CH | C—OCH$_3$ | N | OCH$_3$ | NMR (both S(+) and R(−) forms) |
| 437 | H | H | H | CONHCH$_2$C≡CH | OH | H | N | CH | C—CH$_3$ | N | OCH$_3$ | NMR |
| 438 | H | H | H | | —C—N—<br>\|\|  \|<br>O  OH | OH | N | CH | C—OCH$_3$ | N | OCH$_3$ | 139–141 |
| 439 | H | H | H | 3-F-C$_6$H$_4$-CONH | OH | H | N | CH | C—OCH$_3$ | N | OCH$_3$ | 143–144 |
| 440 | H | H | H | 3-CH$_3$-C$_6$H$_4$-CONH | | | | CH | C—OCH$_3$ | N | OCH$_3$ | 133–134 |

TABLE E-continued

| Cpd # | Y₁ | Y₂ | Y₃ | R | X | Y | W₁ | W₂ | W₃ | W₄ | R₁ | m.p. |
|---|---|---|---|---|---|---|---|---|---|---|---|---|
| 441 | H | H | H | 4-NO₂-C₆H₄-N(CH₃)-CO- | =O | | N | CH | C—OCH₃ | N | OCH₃ | 117–120 |
| 442 | H | H | H | 2-CH₃-C₆H₄-NHCO- | OH | H | N | CH | C—OCH₃ | N | OCH₃ | 127–128 |
| 443 | H | H | H | 2,5-F₂-C₆H₃-NHCO- | OH | H | N | CH | C—OCH₃ | N | OCH₃ | 138–140 |
| 444 | H | H | H | 2,6-F₂-C₆H₃-NHCO- | OH | H | N | CH | C—OCH₃ | N | OCH₃ | 152–153 |
| 445 | H | H | H | 2-CH₃-4-(i)C₃H₇-C₆H₃-NHCO- | | H | N | CH | C—OCH₃ | N | OCH₃ | 108–110 |

TABLE E-continued

| Cpd # | Y₁ | Y₂ | Y₃ | R | X | Y | W₁ | W₂ | W₃ | W₄ | R₁ | m.p. |
|---|---|---|---|---|---|---|---|---|---|---|---|---|
| 446 | H | H | H | 3-(OC₂H₅)-C₆H₄-CONH | OH | H | N | CH | C—OCH₃ | N | OCH₃ | NMR |
| 447 | H | H | H | 3-F-4-(CH₃)-C₆H₃-CONH | OH | H | N | CH | C—OCH₃ | N | OCH₃ | 130–131 |
| 449 | H | H | H | 3-F-C₆H₄-CONH | OH | H | N | CH | C—OCH₃ | N | OCH₃ | 116–117 |
| 450 | H | H | H | 3-(CH₂OCH₃)-C₆H₄-CONH | OH | H | N | CH | C—OCH₃ | N | OCH₃ | NMR |
| 453 | H | H | H | 3-F-C₆H₄-CONH | OH | H | N | CH | C—OCH₃ | N | OCH₃ | 100–102 |
| 454 | H | H | H | COOH | =O | | N | CH | C—OCH₃ | N | OCH₃ | H₃N⁺C₃H₇ salt 201–203 |
| 455 | H | H | H | COOH | =O | | N | CH | C—OCH₃ | N | OCH₃ | H₂N⁺(CH₃)₂ salt 183–185 |

TABLE E-continued

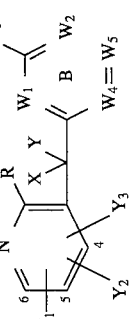

| Cpd # | Y₁ | Y₂ | Y₃ | R | X | Y | W₁ | W₂ | W₃ | W₄ | R₁ | m.p. |
|---|---|---|---|---|---|---|---|---|---|---|---|---|
| 456 | H | H | H | CON(CH₃)- (3-C₂H₅-C₆H₄) | =O | | N | CH | C—OCH₃ | N | OCH₃ | 115–116 |
| 457 | H | H | H | COOH | =O | | N | CH | C—OCH₃ | N | OCH₃ | H₂N⁺(iC₃H₇)₂ salt 185–187 |
| 458 | H | H | H | CON-allyl CH₃ | =O | | N | CH | C—OCH₃ | N | OCH₃ | NMR |
| 462 | H | H | H | CONHCH₂- (3-CH₂OCH₃-C₆H₄) | OH | | N | CH | C—OCH₃ | N | OCH₃ | NMR |
| 463 | H | H | H | CONHCH₂- (3-CF₃-C₆H₄) | OH | H | N | CH | C—OCH₃ | N | OCH₃ | NMR |
| 464 | H | H | H | COOH | =O | | N | CH | C—OCH₃ | N | OCH₃ | diCa⁺⁺ salt >240 |
| 465 | H | H | H | COOH | =O | | N | CH | C—OCH₃ | N | OCH₃ | diMg⁺⁺ salt >240 |
| 466 | H | H | H | COOH | =O | | N | CH | C—OCH₃ | N | OCH₃ | diAl⁺⁺OH salt >250 |
| 467 | H | H | H | CON-(4-F-C₆H₄) | | | N | CH | C—OCH₃ | N | OCH₃ | 148–150 |

TABLE E-continued

| Cpd # | $Y_1$ | $Y_2$ | $Y_3$ | R | X | Y | $W_1$ | $W_2$ | $W_3$ | $W_4$ | $R_1$ | m.p. |
|---|---|---|---|---|---|---|---|---|---|---|---|---|
| 468 | H | H | H | 3-CF₃-C₆H₄-NHCO- | OH | H | N | CH | C—OCH₃ | N | OCH₃ | 125-126 |
| 469 | H | H | H | 2,4-(OCH₃)₂-C₆H₃-NHCO- | OH | H | N | CH | C—OCH₃ | N | OCH₃ | NMR |
| 470 | H | H | H | 2,6-(C₂H₅)₂-C₆H₃-NHCO- | OH | H | N | CH | C—OCH₃ | N | OCH₃ | NMR |
| 471 | H | H | H | 4-(CH₂OCH₃)-C₆H₄-CH₂-NHCO- | OH | H | N | CH | C—OCH₃ | N | OCH₃ | NMR |
| 472 | H | H | H | 2,6-(CH₃)₂-C₆H₃-NHCO- | OH | H | N | CH | C—OCH₃ | N | OCH₃ | 137-138 |
| 473 | H | H | H | C₆H₅-N(CH₃)-CO- | OH | H | N | CH | C—OCH₃ | N | OCH₃ | NMR |

TABLE E-continued

| Cpd # | $Y_1$ | $Y_2$ | $Y_3$ | R | X | Y | $W_1$ | $W_2$ | $W_3$ | $W_4$ | $R_1$ | m.p. |
|---|---|---|---|---|---|---|---|---|---|---|---|---|
| 474 | H | H | H | CONpropargyl / CH$_3$ | OH | H | N | CH | C—OCH$_3$ | N | OCH$_3$ | 156–159 |
| 475 | H | H | H | CONHCH$_2$—C$_6$H$_4$—CH$_2$OCH$_3$ | OH | H | N | CH | C—OCH$_3$ | N | OCH$_3$ | NMR |
| 482 | H | H | H | COOH | OH | H | N | CH | C—OCH$_3$ | N | OCH$_3$ | H$_3$N$^+$(CH$_2$)$_3$—N(morpholine) salt NMR |
| 483 | H | H | H | COOH | OH | H | N | CH | C—OCH$_3$ | N | OCH$_3$ | H$_3$N$^+$C$_6$H$_{13}$ salt NMR |
| 484 | H | H | H | CONH—C$_6$H$_3$(CH$_3$)$_2$ | OH | H | N | CH | C—OCH$_3$ | N | OCH$_3$ | 113–115 |
| 485 | H | H | H | CONH—C$_6$H$_3$(CH$_3$)(C$_2$H$_5$) | =O | | N | CH | C—OCH$_3$ | N | OCH$_3$ | 147–148 |
| 487 | H | H | H | COOH | | | N | CH | C—OCH$_3$ | N | OCH$_3$ | H$_3$N$^+$C$_6$H$_{13}$ salt 165–167 |

TABLE E-continued

| Cpd # | Y₁ | Y₂ | Y₃ | R | X | Y | W₁ | W₂ | W₃ | W₄ | R₁ | m.p. |
|---|---|---|---|---|---|---|---|---|---|---|---|---|
| 488 | H | H | H | COOH | | =O | | N | CH | C—OCH₃ | N | OCH₃ | H₃N⁺(CH₂)₃—N(morpholino) salt |
| 490 | H | H | H | CONH-(4-Opropargyl-phenyl) | OH | | N | CH | C—OCH₃ | N | OCH₃ | 155–158 NMR |
| 491 | H | H | H | CONH-(3-Opropargyl-phenyl) | OH | H | N | CH | C—OCH₃ | N | OCH₃ | NMR |
| 492 | H | H | H | COOH | | =O | | N | OH | C—OCH₃ | N | OCH₃ | Al⁺(OH)₂ salt >250 |
| 493 | H | H | H | COOH | | =O | | N | OH | C—OCH₃ | N | OCH₃ | Al⁺⁺OH/Phe⁻ salt >250 |
| 494 | H | H | H | CONCH₂CN—CH₃ | | =O | | N | CH | C—OCH₃ | N | OCH₃ | 59–61 |
| 495 | H | H | H | CONH-(3,5-difluorophenyl) | OH | H | N | CH | C—OCH₃ | N | OCH₃ | 148–150 |
| 496 | H | H | H | CONCH₂CH₂OH—CH₃ | | =O | | N | CH | C—OCH₃ | N | OCH₃ | NMR |
| 497 | H | H | H | CONC₄H₉—CH₃ | | =O | | N | CH | C—OCH₃ | N | OCH₃ | NMR |

TABLE E-continued

| Cpd # | $Y_1$ | $Y_2$ | $Y_3$ | R | X | Y | $W_1$ | $W_2$ | $W_3$ | $W_4$ | $R_1$ | m.p. |
|---|---|---|---|---|---|---|---|---|---|---|---|---|
| 498 | H | H | H | CONHCHC$_3$H$_7$<br>$\|$<br>CH$_3$ | OH | H | N | CH | C—OCH$_3$ | N | OCH$_3$ | NMR |
| 500 | H | H | H | CONCH$_2$CH$_2$N(CH$_3$)$_2$<br>$\|$<br>CH$_3$ | =O | | N | CH | C—OCH$_3$ | N | OCH$_3$ | NMR |
| 501 | H | H | H | CONCH$_2$CH(OCH$_3$)$_2$<br>$\|$<br>CH$_3$ | =O | | N | CH | C—OCH$_3$ | N | OCH$_3$ | NMR |
| 505 | H | H | H | CONCH$_2$CH$_2$OH | OH | H | N | CH | C—OCH$_3$ | N | OCH$_3$ | NMR |
| 506 | H | H | H | CONHCH$_2$(i)C$_3$H$_7$<br>$\|$<br>CH$_2$OH | OH | H | N | CH | C—OCH$_3$ | N | OCH$_3$ | NMR |
| 507 | H | H | H | CON(C$_3$H$_7$)$_2$ | =O | | N | CH | C—OCH$_3$ | N | OCH$_3$ | 106-108 |
| 508 | H | H | H | CONCH$_2$—[dioxolane]<br>$\|$<br>CH$_3$ | =O | | N | CH | C—OCH$_3$ | N | OCH$_3$ | NMR |
| 509 | H | H | H | CONCH$_2$CH$_2$CN<br>$\|$<br>CH$_3$ | =O | | N | CH | C—OCH$_3$ | N | OCH$_3$ | NMR |
| 510 | H | H | H | CONHCH$_2$C=CH$_2$<br>$\|$<br>CH$_3$ | OH | H | N | CH | C—OCH$_3$ | N | OCH$_3$ | NMR |
| 513 | H | H | H | CONHCH$_2$CHC$_4$H$_9$<br>$\|$<br>OH | OH | H | N | CH | C—OCH$_3$ | N | OCH$_3$ | 115-117 |
| 514 | H | H | H | CONHCHC$_4$H$_9$<br>$\|$<br>CH$_3$ | OH | H | N | CH | C—OCH$_3$ | N | OCH$_3$ | 94-97 |

TABLE E-continued

| Cpd # | Y₁ | Y₂ | Y₃ | R | X | Y | W₁ | W₂ | W₃ | W₄ | R₁ | m.p. |
|---|---|---|---|---|---|---|---|---|---|---|---|---|
| 515 | H | H | H | CONHCHC=CH–CH₃ | OH | H | N | CH | C–OCH₃ | N | OCH₃ | NMR |
| 516 | H | H | H | CONHCH₂CHC₂H₅–OH | OH | H | N | CH | C–OCH₃ | N | OCH₃ | NMR |
| 517 | H | H | H | (cyclohexyl)CONH | OH | H | N | CH | C–OCH₃ | N | OCH₃ | NMR |
| 519 | H | H | H | CONHCH₂CH₂–N(imidazole) | OH | H | N | CH | C–OCH₃ | N | OCH₃ | NMR |
| 520 | H | H | H | CONH–(4-OnC₄H₉-phenyl) | OH | H | N | CH | C–OCH₃ | N | OCH₃ | 94–96 |
| 521 | H | H | H | CONnC₃H₇–CH₃ | =O | | N | CH | C–OCH₃ | N | OCH₃ | 78–79 |
| 522 | H | H | H | CONC₂H₅–CH₃ | =O | | N | CH | C–OCH₃ | N | OCH₃ | 94–96 |
| 427 | H | H | H | (piperidinyl)CON | =O | | N | CH | C–OCH₃ | N | OCH₃ | 131–133 |
| 499 | H | H | H | (pyrrolidinyl)CON | =O | | N | CH | C–OCH₃ | N | OCH₃ | 116–118 |
| 546 | H | H | H | CONHC₂H₅ | OH | H | N | CH | C–OCH₃ | N | OCH₃ | 48–50 |

TABLE E-continued

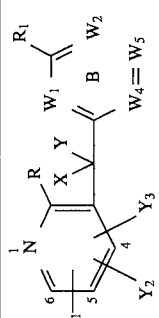

| Cpd # | Y₁ | Y₂ | Y₃ | R | X | Y₂ | Y₃ | Y | W₁ | W₂ | W₃ | W₄ | R₁ | m.p. |
|---|---|---|---|---|---|---|---|---|---|---|---|---|---|---|
| 558 | H | H | H | ![tC₄H₉, CONH-N, CH₃S] | OH | | | H | N | CH | C—OCH₃ | N | OCH₃ | 108–110 |
| 562 | H | H | 4-CH₃ | COOH | OH | | | H | N | CH | C—OCH₃ | N | OCH₃ | Li⁺ salt nmr |
| 569 | H | H | H | ![morpholine CON] | | =O | | | N | CH | C—OCH₃ | N | OCH₃ | 136–138 |
| 571 | H | H | H | CONCH₂COOC₂H₅ / CH₃ | | =O | | | N | CH | C—OCH₃ | N | OCH₃ | NMR |
| 573 | H | H | 4-OCH₃ | COOH | | =O | | | N | CH | C—OCH₃ | N | OCH₃ | 202–204 Li⁺ salt |
| 574 | H | H | 4-OCH₃ | COOH | | =O | | | N | CH | C—OCH₃ | N | OCH₃ | 200–210 |
| 575 | H | H | H | ![SCH₃ phenyl CON-CH₃] | | =O | | | N | CH | C—OCH₃ | N | OCH₃ | 122–124 |
| 576 | H | H | H | ![iC₃H₇ phenyl CON-CH₃] | | =O | | | N | CH | C—OCH₃ | N | OCH₃ | 128–131 |
| 579 | H | H | H | ![SO₂CH₃ phenyl CON-CH₃] | | =O | | | N | CH | C—OCH₃ | N | OCH₃ | 118–121 |

TABLE E-continued

| Cpd # | Y₁ | Y₂ | Y₃ | R | X | Y | W₁ | W₂ | W₃ | W₄ | R₁ | m.p. |
|---|---|---|---|---|---|---|---|---|---|---|---|---|
| 584 | H | H | H | CONCH₂CONH₂<br>\|<br>CH₃ | =O | | N | CH | C—OCH₃ | N | OCH₃ | 168–171 |
| 598 | H | H | H |  | =O | | N | CH | C—OCH₃ | N | OCH₃ | 150–152 |
| 602 | H | H | H | 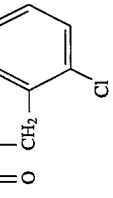 | =O | | N | CH | C—OCH₃ | N | OCH₃ | 152–154 |
| 603 | H | H | H | CON—OCH₃<br>\|<br>CH₃ | =O | | N | CH | C—OCH₃ | N | OCH₃ | 90–93 |
| 609 | H | H | H | CONCH₂CON(CH₃)₂<br>\|<br>CH₃ | =O | | N | CH | C—OCH₃ | N | OCH₃ | 167–170 |
| 622<br>625<br>626 | H<br>H<br>H | H<br>H<br>H | H<br>H<br>H | COOsC₄H₉<br>COOnC₄H₉<br>COOiC₄H₉ | =O<br>=O<br>=O | | N<br>N<br>N | CH<br>CH<br>CH | C—OCH₃<br>C—OCH₃<br>C—OCH₃ | N<br>N<br>N | OCH₃<br>OCH₃<br>OCH₃ | NMR<br>NMR<br>111–113 |
| 632 | H | H | H | —C—N—O—<br>\|\| \|<br>O CH₂<br>\|<br>(2-Cl-phenyl) | OH | | N | CH | C—OCH₃ | N | OCH₃ | 122–127 |
| 633 | H | H | H | —C—N—O—<br>\|\| \|<br>O CH₃ | OH | | N | CH | C—OCH₃ | N | OCH₃ | 142–144 |
| 634 | H | H | H | —C—N—O—<br>\|\| \|<br>O | OH | | N | CH | C—OCH₃ | N | OCH₃ | 156–158 |

(64: Lithium salt m.p. >250°; sodium salt m.p. >190° (decomp); potassium salt m.p. >230° (decomp))
Phe = Phenalanine anion

TABLE F

[Structure: AA-C(X)(Y)- attached to pyrimidine with two OCH3 groups]

| Cpd # | AA | X | Y | m.p. |
|---|---|---|---|---|
| 90 | [furo[3,4-b]pyridinone structure] | H | H | 123–125 |
| 331 | [3-methylisothiazole-4-COOH] | | =O | |
| 332 | " | OH | H | |
| 333 | [5-chloro-3-methylisothiazole-4-COOH] | | =O | |
| 334 | " | OH | H | |
| 335 | [3-methylpyrazole-4-COOH] | | =O | |
| 336 | " | OH | H | |
| 337 | [3-methylpyrazine-2-COOH] | | =O | |
| 338 | " | OH | H | |
| 339 | [2-methylthiazole-5-COOH] | | =O | |
| 340 | " | OH | H | |
| 341 | [5-methylthiazole-4-COOH] | | =O | |
| 342 | " | OH | H | |
| 343 | [5-methyloxazole-4-COOH] | | =O | |
| 344 | " | OH | H | |

TABLE F-continued

Structure: AA–C(X)(Y)–N=C(OCH3)–CH=C(OCH3)–N= (pyrimidine with two OCH3 groups)

| Cpd # | AA | X | Y | m.p. |
|---|---|---|---|---|
| 345 | 3-methyl-isoxazol-4-yl-COOH (oxazole ring with COOH) |  | =O |  |
| 346 | " | OH | H |  |
| 347 | 1-methyl-pyrazol-5-yl with COOH and 4-CH3 |  | =O |  |
| 348 | " | OH | H |  |
| 349 | 2-methyl-thiophen-3-yl-COOH |  | =O |  |
| 350 | " | OH | H |  |
| 351 | 3-methyl-thiophen-2-yl-COOH |  | =O |  |
| 352 | " | OH | H |  |
| 353 | 4-methyl-isothiazol-3-yl-COOH |  | =O |  |
| 354 | " | OH | H |  |
| 355 | 4-methyl-isoxazol-3-yl-COOH |  | =O |  |
| 356 | " | OH | H |  |
| 357 | 4-methyl-thiophen-3-yl-COOH |  | =O |  |
| 358 | " | OH | H |  |
| 359 | 2-methyl-furan-3-yl-COOH |  | =O |  |
| 360 | " | OH | H |  |

TABLE F-continued
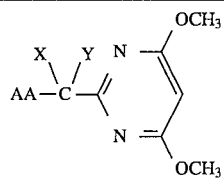
| Cpd # | AA | X | Y | m.p. |
|---|---|---|---|---|
| 361 | (furan-COOH, methyl) | | =O | |
| 362 | " | OH | H | |
| 363 | (furan-COOH, methyl) | | =O | |
| 364 | " | OH | H | |
| 365 | (thiadiazole-COOH, methyl) | | =O | |
| 366 | " | OH | H | |
| 367 | (oxadiazole-COOH, methyl) | | =O | |
| 368 | " | OH | H | |
| 369 | (thiadiazole-COOH, methyl) | | =O | |
| 370 | " | OH | H | |
| 371 | (oxadiazole-COOH, methyl) | | =O | |
| 372 | " | OH | H | |
| 373 | (pyrazine-COOH, methyl) | | =O | |
| 374 | " | OH | H | |
| 375 | (pyrazine-COOH, methyl) | | =O | |
| 376 | " | OH | H | |

TABLE F-continued $$\text{AA}-\underset{\underset{N}{\overset{X}{|}}}{\overset{\overset{OCH_3}{|}}{\underset{OCH_3}{C}}}$$

| Cpd # | AA | X | Y | m.p. |
|---|---|---|---|---|
| 377 | 2-COOH-naphthyl | | =O | |
| 378 | " | OH | H | |
| 410 | 3-phenyl-5-methyl-isoxazol-4-yl CON(CH₃)phenyl | H | H | 122–123 |
| 412 | " | H | O(t)C₄H₉ | gum NMR |
| 424 | " | OH | H | 130–131 |
| 429 | " | | =O | NMR |
| 430 | 2-methyl-3-[CON(CH₃)phenyl]-thien-yl | H | O(t)C₄H₉ | NMR |
| 431 | " | OH | H | NMR |
| 448 | 3-methyl-4-[CON(CH₃)phenyl]-isothiazol-yl | OH | H | NMR |
| 451 | 3-methyl-2-[CON(CH₃)phenyl]-thien-yl | OH | H | 143–144 |
| 511 | 5-Si(CH₃)₃-3-methyl-2-[CON(CH₃)phenyl]-thien-yl | H | H | NMR |
| 512 | " | H | O(t)C₄H₉ | NMR |
| 513 | 3-methyl-4-[CON(CH₃)phenyl]-isothiazol-yl | H | H | 92–93 |

TABLE F-continued structure: AA—C(X)(Y)— attached to pyrimidine with OCH₃ groups at both positions (N=C(OCH₃)—CH=C(OCH₃)—N)

| Cpd # | AA | X | Y | m.p. |
|---|---|---|---|---|
| 514 | " | | =O | 140–142 |
| 515 | 4-methyl-1,2,3-thiadiazol-5-yl with CON(CH₃)phenyl substituent | H | H | 177–179 |
| 530 | isothiazole with Si(CH₃)₃, CON(CH₃)phenyl, and methyl substituents | H | H | NMR |
| 564 | naphthyl-COO⁻Li⁺ | | =O | decompose 270 |
| 565 | naphthyl fused lactone (with X) | / | CN | 155–158 |
| 601 | pyridyl with C(=O)N(CH₃) ring (with X) | | OH | 124–126 |
| 635 | cyclohexenyl fused anhydride | H | H | 92–94 |

Compounds of Table F wherein COOH is replaced by other meanings of R as listed in Tables C, D and E above for R may be prepared analogously.

| | NMR data [¹H nmr (CDCl₃)] |
|---|---|
| Cpd No | |
| 41 | δ: 3.95(s, 6H, OCH₃), 5.95(s, 1H, pyrimidine H), 6.45(s, 1H, OCH), 7.7–9.1(m, 3H, pyridine H). |
| 44 | δ: 1.32(t, 3H, CH₃), 2.87(q, 2H, CH₂), 4.05(s, 6H, OCH₃), 6.3(s, 1H, OCH), 7.82(d, 1H., arom.), 8.72(d, 1H, arom.). |
| 46 | δ: 1,32(t, 3H, CH₃), 2.85(q, 2H, CH₂), 3.87(s, 6H, OCH₃), 5.97(s, 1H, pyrimidine H), 6.32(s, 1H, OCH), 8.08(d, 1H, pyridine H), 8.71(d, 1H, pyridine H). |
| 48 | δ: 1.25(s, 6H, CH₃), 3.85(s, 6H, OCH₃), 3.95(2H, OCH₂), 4.65(s, 2H, CH₂), 5.85(s, 1H, pyrimidine H), 7.2–8.0(4H, aromatic). |
| 49 | δ: 1.00(s, 6H, CH₃), 3.65 and 3.75(d of d, 2H, OCH₂), 6.05(s, 1H, pyrimidine H), |

-continued

NMR data [$^1$H nmr (CDCl$_3$)]

| Cpd No | |
|---|---|
| | 7.2–8.1(4H, aromatic H). |
| 54 | δ: 2.9(s, 3H, CH$_3$N), 3.10(s, 3H, CH$_3$O), 3.90(s, 6H, OCH$_3$), 6.10(s, H, pyrimidine H), 7.2–7.9(3H, aromatic H). |
| 61 | δ: 1.24(s, 6H, CH$_3$), 3.98(a, 2H, CH$_2$O), 4.74(a, 2H, CH$_2$), 7.16(s, 1H, pyrimidine H). |
| 65 | δ: 3.96(s, 6H, OCH$_3$), 5.96(9, 1H, pyrimidine H), 6.32(s, 1H, OCR), 7.27(d, 1H, thienyl H), 7.85(d, 1H, thienyl H). |
| 66 | δ: 4.08(s, 6H, OCH$_3$), 6.27(s, 1H, OCH), 7.18(d, 1H, thienyl H), 7.95 (d, 1H, thienyl H). |
| 76 | δ: 1.63(t, 3H, CH$_3$), 3.91(s, 6H, OCH$_3$), 4.1(q, 2H, OCH$_2$), 6.08(s, 1H, pyrimidine H), 7.2–7.8(m, 3H, aromatic H). |
| 83 | δ: 3.85(s, 6H, OCH$_3$), 4.58(d, 2H, NCH$_2$), 5.30(s, 1H, OH), 5.80(s, 1H, pyrimidine), 6.82(s, 1H, OCH), 7.25(s, 5H, aromatic), 7.40(dd, 1H, pyridine), 7.98(dd, 1H, pyridine), 8.45(dd, 1H, pyridine), 8.70(s, 1H, NH). |
| 84 | δ: 3.85(s, 6H, OCH$_3$), 4.05(t, 2H, NCH$_2$), 5.0–5.45(m, 3H, CH=CH$_2$), 5.85(s, 1H, pyrimidine), 6.80(s, 1H, OCH), 7.2–8.6(m, 3H, pyridine). |
| 86 | δ: 3.85(s, OCH$_3$), 5.37(s, OCH$_2$Ar), 5.85(s, pyrimidine), 6.80(d, OCH), 7.2–8.2(m, aromatic), mixture with cpd. 40. |
| 88 | δ: 4.00(s, 3H, OCH$_3$), 5.50(s, 2H, OCH$_2$), 6.05(s, 1H, pyrimidine H), 6.27(s, 1H, OCH) 7.1–7.7(m, 8H, aromatic H). |
| 95 | δ: 3.85(s, 6H, OCH$_3$), 5.42(s, 2H, OCH$_2$), 6.05(s, 1H, pyrimidine), 6.42(s, 1H, OCH), 7.25(s, 5H, aromatic), 7.30(dd, 1H, pyridine), 7.98(dd, 1H, pyridine), 8.90(dd, 1H, pyridine). |
| 97 | δ: 3.80(s, 6H, OCH$_3$), 5.35(s, 2H, OCH$_2$Ar), 5.85(s, 1H, pyrimidine), 6.65(s, 1H, OCH), 7.15–8.6(m, 8H, aromatic), mixture with cpd. 40. |
| 107 | δ: 1.92(s, 3H, C≡CCH$_3$), 3.98(s, 6H, OCH$_3$), 4.92(s, 2H, OCH$_2$), 6.07(s, 1H, pyrimidine), 6.58(s, 1H, OCH), 7.71(dd, 1H, pyridine), 8.20(dd, 1H, pyridine), 8.90(dd, 1H, pyridine). |
| 110 | δ: 0.91(t, 3H, CH$_3$), 1.53(m, 2H, CH$_2$) 3.37(m, 2H, CH$_2$), 3.81(s, 6H, OCH$_3$), 4.50(m, 3H, OH and NCH$_2$), 5.82(s, 1H, pyrimidine), 6.72(s, 1H, OCH), 7.37(dd, 1H, pyridine), 7.95(dd, 1H, pyridine), 8.45(dd, 1H, pyridine). |
| 112 | δ: 1.22(d, 6H, CH$_3$), 3.81(s, 6H, OCH$_3$), 4.20(s, 1H, NCH), 5.85(s, 1H, pyrimidine), 6.71(s, 1H, OCH), 7.38(dd, 1H, pyridine), 7.92(dd, 1H, pyridine), 8.25(s, 1H, NH), 8.47(dd, 1H, pyridine). |
| 119 | δ: 3.05(d, 3H, NCH$_3$), 3.94(s, 6H, OCH$_3$), 5.20(s, 1H, OH), 5.75(s, 1H, pyrimidine), 5.98(s, 1H, OCH), 7.26(d, 1H, pyridine H), 7.82(q, 1H, NH), 8.28(d, 1H, pyridine H). |
| 127 | δ: 3.75(s, 6H, OCH$_3$), 4.05(t, 2H, NCH$_2$), 5.05–5.5(m, 3H, CH=CH$_2$), 5.85(s, 1H, pyrimidine), 7.2–8.6(m, 9H, phenyl + OCH). |
| 128 | δ: 2.20(s, 3H, CH$_3$), 3.75(s, 6H, OCH$_3$), 4.10(t, 2H, NCH$_2$), 5.0–6.6(m, 3H, CH=CH$_2$), 5.85(s, 1H, pyrimidine), 7.2–8.6(m, 5H, pyridine + NH, OCH). |
| 130 | δ: 1.30(m, 15H, aliphatic), 2.26(s, 8H, aliphatic), 3.36(m, 2H, NCH$_2$), 3.83(9, 6H, OCH$_3$), 5.82(s, 1H, pyrimidine), 6.81(s, 1H, OCH), 7.38(dd, 1H, pyridine), 8.06(dd, 1H, pyridine), 8.29(s, 8.46(dd, 1H, pyridine). |
| 133 | δ: 2.85(d, 3H, NCH$_3$), 3.85(s, 6H, OCH$_3$), 4.10(t, 2H, NCH$_2$), 5.0–6.0(m, 3H, CH=CH$_2$), 5.85(s, 1H, pyrimidine), 7.2–8.6(s, 4H, pyridine + OCH). |
| 150 | δ: 0.96(t, 3H, CH$_3$), 1.68(s, 2H, CH$_2$), 3.50(m, 2H, NCH$_2$), 3.93(s, 6H, OCH$_3$), 5.92(s, 1H, pyrimidine H), 6.17(d, 1H, OCH), 7.21(d of d, 1H, pyridine H), 8.07(dd, 1H, pyridine H), 8.57(dd, 1H, pyridine H), 8.66(t, 1H, NH). |
| 151 | δ: 1.50(d, 3H, CH$_3$), 3.82(s, 6H, OCH$_3$), 5.21(s, 2H, NCH, OH), 5.81(s, 1H, pyrimidine), 6.85(s, 1H, OCH), 7.23(m, 6H, phenyl and pyridine), 7.89(dd, 1H, pyridine), 8.42(dd, 1H, pyridine) 8.62(s, 1H, NH). |
| 152 | δ: 2.18(s, 3H, CH$_3$), 3.89(s, 6H, OCH$_3$), 4.42(d, 2H, NCH$_2$), 5.81(s, 1H, pyrimidine), 6.85(s, 1H, OCH), 7.03(s, 4H, phenyl), 7.21(dd, 1H, pyridine), 7.91(dd, 1H, pyridine), 8.42(dd, 1H, pyridine), 8.51(s, 1H, NH). |
| 171 | δ: 1.24(t, 3H, CH$_3$), 2.60(q, 2H, CH$_2$), 3.86(s, 6H, OCH$_3$), 4.62(d, 2H, NCH$_2$), 5.86(s, 1H, pyrimidine H), 6.90(d, 1H, OCH), 7.0–8.54(m, 7H, phenyl), 8.60(bs, 1H, NH). |
| 174 | δ: 3.83(s, 3H, OCH$_3$), 3.90(s, 6H, OCH$_3$), 5.83(s, 1H, pyrimidine H), 6.60(d, 1H, OCH), 7.30(dd, 1H, pyridine H), 8.23(dd, 1H, pyridine H), 8.70(dd, 1H, pyridine H). |
| 177 | δ: 2.20(s, 6H, CH$_3$), 2.38(t, 2H, CH$_2$N), 3.42(q, 2H, NCH$_2$), 3.78(s, 6H, OCH$_3$), 4.88(br, 1H, NH) 5.75(s, 1H, pyrimidine), 6.61(s, 1H, OCH), 7.29(dd, 1H, pyridine), 7.80(dd, 1H, pyridine), 8.34(dd, 1H, pyridine). |
| 178 | δ: 3.85(s, 9H, OCH$_3$), 3.95(s, 3H, OCH$_3$), 4.14(s, 2H, CH$_2$), 5.82(s, 1H, pyrimidine H), 6.90(d, 1H, pyridine H), 8.12(d, 1H, pyridine H). |
| 187 | δ: 3.70(s, 9H, OCH$_3$), 5.82(s, 1H, pyrimidine H), ;6.80(d, 1H, pyridine H), 8.10(d, 1H, pyridine H). |
| 193 | δ: 1.00(d, 6H, CH$_3$), 3.78(s, 3H, OCH$_3$), 3.85(s, 6H, OCH$_3$), 4.72(q, 1H, CH), 5.50(d, 2H, OH and NCH), 5.82(s, 1H, pyrimidine), 6.88(s, 1H, OCH), 7.40(dd, 1H, pyridine), 7.98(dd, 1H, pyridine), 8.52(dd, 1H, pyridine), 8.78(s, 1H, NH). |
| 196 | δ: 3.78(s, 6H, OCH$_3$), 4.70(d, 2H, NCH$_2$), 5.35(s, 1H, OH), 5.81(s, 1H, pyrimidine), 6.28(m, 2H, furfuryl), 6.81(s, 1H, OCH), 7.30(m, 2H, furfuryl; pyridine), 7.98(dd, 1H, pyridine), 8.41(dd, 1H, pyridine), 8.67(s, 1H, NH). |
| 201 | δ: 1.87–2.04(m, 4H, CH$_2$ and tetrahydrofuran), 3.71–3.92(m, 9H, OCH$_3$ and tetrahydrofuran), 5.86–5.87(s, 2H, pyrimidine and OH), 6.74(d, 1H, OCH), 7.39(dd, 1H, pyridine), 7.88(dd, 1H, pyridine), 8.48(dd, 1H, pyridine), 8.55(s, 1H, NH). |
| 206 | δ: 2.22(s, 1H, CH$_3$), 3.85(9, 6H, OCH$_3$), 3.92(s, 3H, OCH$_3$), 3.97(s, 3H, OCH$_3$), 5.86(s, 1H, pyrimidine H), 6.80(s, 1H, OCH), 7.10(d, 1H, pyridine H), 8.16(d, 1H, pyridine H). |
| 209 | δ: 3.63(t, 3H, OCH$_3$), 3.74(s, 6H, OCH$_3$), 5.48–5.81(m, 4H, pyrimidine, OH, COCH), 6.88–7.42(m, 8H, phenyl, OCH, pyridine), 7.95(dd, 1H, pyridine), 8.46(dd, 1H, pyridine) 9.25(d, 1H, NH). |
| 212 | δ: 3.85(s, 6H, OCH$_3$), 4.41–4.52(m, 2H, NCH$_2$), 5.21–5.72(d, s, 4H, NH$_2$, pyrimidine, OH), 6.61(s, 1H, OCH), 7.12–7.32(m, 3H, pyridine, benzylsulfon), 7.71–7.80(m, 3H, pyridine, benzylsulfon), 8.3(d, 1H, pyridine), 8.71(m, 1H, NH). |
| 213 | δ: 3.61(s, 6H, OCH$_3$), 4.60(d, 2H, CH$_2$, OH), 4.90(s, 1H, OH) 5.72(s, 1H, pyrimidine), 6.72(s, 1H, OCH), 7.16–8.41(m, 7H, pyridine), 9.12(s, 1H, NH). |
| 214 | δ: 3.75(s, 6H, OCH$_3$), 4.73(d, 2H, NCH$_2$), 5.84(s, 1H, pyrimidine), 6.86–9.96(m, 3H, OCH, |

NMR data [$^1$H nmr (CDCl$_3$)]

Cpd No thiophone), 7.15(d, 1H, thiophene), 7.34(dd, Jcb=4.7, Jcd=7.9, 1H, pyridine), 7.96(dd, Jdc=7.9, Jdb=1.5, 1H, pyridine) 8.4(dd, Jbc=4.7, Jbd=1.5, 1H, pyridine), 8.71(d, 1H, NH).

216 δ: 1.31(t, 3H, CH$_3$), 2.62(s, 3H, CH$_3$), 3.87(s, 6H, OCH$_3$), 4.21(s, 2H, CH$_2$), 4.40(q, 2H, OCH$_2$), 5.83(s, 1H, pyrimidine H), 7.13(d, 1H, pyridine H), 8.44(d, 1H, pyridine H).

218 δ: 284(3.08)(s, 3H, NCH$_3$), 3.92(s, 6H, OCH$_3$), 4.50–5.03(m, 2H, NCH$_2$), 6.10(s, 1H, pyrimidine H), 7.10–7.80(m, 7H, aromatic H).

227 δ: 1.50(s, 6H, CH$_2$), 2.40(a. 6H, NCH$_2$), 3.55(q, 2H, NCH$_2$), 3.80(s, 6H, OCH$_3$), 5.85(s, 1H, pyrimidine H), 6.70(s, 1H, OCH), 7.15–8.60(m, 4H, 3 pyridine H + NH).

233 δ: 1.80(q, 2H, CH$_2$), 2.25(s, 6H, NCH$_3$), 2.35(q, 2H, NCH$_2$), 3.45(q, 2H, NCH$_2$), 3.80(s, 6H, CH$_3$), 5.80(s, 1H, pyrimidine), 6.65(s, 1H, OCH), 7.15–850(m, 3H, pyridine).

234 δ: 1.00(t, 6H, CH$_3$), 2.60(m, 6H, NCH$_2$), 3.50(q, 2H, NCH$_2$), 3.92(s, 6H, OCH$_3$), 5.80(s, 1H, pyrimidine H), 6.80(s, 1H, OCH), 7.15–8.7(m, 3H, pyridine).

236 δ: 1.37(t, 3H, CH$_3$), 2.56(s, 3H, CH$_3$), 3.87(s, 6H, OCH$_3$), 4.43(q, 2H, OCH$_2$), 5.87(s, 1H, pyrimidine H), 6.12(s, 1H, CHBr), 7.90(d, 1H, pyridine H), 8.56(d, 1H, pyridine H).

237 δ: 1.40(t, 3H, CH$_3$), 3.87(s, 6H, OCH$_3$), 4.43(q, 2H, OCH$_2$), 4.70(s, 2H, CH$_2$Br), 5.88(s, 1H, pyrimidine H), 6.23(s, 1H, CHBr), 8.07(d, 1H, pyridine H), 8.65(d, 1H, pyridine H).

238 δ: 1.37(t, 3H, CH$_3$), 2.06(s, 3H, CH$_3$), 3.88(s, 6H, OCH$_3$), 4.40(q, 2H, OCH$_2$), 5.28(s, 2H, OCH$_2$), 5.87(s, 1H, pyrimidine H), 6.23(s, 1H, CHBr), 8.04(d, 1H, pyridine H), 8.64(d, 1H, pyridine H).

257 δ: 3.82(s, 6H, OCH$_3$), 4.06(s, 2H, NCH$_2$), 5.08(s, 1H, OH), 5.43(s, 1H, NH), 5.87(s, 1H, OCH), 6.62(s, 1H, pyrimidine), 7.32–7.38(m, 6H, pyridine; phenyl), 7.88(dd, 1H, pyridine), 8.45(dd, 1H, pyridine), 9.55(s, 1H, NH).

264 δ: 0.8–1.9(br s, 25H, aliphatic), 3.85–3.90(s, 6H, OCH$_3$), 6.15(s, 1H, ArH, pyrimidine), 7.4(s, 2H, ArH).

277 δ: 0.90(t, 3H, CH$_3$), 1.2–1.7(m, 4H, aliphatic), 3.95(s, 6H, OCH$_3$), 4.08(t, 2H, OCH$_2$), 6.15(s, 1H, pyrimidine H), 7.5–7.7(m, 3H, aromatic).

281 δ: 0.90(t, 3H, CH$_3$), 1.3(m, 4H, aliphatic), 1.6(s, 2H, aliphatic), 3.95(s, 6H, OCH$_3$), 4.08(t, 2H, OCH$_2$), 6.15(s, 1H, pyrimidine H), 7.4–7.7(s, 3H, aromatic).

283 δ: 3.40(s, 6H, OCH$_3$), 3.43(s, 2H, NCH$_2$), 3.82(s, 6H, OCH$_3$), 4.47(t, 1H, CH), 5.75(s, 1H, OH), 5.86(s, 1H, pyrimidine), 6.77(s, 1H, OCH), 7.41(dd, 1H, pyridine), 7.96(dd, 1H, pyridine), 8.47(m, 2H, NH, pyridine).

284 δ: 1.75(s, 6H, CH$_3$), 2.31(s, 1H, C≡CH), 3.85(s, 6H, OCH$_3$), 5.62(d, 1H, OH), 5.85(s, 1H, pyrimidine), 6.85(d, 1H, OCH), 7.45(dd, 1H, pyridine), 7.95(dd, 1H, pyridine), 8.44–8.45(s, 2H, NH, pyridine).

285 δ: 0.85(t, 3H, CH$_3$), 1.48(m, 4H, CH$_2$), 3.41(m, 2H, NCH$_2$), 3.82(s, 6H, OCH$_3$), 5.75(m, 2H, OH, pyrimidine), 6.66(d, 1H, OCH), 7.31(dd, 1H, pyridine), 7.86(d, 1H, pyridine), 8.27(s, 1H, NH) 8.40(dd, 1H, pyridine).

286 δ: 1.28(t, 3H, CH$_3$), 3.38–3.58(m, 4H, CH, CH$_3$), 3.85(s, 6H, OCH$_3$), 4.18–4,48(s, 2H, CH$_2$), 5.88(s, 1H, pyrimidine), 6.73(3, 1H, OCH), 7.53–8.42(m, 4H, pyridine, NH).

290 δ: 3.74(s, 9H, OCH$_3$), 5.44(bs, 1H, OH), 5.73(s, 1H, pyrimidine), 6.62(bs, 1H, OCH), 6.9–8.6(m, aromatic, 7H), 10.22(s, 1H, NH).

291 δ: 1.40(m, 8H, CH$_2$), 2.28(s, 6H, NCH$_3$), 2.68(m, 2H, NCH$_2$), 3.40(m, 2H, NCH$_2$), 3.80(s, 6H, OCH$_3$), 5.80(s, 1H, pyrimidine), 6.70(s, 1H, OCH), 7.2–8.6(m, 4H, pyridine H + OH).

292 δ: 1.60(m, 4H, CH$_2$), 2.25(s, 6H, NCH$_3$), 2.25(m, 2H, NCH$_2$), 3.48(m, 2H, NCH$_2$), 3.65(s, 6H, OCH$_3$), 5.80(s, 1H, pyrimidine), 6.65(s, 1H, OCH), 7.2–8.6(m, 4H, pyridine + OH).

295 δ: 3.74(s, 6H, OCH$_3$), 3.80(s, 6H, OCH$_3$), 4.50(d, 2H, NCH$_2$), 5.84(s, 1H, pyrimidine), 6.5–8.6(m, 8H, phenyl, OCH, NH).

297 δ: 3.65(s, 6H, OCH$_3$), 3.77(s, 6H, OCH$_3$), 4.50(d, 2H, NCH$_2$), 5.64(d, 1H, OH), 5.80(s, 1H, pyrimidine), 6.25–6.60(m, 3H, phenyl), 6.8(d, 1H, OCH), 7.2–8.6(m, 3H, pyridine).

298 δ: 1.21(d, 3H, CH$_3$), 3.26(m, 1H, CH), 3.61(m, 2H, CH$_2$), 3.82(s, 6H, OCH$_3$), 5.86(s, 1H, pyrimidine), 6.7(s, 1H, OCH), 7.38(dd, 1H, pyridine), 7.90(dd, 1H, pyridine), 8.43(dd, 1H, pyridine), 8.61(br, 1H, NH).

299 δ: 0.85(t, 3H, CH$_3$), 1.2(m, 8H, aliphatic), 1.6(s, 2H, aliphatic), 3.95(s, 6H, OCH$_3$), 4.08(t, 2H, OCH$_2$), 6.15(s, 1H, pyrimidine H), 7.4–7.7(m, 3H, aromatic).

300 δ: 0.90(t, 3H, CH$_3$), 1.2(s, 10H, aliphatic), 1.6(m, 2H, aliphatic), 3.95(s, 6H, OCH$_3$), 4.08(t, 2H, OCH$_2$), 4.08(t, 2H, OCH$_2$), 6.15(s, 1H, pyrimidine H), 7.4–7.7(m, 3H, phenyl).

303 δ: 3.80(s, 6H, OCH$_3$), 3.90(d, 6H, OCH$_3$), 5.45(d, 1H, OH), 5.80(s, 1H, pyrimidine), 6.85(s, 1H, OCH), 7.0–8.6(s, 6H, phenyl), 10.2(s, 1H, NH).

305L(−) δ: 1.60(d, 3H, CH$_3$), 3.75(2s, 6H, OCH$_3$), 5.25(m, 1H, OH), 5.75(s, 1H, pyrimidine), 6.75(d, 1H, OCH), 7.2–8.6(m, 8H, aromatic).

308 δ: 0.88(t, 3H, CH$_3$), 1.25(bs, 18H, aliphatic), 1.6(s, 2H, aliphatic), 3.95(s, 6H, OCH$_3$), 4.07(t, 2H, O—CH$_2$), 6.15(s, 1H, pyrimidine H), 7.55–7.7(m, 3H, aromatic).

330 δ: 1.05(m, 6H, NCH$_2$CH$_3$), 1.27(s, 9H, C(CH$_3$)$_2$), 2.3(m, 4H, NCH$_2$), 3.8(s, 6H, OCH$_3$), 5.8(s, 1H, pyrimidine H), 5.9(s, 1H, CH—Ot—Bu), 7.18(d of d, 1H, pyridine H), 7.45(d of d, 1H, pyridine H), 8.6(d of d, 1H, pyridine H).

393 δ: 0.86(d, 3H, CH$_3$), 1.12–1.26(m, 8H, CH$_2$), 3.15(s, 3H, NCH$_3$), 3.32(m, 2H, CH$_2$), 3.93(s, 6H, OCH$_3$), 6.14(s, 1H, pyrimidine), 7.46(dd, Jca=4.8, Jcb=7.8, 1H, pyridine), 8.12(dd, Jba=1.3, Jbc=7.8, 1H, pyridine), 8.68(dd, Jab=1.2, Jac=4.8).

395 δ: 3.10(s, 3H, N—CH$_3$), 3.86(s, 6H, OCH$_3$), 4.58(s, 2H, CH$_2$), 6.06(s, 1H, pyrimidine), 7.18–8.69(m, 8H, pyridine, phenyl).

407 δ: 3.18(m, 2H, CH$_2$S), 3.65(s, 2H, CH$_2$N), 3.95(s, 6H, OCH$_3$), 5.85(s, 1H, pyrimidine), 6.80(s, 1H, OCH), 7.0–8.7(s, 8H, aromatic).

411 δ: 1.90(t, 3H, CH$_3$), 1.55(s, 4H, CH$_2$), 2.65(s, 4H, CH$_2$S), 3.62(m, 2H, CH$_2$N), 3.82(s, 6H, CH$_3$O), 5.90(s, 1H, pyrimidine), 6.75(s, OCH), 7.2–8.65(m, 3H, pyridine).

412 δ: 1.37(s, 9H, tBuO), 3.30(s, 3H, CH$_3$N), 3.90(s, 6H, CH$_3$), 5.95(s, 1H, pyrimidine), 5.97(s, 1H, OCH), 6.5–7.6(m, 10H, aromatic).

413 δ: 2.23(s, 1H, C≡CH), 3.12–3.23(d, 3H, N—CH$_3$), 3.93(s, 8H, OCH$_3$, N—CH$_2$C≡), 6.15(s, 1H, pyrimidine), 7.47–7.52(m, 1H, pyridine), 8.14–8.17(m, 1H, pyridine), 8.69–8.71(t, 1H, pyridine).

428 δ: 0.71–1.80(m, 8H, alphatic), 3.02(s, 6H, OCH$_3$), 3.92–4.20(m, 1H, NCH), 5.82(s, 1H, pyrimidine), 6.67(s, 1H, OCH), 7.20–8.50(m, 4H, pyridine + NH).

429 δ: 3.38(s, 3H, NCH$_3$), 4.02(s, 6H, OCH$_3$), 6.20(s, 1H, pyrimidine), 6.63–7.90(m, 10H, aromatic).

430 δ: 1.3(s, 9H, t-Bu), 3.4(s, 3H, N—CH$_3$), 3.9(s, 6H, OCH$_3$), 5.9(s, H, pyrimidine H), 6.57(s, 2H, CH—O + thiophene H), 7.05(m, 6H, thiophene H, phenyl).

-continued

NMR data [$^1$H nmr (CDCl$_3$)]

| Cpd No | |
|---|---|
| 431 | δ: 3.46(s, 3H, N—CH$_3$), 3.97(s, 6H, OCH$_3$), 5.2(d, 1H, OH), 5.87(s, 1H, pyrimidine H), 6.1(d, 1H, CH—O), 6.32(d, 1H, thiophene H), 6.75(d, 1H, thiophene H), 7.05(m, 5H, phenyl). |
| 432 | δ: 0.92(t, 3H, CH$_3$), 1.42(m, 6H, CH$_2$), 3.42(m, 2H, NCH$_2$), 3.85(s, 6H, OCH$_3$), 5.85(9, 1H, pyrimidine), 6.72(d, 1H, OCH), 7.22–9.60(m, 4H, pyridine + NH). |
| 433 | δ: 0.90(t, 3H, CH$_3$), 1.32(s, 10H, CH), 3.45(m, 2H, NCH$_2$), 3.92(s, 6H, OCH$_3$), 5.85(s, 1H, pyrimidine), 6.75(s, 1H, OCH), 7.2–8.6(m, 4H, pyridine + NH). |
| 435 | δ: 0.96(t, 3H, CH$_3$), 1.92(m, 2H, CH$_2$), 3.78(s, 3H, OCH$_3$), 3.86(s, 3H, OCH$_3$), 4.60(m, 1H, NCH), 5.86(s, 1H, pyrimidine), 6.86(d, 1H, OCH), 7.2–8.9(m, 4H, pyridine + NH). |
| 436 | (S)-(+)-amine δ: 0.76–1.74(s, 8H, CH$_3$, CH$_2$), 3.86(s, 6H, OCH$_3$), 4.06(m, 1H, NCH), 5.86(s, 1H, pyrimidine), 6.70(d, 1H, OCH), 7.60–8.60 (m, 4H, pyridine, NH). |
| 436 | (R)-(−)-amine δ: 0.70–1.85(m, 8H, CH$_3$, CH$_2$), 3.90(s, 6H, OCH$_3$), 4.05(m, 1H, NCH), 5.85(s, 1H, pyrimidine), 6.65(s, 1H, OCH), 7.20–8.60(m, 4H, pyridine, NH). |
| 437 | δ: 2.25(m, 1H, ≡CH), 2.45(s, 3H, CH$_3$), 3.80(s, 3H, OCH$_3$), 4.25(m, 2H, NCH$_2$), 6.38(s, 1H, pyrimidine), 6.95(s, 1H, OCH), 7.25–8.65(m, 4H, pyrimidine, NH). |
| 446 | δ: 1.45(t, 3H, CH$_3$), 3.82(s, 6H, OCH$_3$), 4.12(q, 2H, OCH$_2$), 5.42(d, 1H, OH), 5.88(s, 1H, pyrimidine), 6.72(m, 1H, OCH), 7.00–8.65(m, 7H, phenyl, pyridine), 10.32(s, 1H, NH). |
| 448 | δ: 3.45(s, 3H, NCH$_3$), 3.95(s, 6H, OCH$_3$), 5.35(s, 1H, OH), 5.95(s, 1H, pyrimidine), 6.15(s, 1H, OCH), 6.90–740(m, 5H, phenyl), 7.94(s, 1H, isothiazole). |
| 450 | δ: 3.38(s, 3H, NCH$_3$), 3.72(s, 6H, OCH$_3$), 4.47(s, 2H, CH$_2$), 5.38(s, 1H, OH), 6.94–8.62(m, 8H, OCH, benzene, pyridine), 10.64(s, 1H, NH). |
| 458 | δ: 3.10(s, 3H, N—CH$_3$), 3.95(m, 8H, CH$_2$, OCH$_3$), 5.19(m, 1H, =CH), 6.17(s, 1H, pyrimidine), 7.49(dd, 1H pyridine), 8.16(dd, 1H, pyridine), 8.69(dd, 1H, pyridine). |
| 462 | δ: 3.40(s, 3H, OCH$_3$), 3.82(s, 6H, OCH$_3$), 4.48(s, 2H, CH$_2$), 4.63(d, 2H, NCH$_2$), 5.73(d, 1H, OH), 5.88(s, 1H, pyrimidine), 6.80(d, 1H, OCH), 7.28–8.80(s, 8H, benzene, pyridine, NH). |
| 463 | δ: 3.83(s, 6H, OCH$_3$), 4.43(d, 1H, OH), 5.75(s, 1H, pyrimidine), 6.75(s, 1H, OCH), 7.10–8.45(m, 7H, phenyl, pyridine), 8.70(t, 1H, NH). |
| 469 | δ: 3.80(s, 6H, OCH$_3$), 3.90(d, 6H, OCH$_3$), 5.60(d, 1H, OH), 5.85(s, 1H, pyrimidine), 6.35–8.70(m, 7H, OCH, pyridine, phenyl), 10.30(s, 1H, NH). |
| 470 | δ: 1.10(t, 6H, CH$_3$), 2.53(q, 4H, CH$_2$), 3.75(s, 6H, OCH$_3$), 5.80(s, 1H, pyrimidine), 5.90(d, 1H, OH), 6.45(d, 1H, OCH), 7.00–8.60(m, 6H, phenyl, pyridine), 9.78(s, 1H, NH). |
| 471 | δ: 3.34(s, 3H, OCH$_3$), 3.37(s, 6H, OCH$_3$), 4.42(s, 2H, OCH$_2$), 4.63(d, 2H, NCH$_2$), 5.74(d, 1H, OH), 5.80(s, 1H, pyrimidine), 6.80(d, 1H, OCH), 7.22–8.50(M, 7H, phenyl, pyrimidine), 8.65(t, 1H, NH). |
| 473 | δ: 3.35(s, 3H, N—CH$_3$), 3.95(s, 6H, OCH$_3$), 6.27(s, 1H, CH), 6.66(s, 1H, pyrimidine), 6.93–9.93(d, 8H, phenyl, pyridine). |
| 475 | δ: 3.40(s, 3H, OCH$_3$), 3.75(s, 6H, OCH$_3$), 4.52(s, 2H, CH$_2$), 4.66(d, 2H, NCH$_2$), 5.82(d, 1H, OH), 5.85(s, 1H, pyrimidine), 6.76(d, 1H, OCH), 7.20–8.60(s, 7H, phenyl, pyridine), 8.85(t, 1H, NH). |
| 482 | δ: 2.20–2.70(s, 10H, NCH$_2$, CH$_2$), 3.40–3.80(m, 4H, OCH$_2$), 3.85(s, 6H, OCH$_3$), 5.85(s, 1H, pyrimidine), 6.20(s, 1H, OCH), 7.15–8.70(m, 3H, pyridine). |
| 483 | δ: 0.60–1.80(m, 11H, CH$_2$, CH$_3$), 2.60–3.00(m, 2H, NCH$_2$), 3.88(s, 6H, OCH$_3$), 5.85(s, 1H, pyrimidine), 6.20(s, 1H, OCH), 7.00–8.70(m, 3H, pyridine). |
| 490 | δ: 2.55(t, 1H, ≡CH), 3.82(s, 6H, OCH$_3$), 4.68(d, 1H, OCH$_2$), 5.45(d, 1H, OH), 5.85(s, 1H, pyrimidine), 6.90(d, 1H, OCH), 6.90–8.70(m, 7H, phenyl, pyridine), 10.25(s, 1H, NH). |
| 491 | δ: 2.55(t, 1H, ≡CH), 3.80(9, 6H, OCH$_3$), 5.42(d, 1H, OH), 5.84(s, 1H, pyrimidine), 6.90(m, 1H, OCH), 6.80–8.70(m, 7H, phenyl, pyridine), 10.40(s, 1H, NH). |
| 496 | δ 3.19(s, 3H, N—CH$_3$), 3.69(t, 2H, CH$_2$), 3.82(s, 2H, CH$_2$), 3.94(s, 6H, OCH$_3$), 6.17(s, 1H, pyrimidine), 7.55(dd, 1H, pyridine), 8.19(dd, 1H, pyridine), 8.61(dd, 1H, pyridine). |
| 497 | δ: 0.89(t, 3H, CH$_3$), 1.26(m, 4H, CH$_2$), 3.14(s, 3H, —NCH$_3$), 3.34(m, 2H, CH$_2$), 3.93(s, 6H, OCH$_3$), 6.15(s, 1H, pyrimidine), 7.46(dd, 1H, pyridine), 8.13(dd, 1H, pyridine), 8.68(dd, 1H, pyridine). |
| 498 | δ: 0.70–1.70(m, 10H, CH$_2$, CH$_3$), 3.85(s, 6H, OCH$_3$), 4.20(m, 1H, NCH), 5.85(s, 1H, pyrimidine), 5.95(d, 1H, OH), 6.68(d, 1H, OCH), 7.25–8.65(m, 4H, pyridine, NH). |
| 500 | δ: 2.30(s, 6H, N(CH$_3$)2), 3.19(s, 3H, N—CH$_3$), 3.54(m, 4H, CH$_2$), 3.94(s, 6H, OCH$_3$), 6.16(s, 1H, pyrimidine), 7.48(dd, Jca=2.8, Jcb=4.8, 1H, pyridine), 8.15(dd, Jbc=4.8, Jba=1.5, 1H, pyridine), 8.69(dd, Jca=2.8, Jab=1.5, 1H, pyridine). |
| 501 | δ: 3.16(s, 3H, NCH$_3$), 3.19–3.27(m, 9H, OCH$_3$, CH$_2$, CH), 3.71(s, 6H, OCH$_3$), 5.96(s, 1H, pyrimidine), 7.27–7.31(d, 1H, pyridine), 7.93–7.96(d, 1H, pyridine), 8.46–8.50(d, 1H, pyridine). |
| 505 | δ: 3.35–4.10(m, 6H, NCH$_2$, OCH$_2$, NH, OH), 3.80(s, 6H, OCH$_3$) 5.75(d, 1H, OH), 5.80(s, 1H, pyrimidine), 6.70(d, 1H, OCH), 7.20–8.50(m, 3H, pyridine), 8.60(s, 1H, NH). |
| 506 | δ: 1.00(m, 6H, CH$_3$), 1.60(m, 3H, CH$_2$, CH), 3.75–4.38(m, 6H, NH, NCH, CH$_2$OH), 3.88(s, 6H, OCH$_3$), 5.90(s, 1H, pyrimidine), 6.76(s, 1H, OCH), 7.28–8.72(m, 4H, pyridine, NH). |
| 508 | δ: 3.27(s, 3H, NCH$_3$), 3.53(d, 2H, CH$_2$), 3.61(t, 1H, CH), 3.82(m, 4H, CH), 3.87(s, 6H, OCH$_3$), 6.16(s, 1H, pyrimidine), 7.48(dd, 1H, pyridine), 8.14(dd, 1H, pyridine), 8.69(dd, 1H, pyridine). |
| 509 | δ: 3.25(s, 3H, NCH$_3$), 3.67(t, 2H, CH$_2$), 3.71(t, 2H, CH$_2$), 3.94(s, 6H, OCH$_3$), 6.19(s, 1H, pyrimidine), 7.50(dd, Jca=4.8, Jcb=7.8, 1H, pyridine), 8.18(dd, Jba=1.5, Jbc=7.8, 1H, pyridine), 8.72(dd, Jab=1.5, Jac=4.8, 1H, pyridine). |
| 510 | δ: 1.77(s, 3H, CH$_3$), 3.80(s, 6H, OCH$_3$), 3.98(d, 2H, N—CH$_2$), 4.90(s, 2H, =CH$_2$), 5.70(d, 1H, OH), 5.85(s, 1H, pyrimidine), 6.8(d, 1H, OCH), 7.2–7.5(m, 1H, pyridine), 7.8–8.05(d, 1H, pyridine), 8.4–8.6(d, 1H, pyridine). |
| 511 | δ: 0.18(s, 9H, Si(CH$_3$)$_3$), 3.47(s, 3H, N—CH$_3$), 3.90(s, 6H, OCH$_3$), 4.20(s, 2H, CH$_2$), 5.88(s, 1H, pyrimidine C—H), 7.04(s, 1H, thiophene C—H), 7.17(s, 5H, phenyl). |
| 512 | δ: 0.12(s, 9H, Si(CH$_3$)$_3$), 1.24(s, 9H, O-t-Bu), 3.38(s, 3H, N—CH$_3$), 3.84(s, 6H, OCH$_3$), 5.83(s, 1H, pyrimidine C—H), 6.20(s, 1H, CH—O), 7.05(s, 5H, phenyl), 7.37(s, 1H, thiophene, C—H). |
| 513 | δ: 0.75–1.15(t, 3H, CH$_3$), 1.15–1.70(m, 6H, CH$_2$), 2.25–2.70(m, 2H, OCH, OH), 3.45–4.00(m, 2H, NCH$_2$), 3.85(s, 6H, OCH$_3$), 5.85(s, 1H, pyrimidine), 6.80(s, 1H, OCH), 7.30–8.80(m, 4H, pyridine, NH). |

| NMR data [$^1$H nmr (CDCl$_3$)] | |
|---|---|
| Cpd No | |
| 514 | δ: 0.90(t, 3H, CH$_3$), 1.10–1.67(m, 9H, CH$_2$, CH$_3$), 3.85(s, 6H, OCH$_3$), 4.10(s, 1H, NCH), 5.90(s, 1H, pyrimidine), 5.94(d, 1H, OH), 6.80(d, 1H, OCH), 7.28–8.66(m, 4H, pyridine, NH). |
| 515 | δ: 1.606(m, 3H, CH$_3$), 2.30(m, 1H, ≡CH), 3.90(s, 6H, OCH$_3$), 3.92(m, 1H, NCH), 5.85(s, 1H, pyrimidine), 5.95(s, 1H, OH), 6.95(s, 1H, OCH), 7.20–8.70(m, 4H, pyridine, NH). |
| 516 | δ: 0.95(t, 3H, CH$_3$), 1.50(q, 2H, CH$_2$), 3.62(m, 2H, NCH$_2$), 3.85(s, 6H, OCH$_3$), 3.87(m, 1H, OCH), 5.35(s, 1H, OH), 5.85(s, 1H, pyrimidine), 6.75(d, 1H, OCH), 7.30–8.80(m, 4H, pyridine, NH). |
| 517 | δ: 1.00–2.25(m, 10H, CH$_2$), 3.85(s, 6H, OCH$_3$), 3.98(s, 1H, NCH), 5.85(s, 1H, pyrimidine), 5.88(d, 1H, OH), 6.68(d, 1H, OCH), 7.20–8.60(m, 4H, pyridine, NH). |
| 518 | δ: 3.78(s, 6H, OCH$_3$), 6.40(s, 1H, pyrimidine), 7.78(dd, Jca=4.7, Jcb=7.7, 1H, pyridine), 8.17(dd, Jbc=7.6, Jba=1.5, 1H, pyridine), 8.91(dd, Jac=4.7, Jab=1.5, 1H, pyridine). |
| 519 | δ: 2.12(m, 2H, CH$_2$), 3.44(m, 2H, NCH$_2$), 3.84(s, 6H, OCH$_3$), 4.00(m, 2H, NCH$_2$), 4.87(s, 1H, OH), 5.85(s, 1H, pyrimidine), 6.77(s, 1H, OCH), 6.90–8.68(m, 7H, pyridine, imidazole, NH). |
| 523 | δ: 1.33(t, 3H, CH$_3$), 3.85(s, 6H, OCH$_3$), 4.14(s, 2H, CH$_2$), 4.40(q, 2H, OCH$_2$), 5.87(s, 1H, pyrimidine H), 7.35(d, 1H, pyridine H), 8.33(d, 1H, pyridine H). |
| 530 | δ: 0.50(s, 9H, Si(CH$_3$)$_3$), 3.40(s, 3H, NCH$_3$), 3.85(s, 6H, OCH$_3$), 4.10(s, 2H, CH$_2$), 5.83(s, 1H, pyrimidine), 7.00–7.40(m, 5H, benzene). |
| 532 | δ: 3.01–3.50(m, 2H, CH$_2$OH), 3.59–3.61(s, 4H, OCH$_2$), 3.71–3.73(2, 2H, CH$_2$N), 3.99(s, 6H, OCH$_3$), 5.76(br s, 3H, NH), 6.08(s, 1H, pyrimidine), 7.27–7.31(m, 1H, aromatic), 7.45–7.51(s, 2H, aromatic). |
| 553 | δ: 1.41–1.46(t, 3H, CH$_3$), 3.89(s, 6H, OCH$_3$), 4.47–4.52(q, 2H, OCH$_2$), 5.93(s, 1H, CHBr), 6.52(s, 1H, pyrimidine), 8.35(d, 1H, J=5.25 Hz, pyridine), 8.83(s, 1H, J=5.25 Hz, pyridine). |
| 562 | δ: 2.5(s, 3H, CH$_3$), 3.9(s, 6H, OCH$_3$), 5.9(s, 1H, CHOH), 6.2(s, 1H, pyrimidine), 7.3(d, 1H, J=12 Hz, pyridine), 8.3(d, 1H, J=12 Hz, pyridine). |
| 571 | δ: 1.26(t, 3H, CH$_3$), 3.33(s, 3H, NCH$_3$), 3.94(s, 6H, OCH$_3$), 4.11(s, 2H, NCH$_2$), 4.25(q, 2H, OCH$_2$), 6.15(s, 1H, pyrimidine), 7.51(dd, Jca=4.8, ;Jcb=7.6, 1H, pyridine), 8.10(dd, Jbc=7.7, Jab=1.6, 1H, pyrimidine), 8.65(dd, Jac=4.8, Jab=1.6, 1H, pyridine). |
| 622 | δ: 0.84(t, 3H, CH$_3$), 1.08(d, 3H, CH$_3$), 1.56(m, 2H, CH$_2$), 3.89(s, 6H, OCH$_3$), 4.78(m, 1H, CH), 6.13(s, 1H, pyrimidine), 7.62(dd, Jca=4.8, Jcb=7.6, 1H, pyridine), 7.94(dd, Jba=1.6, Jbc=7.6, 1H, pyridine), 8.85(dd, Jab=1.6, Jac=4.8, 1H, pyridine). |
| 625 | δ: 0.87(t, 3H, CH$_3$), 1.28(m, 2H, CH$_2$), 1.54(m, 2H, CH$_2$), 3.89(s, 6H, OCH$_3$), 4.09(t, 2H, OCH$_2$), 6.13(s, 1H, pyrimidine), 7.62(dd, Jca=4.7, Jcb=7.7, 1H, pyridine), 7.99(dd, Jba=1.5, Jbc=7.7, 1H, pyridine), 8.84(dd, Jab=1.5, Jac=4.17, 1H, pyridine). |

What is claimed is:

1. A compound of formula I

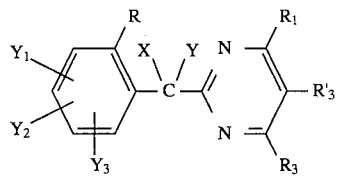

(I)

wherein

R is a carboxyl group which may be in the form of the free acid or in ester or salt form, a thiocarboxyl group which may be in the form of the free acid or in ester form, a carbamoyl group or a mono- or di- substituted carbamoyl group, $Y_1$, $Y_2$ and $Y_3$ are independently hydrogen, halogen, hydroxy, alkyl, alkenyl, alkynyl, alkoxy, alkenyloxy, alkynyloxy, alkylsulfonyloxy, dialkylsulfamoyloxy, alkylsulfonyl, alkylsulfinyl, dialkylcarbamoyloxy, alkylthio, alkenylthio or alkynylthio each of which may in turn be substituted by 1 to 6 halogen atoms; dialkoxymethyl, conjugated alkoxy, hydroxyalkyl, carboxyl, acyl, acylalkyl, acyloxy, acyloxyalkyl, trialkylsilyloxy, trialkylsilyl, cyano, nitro, amino or substituted amino, aminosulfonyl; cycloalkyl, aryl, aralkyl, aralkenyl, aralkynyl, aryloxy, aralkoxy, arylsulfonyl, arylsulfinyl, arylthio or aralkylthio, each of which may be substituted by one to three substituents selected from halogen, alkyl, haloalkyl, alkoxy, haloalkoxy, nitro, cyano, alkylthio, acyl, amino or substituted amino; a group

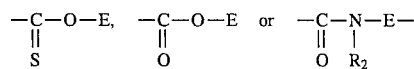

wherein R' is hydrogen, lower alkyl, or lower alkoxy; or $Y_1$ and R taken together on adjacent carbon atoms form a bridge having the formula

wherein E is a 1 to 3 membered linking group with elements selected from methylene, substituted methylene, $$-\underset{R_2}{\overset{|}{N}}-$$

and oxygen, and each $R_2$ is independently hydrogen, hydroxy, alkyl, haloalkyl, alkoxy, alkoxyalkyl, aralkoxy, or aryl or aralkyl, each of which is unsubstituted or may be substituted by 1 to 3 substituents selected from halogen; alkyl, alkenyl, alkynyl, alkoxy, alkoxyalkoxy, alkenyloxy, alkynyloxy, alkylsulfonyl, alkylsulfinyl, alkylthio, alkenylthio or alkynylthio, nitro, cyano, acyl, amino;

or $Y_1$ and $Y_2$ taken together on adjacent carbon atoms form a 3- to 5-membered bridge comprised of elements selected from methylene, substituted methylene,

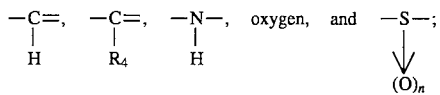

$R_1$, $R_3$, and $R'_3$ each is independently hydrogen; halogen; alkyl, alkenyl, alkynyl, alkoxy, alkenyloxy, alkynyloxy, alkylthio, alkenylthio or alkynylthio, each of which may in turn be substituted by 1 to 6 halogen atoms; cycloalkyl, heterocycloalkoxy, aryloxy, aralkoxy or aralkylthio each of which may be substituted by 1 to 3 substituents selected from halogen, alkyl, haloalkyl, alkoxy, haloalkoxy, nitro, cyano, alkylthio, acyl, amino or substituted amino; aminoxy; substituted aminoxy; iminoxy; substituted iminoxy; amino; substituted amino; amido; substituted amido; alkylsulfonylmethyl; cyano; nitro; or

wherein $Y_4$ is hydrogen, lower alkyl, lower alkoxy, hydroxy or unsubstituted or substituted phenyl;

$R_4$ is as deemed for $Y_1$ except for hydrogen;

X and Y taken together represent =O; or

X and R taken together may form the bridge,

wherein the carbonyl is attached to the phenyl ring, and Y is hydroxy, halogen, cyano, acyloxy, amino, substituted amino, alkoxycarbonyloxy, alkylsulfonyloxy, or carbamoyloxy.

2. A compound according to claim 1 wherein $Y_1$, $Y_2$ and $Y_3$ are independently hydrogen, halogen, hydroxy, alkyl, alkenyl, alkynyl, alkoxy, alkenyloxy, alkynyloxy, alkylsulfonyloxy, dialkylsulfamoyloxy, alkylsulfonyl, alkylsulfinyl, dialkylarbamoyloxy, alkylthio, alkenylthio or alkynylthio each of which may in turn be substituted by 1 to 6 halogen atoms; dialkoxymethyl, conjugated alkoxy, hydroxyalkyl, acyl, acyloxy, trialkylsilyloxy, trialkylsilyl, cyano, nitro, amino or substituted amino, aryl, aralkyl, aryloxy, aralkoxy, arylsulfonyl, arylsulfinyl, arylthio or aralkylthio, each of which may be substituted by one to three substituents selected from halogen, alkyl, haloalkyl, alkoxy, haloalkoxy, nitro, cyano, alkylthio, acyl, amino or substituted amino; a group

wherein R' is hydrogen, lower alkyl, or lower alkoxy; or $Y_1$ and R taken together on adjacent carbon atoms form a bridge having the formula

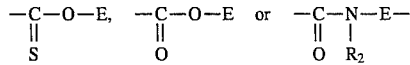

wherein E is a 1 to 3 membered linking group with elements selected from methylene, substituted methylene,

and oxygen and each $R_2$ is independently hydrogen, alkyl, haloalkyl, alkoxyalkyl or aryl or aralkyl, each of which is unsubstituted or may be substituted by 1 to 3 substituents selected from halogen, alkyl, alkenyl, alkynyl, alkoxy, alkoxyalkoxy, alkenyloxy, alkynyloxy, alkylsulfonyl, alkylsulfinyl, alkylthio, alkenylthio, alkynylthio, nitro, cyano, acyl, amino or substituted amino; or $Y_1$ and $Y_2$ taken together on adjacent carbon atoms form a 3- to 5-membered bridge comprised of elements selected from methylene, substituted methylene,

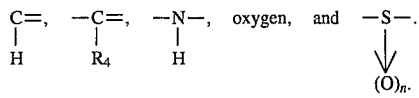

3. A compound according to claim 2 wherein $Y_1$, $Y_2$ and $Y_3$ are independently hydrogen, halogen, alkyl, alkenyl, alkynyl, alkoxy, alkenyloxy, alkynyloxy, alkyl sulfonyloxy, dialkylsulfamoyloxy, alkylsulfonyl, alkylsulfinyl, dialkylcarbamoyloxy, alkylthio, alkenylthio or alkynylthio each of which may in turn be substituted by 1 to 6 halogen atoms; dialkoxymethyl, alkoxyalkoxy, hydroxyalkyl, acyl, acyloxy, trialkylsilyloxy, trialkylsilyl, cyano, nitro, amino or substituted amino, aryl, aralkyl, aryloxy, aralkoxy, arylsulfonyl, arylsulfinyl, arylthio or aralkylthio, each of which may be substituted by one to three substituents selected from halogen, alkyl, haloalkyl, alkoxy, haloalkoxy, nitro, cyano, alkylthio, acyl, amino or substituted amino; a group

wherein R' is hydrogen, lower alkyl, or lower alkoxy; or $Y_1$ and $Y_2$ taken together on adjacent carbon atoms form a 3- to 5-membered bridge comprised of elements selected from methylene, substituted methylene,

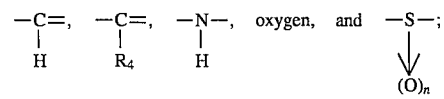

$Y_4$ is hydrogen, lower alkyl, lower alkoxy or hydroxy;

$R_4$ is as deemed for $Y_1$ except for hydrogen;

X and Y taken together represent =O; or

X and R taken together may form the bridge,

wherein the carbonyl is attached to the phenyl ring, and Y is hydroxy, halogen, cyano, acyloxy, amino, substituted amino.

4. A compound according to claim 1 wherein $Y_1$, $Y_2$ and $Y_3$ are independently hydrogen, halogen, alkyl or alkoxy; $R_1$, $R_3$ and $R_3'$ are independently hydrogen, halogen, alkyl, alkoxy, aryloxy, or aralkoxy.

5. A compound according to claim 2 wherein $Y_1$, $Y_2$ and $Y_3$ are independently hydrogen, halogen, alkyl or alkoxy; $R_1$, $R_3$ and $R_3'$ are independently hydrogen, halogen, alkyl, alkoxy, aryloxy, or aralkoxy.

6. A compound according to claim 3 wherein $Y_1$, $Y_2$ and $Y_3$ are independently hydrogen, halogen, alkyl or alkoxy; $R_1$, $R_3$ and $R_3'$ are independently hydrogen, halogen, alkyl, alkoxy, aryloxy, or aralkoxy.

7. A compound according to claim 1 wherein R represents carboxyl in the form of the free acid or in ester or salt form; substituted carbamoyl or, together with X represents

$Y_1$, $Y_2$ and $Y_3$ are independently hydrogen, halogen, alkyl, alkoxy, alkylthio or arylthio;

and $R_1$ and $R_3$ are independently halogen, alkyl, alkoxy, haloalkoxy, optionally substituted aryloxy, aralkoxy, alkynyloxy or alkenyloxy.

8. A compound according to claim 2 wherein R represents carboxyl in the form of the free acid or in ester or salt form; substituted carbamoyl or, together with X represents

$Y_1$, $Y_2$ and $Y_3$ are independently hydrogen, halogen, alkyl, alkoxy, alkylthio or arylthio;

and $R_1$ and $R_3$ are independently halogen, alkyl, alkoxy, haloalkoxy, optionally substituted aryloxy, aralkoxy, alkynyloxy or alkenyloxy.

9. A compound according to claim 3 wherein R represents carboxyl in the form of the free acid or in ester or salt form; substituted carbamoyl or, together with X represents

$Y_1$, $Y_2$ and $Y_3$ are independently hydrogen, halogen, alkyl, alkoxy, alkylthio, or arylthio and $R_1$ and $R_3$ are independently halogen, alkyl, alkoxy, haloalkoxy, optionally substituted aryloxy, aralkoxy, alkynyloxy or alkenyloxy.

10. A compound according to claim 1 wherein R is a carbamoyl group or a mono- or di-substituted carbamoyl group.

11. A compound according to claim 2 wherein R is a carbamoyl group or a mono- or di-substituted carbamoyl group.

12. A compound according to claim 3 wherein R is a carbamoyl group or a mono- or di-substituted carbamoyl group.

13. A compound according to claim 1 wherein $Y_1$, $Y_2$ and $Y_3$ are selected from the following meanings
   a) independently hydrogen or halogen
   b) $Y_1$ and $Y_2$ independently halogen and $Y_3$ hydrogen
   c) $Y_1$ ortho to R as chlorine or fluorine, $Y_2$ ortho to the bridge as hydrogen, chlorine or fluorine, $Y_3$ hydrogen
   d) $Y_1$ ortho to R as chlorine, $Y_2$ ortho to the bridge as hydrogen, chlorine or fluorine, $Y_3$ hydrogen.

14. A compound according to claim 3 wherein $Y_1$, $Y_2$ and $Y_3$ are selected from the following meanings
   a) independently hydrogen or halogen
   b) $Y_1$ and $Y_2$ independently halogen and $Y_3$ hydrogen
   c) $Y_1$ ortho to R as chlorine or fluorine, $Y_2$ ortho to the bridge as hydrogen, chlorine or fluorine, $Y_3$ hydrogen
   d) $Y_1$ ortho to R as chlorine, $Y_2$ ortho to the bridge as hydrogen, chlorine or fluorine, $Y_3$ hydrogen.

15. A compound according to claim 3 wherein $Y_1$, $Y_2$ and $Y_3$ are selected from the following meanings
   a) independently hydrogen or halogen
   b) $Y_1$ and $Y_2$ independently halogen and $Y_3$ hydrogen
   c) $Y_1$ ortho to R as chlorine or fluorine, $Y_2$ ortho to the bridge as hydrogen, chlorine or fluorine, $Y_3$ hydrogen
   d) $Y_1$ ortho to R as chlorine, $Y_2$ ortho to the bridge as hydrogen, chlorine or fluorine, $Y_3$ hydrogen.

16. A compound according to claim 1 wherein $R_3'$ is hydrogen and $R_1$ and $R_3$ are selected from the following meanings
   a) independently lower alkoxy
   b) both methoxy.

17. A compound according to claim 2 wherein $R_3'$ is hydrogen and $R_1$ and $R_3$ are selected from the following meanings
   a) independently lower alkoxy
   b) both methoxy.

18. A compound according to claim 3 wherein $R_3'$ is hydrogen and $R_1$ and $R_3$ are selected from the following meanings
   a) independently lower alkoxy
   b) both methoxy.

19. A compound according to claim 1 wherein R is selected from the following meanings
   a) a carboxyl group which may be in the form of the free acid or in ester or salt form
   b) a carboxyl group in salt form.

20. A compound according to claim 2 wherein R is selected from the following meanings
   a) a carboxyl group which may be in the form of the free acid or in ester or salt form
   b) a carboxyl group in salt form.

21. A compound according to claim 3 wherein R is selected from the following meanings
   a) a carboxyl group which may be in the form of the free acid or in ester or salt form
   b) a carboxyl group in salt form.

22. A compound according to claim 1 wherein R is a carboxyl group which may be in the form of the free acid or in ester or salt form;

$Y_1$, $Y_2$ and $Y_3$ are independently hydrogen or halogen;

$R_1$, and $R_3$ are independently lower alkoxy;

$R_3'$ is hydrogen;

X and Y together represent =O or X and R together form the bridge

wherein the carbonyl is attached to the phenyl ring and Y is hydroxy, halogen, cyano, acyloxy, amino, substituted amino, alkoxycarbonyloxy, alkylsulfonyloxy or carbamoyloxy.

23. A compound according to claim 22 wherein X and Y together represent =O or X and R together form the bridge

wherein the carbonyl is attached to the phenyl ring and Y is hydroxy, halogen, cyano, acyloxy, amino or substituted amino.

24. A compound according to claim 11 which is 4,7-dichloro-3-(4,6-dimethoxy- 2-pyrimidinyl)-3-hydroxyphthalide.

25. A compound according to claim 1 which is 3,6-dichloro-3-[(4,6 -dimethoxy-2-pyrimidinyl)carbonyl]benzoic acid isopropylammonium salt.

26. A compound according to claim 1 which is 3,6-dichloro-3-[(4,6 -dimethoxy-2-pyrimidinyl)carbonyl]benzoic acid sodium salt.

27. A compound according to claim 1 which is 4,7-dichloro-3-(4,6-dimethoxy- 2-pyrimidinyl)-3-hexanoyloxyphthalide.

28. A compound according to claim 1 which is 4,7-dichloro-3-(4,6-dimethoxy- 2-pyrimidinyl)-3-butyryloxyphthalide.

29. A compound according to claim 11 which is 6-chloro-2-[(4,6-dimethoxy-2-pyrimidinyl)carbonyl]-3-fluorobenzoic acid isopropyl ammonium salt.

30. A herbicidal composition comprising a herbicidally effective amount of a compound according to claim 11.

31. A herbicidal composition comprising a herbicidally effective amount of a compound according to claim 2.

32. A herbicidal composition comprising a herbicidally effective amount of a compound according to claim 3.

33. A method of combatting weeds which comprises applying thereto or to a locus thereof an herbicidally effective amount of a compound according to claim 1.

34. A method of combatting weeds which comprises applying thereto or to a locus thereof an herbicidally effective amount of a compound according to claim 2.

35. A method of combatting weeds which comprises applying thereto or to a locus thereof an herbicidally effective amount of a compound according to claim 3.

* * * * *